United States Patent
Hoffmann et al.

(10) Patent No.: US 9,060,513 B2
(45) Date of Patent: Jun. 23, 2015

(54) ANTIBIOTIC PEPTIDES

(75) Inventors: Ralf Hoffmann, Grosspösna (DE); Patricia Czihal, Leipzig (DE)

(73) Assignee: AMP-THERAPEUTICS GMBH, Leipzig (DE)

( * ) Notice: Subject to any disclaimer, the term of this patent is extended or adjusted under 35 U.S.C. 154(b) by 1041 days.

(21) Appl. No.: 12/670,118

(22) PCT Filed: Jul. 21, 2008

(86) PCT No.: PCT/EP2008/059512
§ 371 (c)(1),
(2), (4) Date: May 17, 2010

(87) PCT Pub. No.: WO2009/013262
PCT Pub. Date: Jan. 29, 2009

(65) Prior Publication Data
US 2010/0222268 A1    Sep. 2, 2010

(30) Foreign Application Priority Data

Jul. 23, 2007 (DE) .......................... 10 2007 036 128

(51) Int. Cl.
*C07K 7/08* (2006.01)
*A61K 38/00* (2006.01)
*A01N 37/46* (2006.01)
*A01N 63/02* (2006.01)

(52) U.S. Cl.
CPC ................ *A01N 37/46* (2013.01); *A01N 63/02* (2013.01); *A61K 38/00* (2013.01); *C07K 7/08* (2013.01)

(58) Field of Classification Search
None
See application file for complete search history.

(56) References Cited

U.S. PATENT DOCUMENTS

| | | | |
|---|---|---|---|
| 5,300,629 A | 4/1994 | Casteels et al. | |
| 2002/0041898 A1* | 4/2002 | Unger et al. | 424/486 |
| 2005/0058603 A1* | 3/2005 | Gao et al. | 424/9.32 |
| 2006/0003938 A1* | 1/2006 | Otvos | 514/12 |
| 2006/0264378 A1* | 11/2006 | Fujii et al. | 514/14 |

FOREIGN PATENT DOCUMENTS

| | | | |
|---|---|---|---|
| WO | WO 9501371 A1 * | 1/1995 | |
| WO | WO 95/23513 A1 | 9/1995 | |
| WO | WO 00/78956 | 12/2000 | |
| WO | WO 00/78956 A1 | 12/2000 | |
| WO | WO 02/079467 A2 | 10/2002 | |
| WO | WO 03/062266 A2 * | 7/2003 | |
| WO | WO 2009/013262 A1 | 1/2009 | |

OTHER PUBLICATIONS

Sato et al., Abstracts obtained from EAST on Jul. 30, 2013 for WO 95/1371; published 1995; the abstract obtained from EAST on Jul. 30, 2013; pp. 1-4.*
Sato et al., machine translation for WO 95/01371 obtained Aug. 11, 2013; pp. 1-13.*
Rosengren, et al., "Cyclization of pyrrhocoricin retains structural elements crucial for the antimicrobial activity of the native peptide", Biopolymers—Peptide Science Section 2004, vol. 76, No. 5, 2004, pp. 446-458.
Kragol, et al., "Identification of crucial residues for the antibacterial activity of the proline-rich peptide, pyrrhocoricin" European Journal of Biochemistry, vol. 269, No. 17, Sep. 1, 2002, pp. 4226-4237.
Borysowski, et al., "Fusion to cell-penetrating peptides will enable lytic enzymes to kill intracellular bacteria", Medical Hypotheses, vol. 74, No. 1, Jan. 2010, pp. 164-166.
Tomasz, A. "Multiple-antibiotic-resistant bacteria", New England J. Med., 1994, 330:1247-1251.
Wenzel, R.P. (1988) The mortality of hospital-acquired bloodstream infections: need for a vital stalistic?, Int. J. Epidemiol. 17:225-227.
Moellering, R.C., Jr. (1998) Problems with antimicrobial resistance in Gram-positive cocci, Clin. Infect. Dis. 26:1177-1178.
Hand, W.L. (2000) Current challenges in antibiotic resistance, Adolesc, Med. 11:427-438.
Hooper, D.C. (2001) Emerging mechanisms of fluoroquinolone resistance. Emerg, Infect. Dis. 7:337-341.
Jones, R.N. (2001) Resistance pattern among nosocomial pathogens: trend over the past few years, Chest 119:397S-404S.
Prachayasittikul, V., Lawung, R., and Bulow, L. (2000) Episome profiles and mobilizable beta lactamase plasmid in *Haemophilus ducreyi*. Southeast Asian J. Trop. Med. Public Health 31:80-84.
Teuber, M. (1999) Spread of antibiotic resistance with food-borne pathogens, Cell. Mol. Life Sci. 30:755-763.
Doppelt:Boman, H.G. (1995) Peptide antibiotics and their role in innate immunity. Annu. Rev. Immunol. 13:61-92.

(Continued)

*Primary Examiner* — Karlheinz R Skowronek
*Assistant Examiner* — Lianko Garyu
(74) *Attorney, Agent, or Firm* — Fanelli Haag PLLC

(57) ABSTRACT

This invention concerns novel antibiotic peptide and peptide derivates, especially for use in medicine. Further, the invention relates to compositions and methods for killing microbes, like bacteria or fungus, and methods to treat microbial infections. The invention further relates to a method for drug screening analysis. The peptides and peptide derivates have the general formula $Sub_1-X_1\ N\ X_2\ X_3\ P\ V\ Y\ I\ P\ X_4\ X_5\ R\ P\ P\ H\ P-Sub_2$ (SEQ ID NO:169) wherein $X_1$ is a neutral or positively charged moiety, $X_2$ is a polar or positively charged moiety, $X_3$ is a positively charged moiety, $X_4$ is a polar or positively charged moiety, $X_5$ is a proline or a proline derivate, $Sub_1$ being the free or modified N-terminus, and $Sub_2$ being the free or modified C-terminus. The peptides or peptide derivates according to the invention possess at least one of the following advantages compared to the natural occurring apidaecin peptides: (i) an increased half-live in mammalian serum due to a higher protease resistance and (ii) an increased antimicrobial activity against one or several bacterial strains, especially human pathogens, or fungus or other microbial infections (iii) show an enlarged spectrum of antimicrobial activity, (iv) do induce less resistance in microbes and (v) are not toxic to human cells including erythrocytes.

18 Claims, 8 Drawing Sheets

(56) References Cited

OTHER PUBLICATIONS

Barra, D., Simmaco, M. and Boman, H.G. (1998) Gene encoded peptide antibiotics and innate immunity. Do 'animacules' have defense budgets? FEBS Lett. 430:130-134.

Ludtke, S., He, K., and Huang. H. (1995) Membrane thinning caused by magainin 2, Biochemistry 34:16764-16769.

Wimley, W.C., Selsted, M.D., and White, S.H. (1994) Interactions between human defensins and lipid bilayers: evidence for formation of multimeric pores, Protein Sci. 3:1361-1373.

Shai, Y. (1995) Molecular recognition between membrane-spanning polypeptides, Trends Biochem. Sci. 20:460-464.

Wade, D., Boman, A., Wahlin, B., Drain, C.M., Andreu, D., Boman, H.G., and Merrifield, R.B. (1990) Proc. Natl. Acad. Sci. USA 87:4761-4765.

Steiner, H., Andreu, D., and Merrifield, R.B. (1988) Biochim. Biophys. Acta, 939:260-266.

Otvos, L., Jr., Bokonyi, K., Varga; I.; Otvos, B.II, Hoffmann, R., Ertl, H.D.J., Wade, J.D., McManus, A.M., Craik, D.J., and Bulet, P. (2000) Insect peptides with improved protease-resistance protect mice against bacterial infection. Protein Sci., 9:742-749.

Casteels, P., Ampe, C., Jacob, F., Vaeck, M., and Tempst, P. (1989) Apidaecins: antibacterial peptides from honeybees; EMBO J., 8:2387-2391.

Bulet, P., Dimaroq, J.L., Hetru, C., Lagueux, M., Charlet, M., Hegy, G., van Dorsselaer, A., and Hoffmann, J.A. (1993) A novel inducuible antibacterial peptide form *Drosophila* carries and O-glycosylated substitution, J.Biol. Chem., 268:14893-14897.

Mackintosh. J.A., Veal, D.A., Beattie, A.J., and Golley, A.A. (1998) Isolation from an ant *Myrmecia gulosa* of two inducible O-glycosylated proline-rich antibacterial peptides, J. Biol. Chem., 273:6139-6143.

Cociancich, S., Dupont, A., Hegy, G., Lanot, R., Holder, F., Hetru, C., Hoffmann, J.A., and Bulet P. (1994) Novel inducible antibacterial peptides from a hemipteran insect, the sap sucking-bug *Pyrrhocoris apterus*, Biochem. J., 300-567-575.

Merrifiled, R.B. (1963) Solid Phase Peptide Synthesis. I, The Synthesis of a Tetrapeptide J. Am. Chem. Soc., 85:2149-2154.

Stemmer, W.P., Crameri, A., Ha, K.D., Brennan, T.M., Heyneker, H.L. (1995) Single-step assembly of a gene and entire plasmid from large numbers of oligodeoxyribonucleotides, Gene, 164:49-53.

Gething, M.J. and Sambrook, J. (1981) Cell-surface expression of influenza haemagglutinin from a cloned DANN the RNA gene, Nature, 293:620-625.

Maeno, M., Taguchi, S., Momose, H. (1993) Production of antibacterial peptide 'apidaecin' using the secretory expression system of *Streptomyces*, Biosci. Biotechnol. Biochem, 57:1206-1207.

Zhou, Q.F., Luo, X.G., Ye, L., Xi, T. (2007) High-level production of a novel antimicrobial peptide perinerin in *Escherichia* by fusion expression, Curr. Microbiol., 54:368-370.

Si, L.G., Lui, X.C., Lu, Y.Y., Wang, G.Y., Li, W.M. (2007) Soluble expression of active human beta-defensin-3 in *Escherichia coli* and its effects on the growth of host cells, Chin. Med. J. (Engl)., 120:708-713.

Noren, C.J,, Anthony-Cahill, S.J., Griffith; M.C. and Schultz, P.G. (1989) A general method for site-specific incorporation of unnatural amino acids into proteins, Science. 244:182-186.

Eliman, J., Mendel, D., Anthony-Cahill, S., Noren, C.J., Schultz, P.G. (1991) Biosynthetic method for introducing unnatural amino acids site-specifically into proteins, Meth. Enzymol., 202:301-336.

Anderson, W.F. (1998) Human gene therapy, Nature, 392, Supp., pp. 25-30.

Posnett, D.N., McGrath, H. and Ta, J.P. (1988) A novel method for producing anti-peptide antibodies. Production of site-specific antibodies to the T cell antigen receptor beta-chain, J. Biol. Chem., 263:1719-1725.

Morell, M., Espargaró, A., Avilés, F.X. and Ventura, S. (2007) Detection of transient protein-protein interactions by bimolecular fluorescence complementation: The abl-SH3 case. Proteomics 7: 1023-1036.

G.B. Fields and Noble, R. (1990) Solid phase peptide synthesis utilizing 9-fluorenylmethoxycarbonyl amino acids, Int. J. pepl. Pretein Res. 35:161-214.

Hoffmann, R., Vasko M. and Otvos, L., Jr. (1997) Serum stability of phosphopeptides. Anal. Chim. Acta 352:319-325.

Ryge, T.S. and Hansen, P.R. (2006) Potent antibacterial lysine-peptoid hybrids identified from a positional scanning combinatorial library, Bioorg. Med. Chem., 14:4444-4451.

Park, Y., Lee, D.G., Jang, S.H., Woo, E.R., Jeong, H.G., Choi, C.H., and Hahm, V.S. (2003) A Leu-Lys-rich antimicrobial peptide: activity and mechanism, Biochim. Biophys. Acta, 1645:172-182.

Kragol G, et al., The antibacterial peptide pyrrhocoricin inhibits the ATPase actions of DnaK and prevents chaperone-assisted protein folding, Biochemistry, 40:3016-3026, 2001.

Schneider M, et al., Differential infectivity of two *Pseudomonas* species and the immune response in the milkweed bug, oncopeltus fascialus (Insecta: *Hemiptera*), Journal of Invertebrate Pathology, 78:135-140, 2001.

Chernysh S., Cociancich S., Briand J.P., Hetru C., Bulet P., The inducible antibacterial peptides of the hemipteran insect *Palomena prasina*: Identification of a unique family of proline-rich peptides and of a novel insect defensing, Journal of Insect Physiology, 42:81-89, 1996.

Pujals S., Giralt E., Proline-rich, amphipathic cell-penetrating peptides, Adv. Drug. Deliv. Rev., 60(4-5):473-484, 2008.

Tam J.P., Mora A.L., Rao C., Lipidation as a novel approach to mucosal immunization Modulation of the Immune Response to Vaccine Antigens, 92:109-116, 1998.

Sieber P., An improved method for anchoring of 9-Fluorenylmethoxycarbonyl-Amino Acids to 4-Alkoxybenzyl alcohol resins, Tetrahedron Letters, 28:6147-6150, 1987.

Beckes B.J., Ellman J.A., An Alkanesulfonamide Safety-Catch linker for solid-phase synthesis, The Journal of Organic Chemistry, 84:2322-2330, 1999.

Slater T.F., Sawyer B., Strauli U., Studies on Succinate-Tetrazolium Reductase system. 3. Points of Coupling of 4 different tetrazolium salts, Biochimicha et Biophysica Acta, 77:383, 1963.

Berridge M.V., Tan A.S., Characterization of the cellular reduction of 3-(4,5-dimethylthiazol-2-Y1)-2,5-Diphenyltetrazolium bromide (Mtt)—subcellular-Localization, Substrate dependent, and involvement of mitochondrial electron-transport in Mtt reduction, Archives of Biochemistry and Biophysics, 303:474-482, 1993.

Bobbo, et al., Journal of Peptide Science, vol. 12, No. Suppl. S, 2006, p. 109 & 29th European Peptide Symposium; Gdansk, Poland; Retrieved from the internet: URL:http//www.29eps.com/docs/0217.doc.

Taguchi, et al., "In Vivo Monitoring System for Structure-Function Relationship Analysis of the Antibacterial Peptide Apidaecin", Applied and Environmental Microbiology; vol. 60, No. 10, 1994. pp. 3566-3572.

Ambesi, et al., "Alanine-scanning Mutagenesis along Membrane Segment 4 of the Yeast Plasma Membrane $H^{30}$-ATPase", The Journal of Biological Chemistry; vol. 271, No. 38, 1996, pp. 22999-23005.

Jacobsen, et al., "Single Amino Acid Substitutions in *k*-Conotoxin PVIIA Disrupt Interaction with the *Shaker* $K^+$Channel", The Journal of Biological Chemistry; vol. 275, No. 32, 2000, pp. 24689-24644.

Luo, et al., "Structure—Function Study and Anti-HIV Activity of Synthetic Peptide Analogues Derived from Viral Chemokine vMIP-II", Biochemistry, vol. 39, 2000, pp. 13545-13550.

Japanese Office Action; Application No. 2010-517379; dated Jun. 4, 2013, 4 pages. (Translation Attached).

Czihal et al., "P2084 Antimicrobial activity of apidaecin peptides", International Journal of Antimicrobial Agents, Elsevier Science, vol. 29 (2007), p. S602.

Knappe et al., "Chemical modifications of short antimicrobial peptides from insects and vertebrates to fight multi-drug resistant bacteria", Biopolymers, vol. 88, No. 4 (2007), p. 612.

Weinstein, "Chemistry and Biochemistry of Amino Acids, Peptides and Proteins, Passage", Chemistry and Biochemistry of Amino Acids, Peptides, and Proteins, vol. 7 (1983), pp. 266-357.

Li Wei-Fen et al., "Apidaecin-type peptides: Biodiversity, structure-function relationships and mode of action", Peptides, vol. 27, No. 9 (2006), pp. 2350-2359.

Dutta et al., "Functional mapping of apidaecin through secondary structure correlation", International Journal of Biochemistry and Cell Biology, vol. 40, No. 5 (2007), pp. 1005-1015.

\* cited by examiner

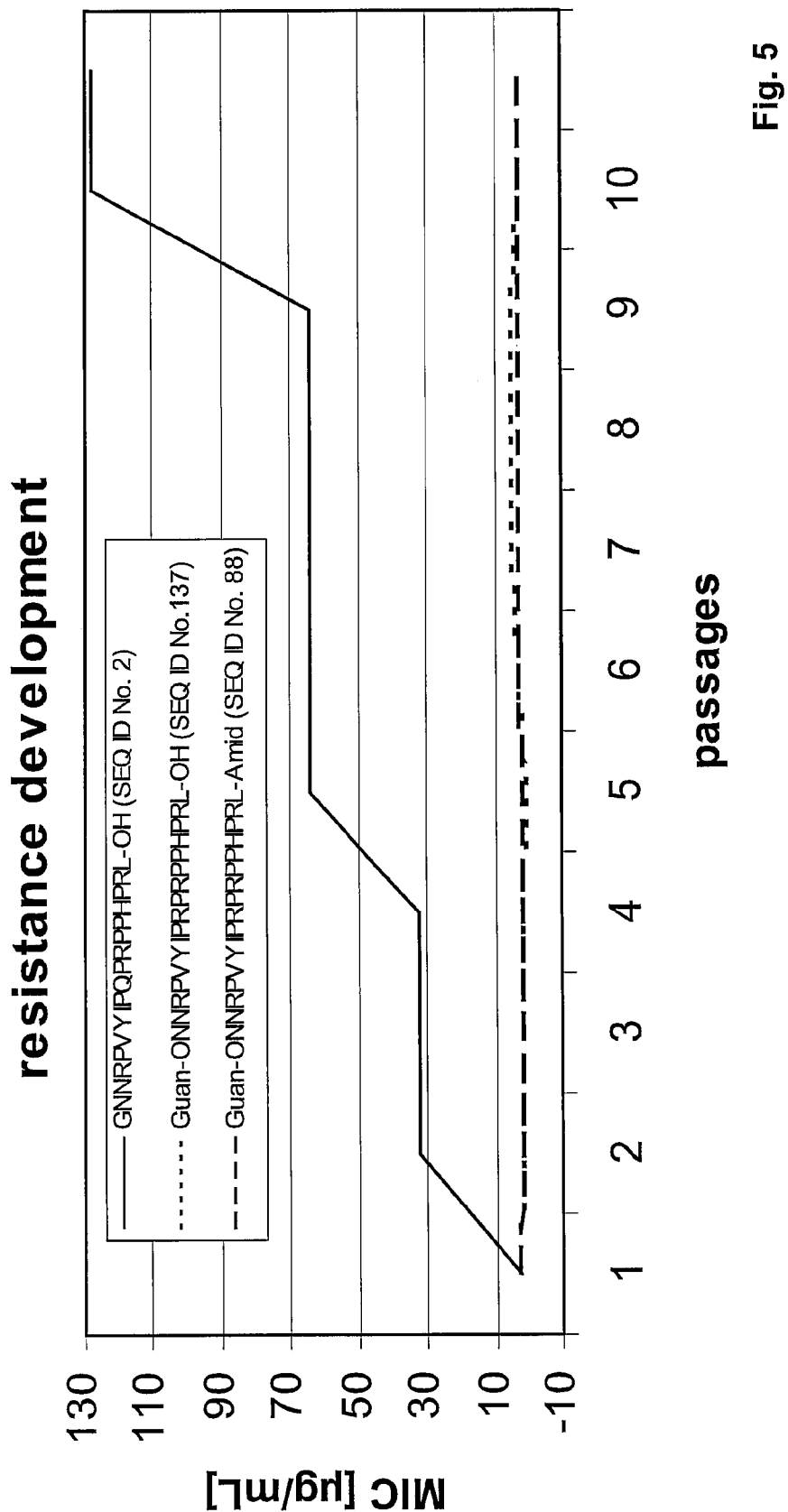

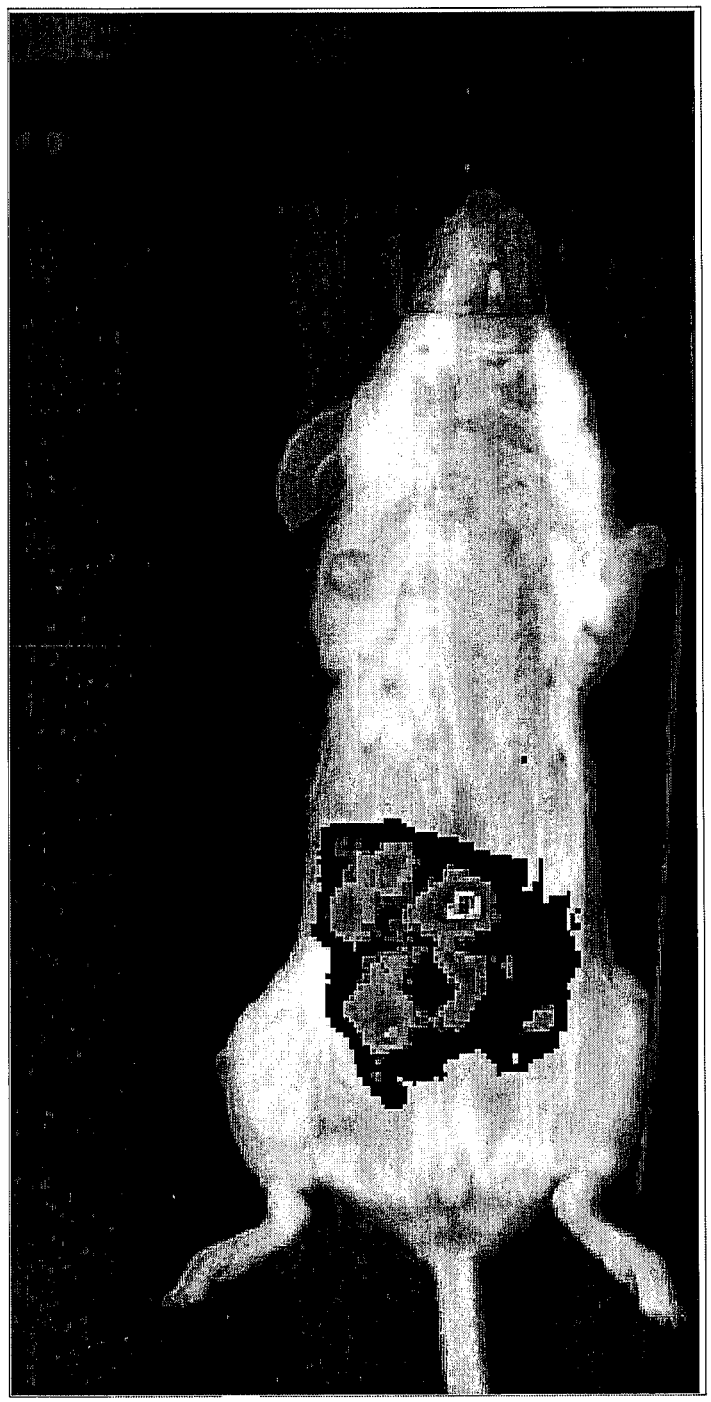

ANTIBIOTIC PEPTIDES

The instant application contains a Sequence Listing which has been submitted via EFS-Web and is hereby incorporated by reference in its entirety. Said ASCII copy, created on Jul. 3, 2012, is named 10801US1.txt and is 74,767 bytes in size.

This invention concerns novel antibiotic peptide and peptide derivatives, especially for use in medicine.

Further, the invention relates to compositions and methods for killing microbes, like bacteria or fungus, and methods to treat microbial infections. The invention further relates to a method for drug screening analysis.

The incidence of serious bacterial and fungal infections is increasing despite remarkable advances in antibiotic therapy. Each year there are more than 40 million hospitalizations in the United States, and about 2 million patients acquire nosocomial infections, 50 to 60% of which involve antibiotic-resistant bacteria [1]. The number of deaths related to nosocomial disease is estimated at 60,000-70,000 annually in the USA and up to 10.000 in Germany [2]. Whereas resistant Gram-negative bacteria were a major problem in the 1970s, the past decade has seen a climb in number of incidents with multi-drug resistant Gram-positive strains [3]. Currently, the rapid emergence of resistant strains involves both Gram-positive and Gram-negative pathogens [4]. Resistance developed first in species in which single mutations were sufficient to cause clinically important levels, such as *Staphylococcus aureus* and *Pseudomonas aeruginosa*, followed by bacteria in which multiple mutations are required, such as *E. coli* and *Neisseria gonorrhoeae*. This is mainly due to the broad use of fluoroquinolones [5]. Important causes of Gram-negative resistance include extended spectrum lactamases in *Escherichia coli* and *Klebsiella pneumoniae* [6]. Almost half of the clinical strains of *Haemophilus ducreyi*, the causative agent of chancroid, carries genes to confer resistance to amoxicillin, ampicillin and a series of other β-lactams [7]. Likewise, for *Salmonella enterica* serovar Typhimurium, resistance towards tetracyclines has increased from zero in 1948 to a 98% level in 1998 [8].

This necessitates a continuing search for novel antibiotics. Inducible antibacterial peptides represent a field of study where contemporary biochemistry, immunology and drug design converge. Peptide antibiotics, ranging in size from 13 to more than a hundred amino acid residues, have been isolated from plants, animals and microbes [9]. A single animal produces about 6-10 peptide antibiotics, each peptide often exhibiting a completely different activity spectrum [10]. It is well-established that the overwhelming majority of antibacterial peptides, including the well-studied defensins, cecropins and magainins, function through a "lytic/ionophoric" mechanism. Common theme among all "lytic" peptides is a permeabilizing effect on bacterial cytoplasmic membranes [11, 12, 13]. A cationic, amphipathic structure that enables formation of hydrophilic ion (proton) channels in a lipid bilayer is fundamental to this activity; proton leakage causes dissipation of the membrane potential, required for many vital life processes, thus causing cell death. As perturbation of membranes by these peptides is not dependent on recognition of chiral molecules, amino acid substitutions that do not abrogate general amphipathic structure or basic net charge are functionally tolerated [14, 15]. Peptides acting directly on the bacterial membrane often have also toxic effects on mammalian membranes at higher concentrations, which limits there potential as future drugs. When prolines are inserted into the sequences of α-helical antimicrobial peptides, the peptides' ability to permeabilize the cytoplasmic membrane of *E. coli* decreases substantially as the function of the number of proline residues incorporated. In this regard, it is intriguing that some of the most active native antibacterial peptides, at least against selected Gram-negative pathogens, belong to the proline-rich peptide family [16].

Such side effects might be overcome by other antimicrobial peptides that target specific bacterial proteins or other intra- or extracellular compounds without cross-reactivity to the mammalian analogs. This seems to be true for proline-rich antimicrobial peptides, including apidaecin, originally isolated from insects. With this enormous variation in size and biochemical properties, it is not surprising that structure-activity and conformation-activity relationships are the focus of antibacterial peptide studies. A complete fine-tuning of the natural antibacterial peptide repertoire to their biological potencies is not only important in general biochemistry terms, but is an ongoing interest of the pharmaceutical industry. In spite of problems with the in vitro testing of peptide-based antibiotics, a few native cationic antibacterial peptides have already reached the clinical trial stage [17]. While some of these have shown signs of efficacy in early clinical trials as topical agents, others show activity as systemic therapy. For example, the cationic protein rBPI 21 has recently completed phase III clinical trials of parenteral use for meningococcaemia [17].

Apidaecin, which was originally isolated from honeybees, belongs to the family of proline-rich antimicrobial peptides and shows sequence similarities to pyrrhocoricin, drosocin and formaecin (Table 1) [18]. Apidaecins are 18-20 residue-long peptides containing only unmodified L-amino acids with highly conserved PRPPHPRI/L SEQ ID NO:168 C-termini and a relatively high content of proline (33%). They can be easily synthesized on solid phase using the regular Fmoc/$^t$Bu strategy. The peptide inhibits viability of many gram negative bacteria in nanomolar doses whereas gram positives are unaffected. Lethal activity is near immediate and was shown to be independent of the conventional "lyric" mechanism [19]. In addition, apidaecin-resistant mutants are of undiminished sensitivity to "pore-forming" peptides and the D-enantiomer is devoid of antibacterial activities. The current model is that the antagonistic effects of apidaecin on bacteria involve stereoselective recognition of chiral targets [19]. The pro line-rich antimicrobial peptides including apidaecin as a member of this family do not merely kill bacteria by permeabilizing their membranes, but bind stereospecificaliy to a target protein, which has not identified for apidaecin, and ultimately leading to cell death. Moreover, in sharp contrast to AMPs with defined secondary structures like mellitin or gramdicidin S, the pro line-rich peptides appear to be non-toxic in-vitro to eurcaryotic cells and are not haemolytic. In mammalian serum apidaecin is completely degradaded within one hour due to cleavages at the N- and C-termini, which might be a result of amino- and carboxypeptidase cleavage, endoprotease cleavage or all of them. The before mentioned metabolites lost the antimicrobial activity with the MIC values typically above 125 μg/mL.

TABLE 1

Comparison of sequences from apidaecin 1a or 1b (*Apis mellifera*) [18], drosocin (*Drosphila melanogaster*) [20], formaecin 1 (*Myrmecia gulosa*) [21], and pyrrhocoricin (*Pyrrhocoris apterus*) [22].

| SEQ ID No. | Peptide | Sequence |
|---|---|---|
| 1 | Apidaecin 1a | GNNRPVYIPQPRPPHPRI |

TABLE 1-continued

Comparison of sequences from apidaecin 1a or 1b (*Apis mellifera*) [18], drosocin (*Drosphila melanogaster*) [20], formaecin 1 (*Myrmecia gulosa*) [21], and pyrrhocoricin (*Pyrrhocoris apterus*) [22].

| SEQ ID No. | Peptide | Sequence |
|---|---|---|
| 2 | Apidaecin 1b | GNNRPVYIPQPRPPHPRL |
| 161 | Drosocin | GKPRPYSPRPTSHPRPIRV |
| 162 | Formaecin 1 | GRPNPVNNKPTPYPHL |
| 163 | Pyrrhocoricin | VDKGSYLPRPTPPRPIYNRN |

There is still a need for novel anti-bacterial and anti-fungal compounds, novel anti-bacterial and anti-fungal pharmaceutical compositions, methods of use thereof, and novel compounds which can be employed in drug screening analysis to detect new pharmaceutical antibiotics.

One objective of the invention is to provide novel antibiotic peptides, preferably with raised stability. Another objective of the invention is to provide a method for drug screening analysis.

BRIEF DESCRIPTION OF THE DRAWINGS

FIG. 5 shows the induction of resistance, comparing wild type Apidaecin 1b (SEQ. ID No. 2) and two optimized sequences according to the invention (SEQ. ID NO: 88 and 137).

FIGS. 6A-6C show the in vivo imaging and biodistribution of the fluorescent labelled peptide. Dy675-ONNRPVY-IPRPRPPHPRL-NH$_2$ (SEQ ID NO: 160) 60 and 65 minutes after intra-peritional injection. Shown are the images after 60 min (FIG. 6A, belly, low intensity), 65 min (FIG. 6B, belly, high intensity) and after 65 min (FIG. 6C, back, high sensitivity). The colour bar indicates the fluorescence intensity. The labelled fluorescent peptide derivative was injected i.p. and its distribution was studied by in-vivo imaging at several time points. FIG. 6C taken from the back clearly shows that the peptides were enriched in brain, liver, and both kidneys. In FIG. 6B the brain is also stained Whereas the kidneys and liver are not seen due to the high peptide concentration at the injection site.

Figure 1:
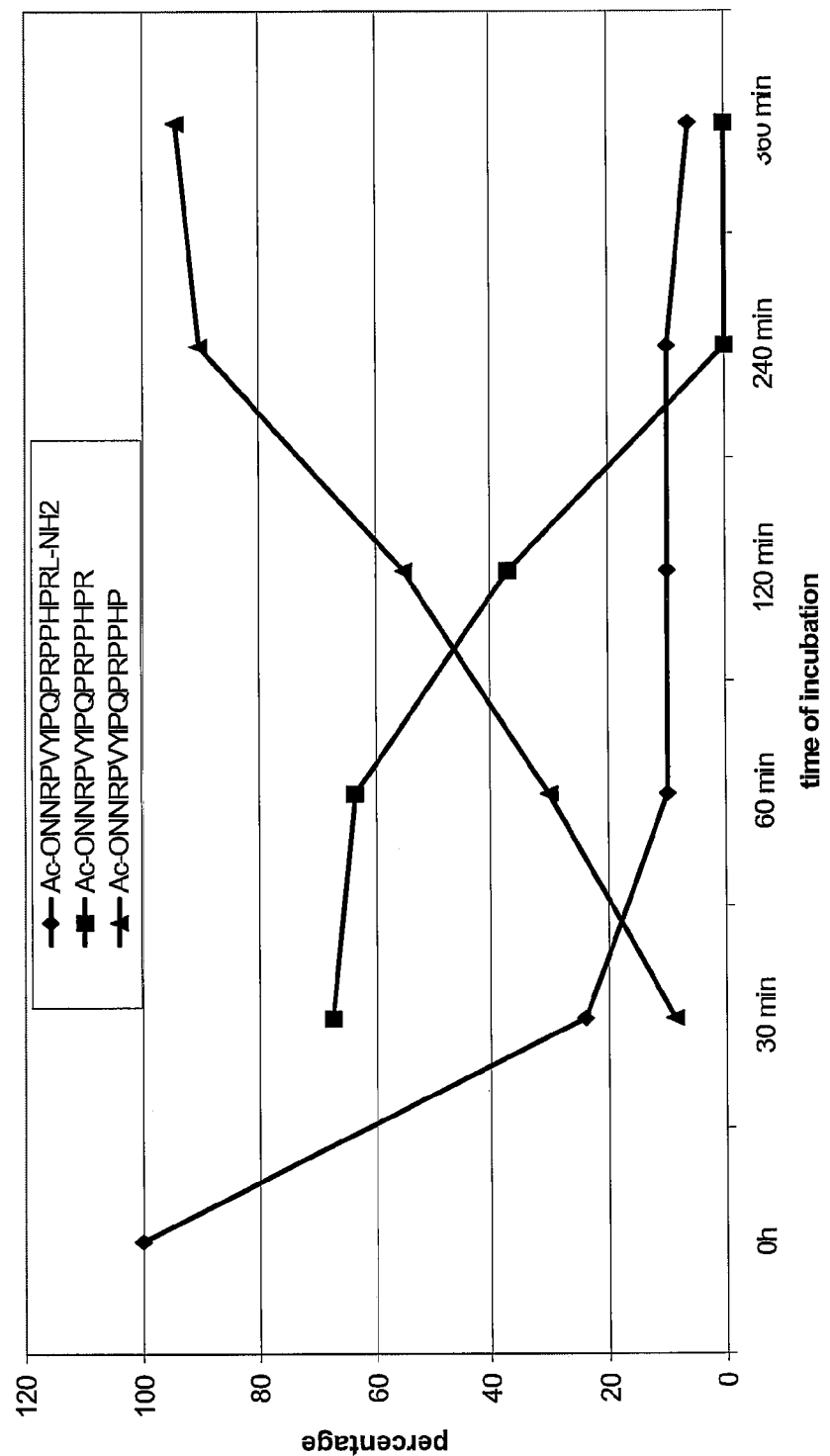
FIG. 1 shows the amounts of peptide Ac-ONNRPVY-IPQPRPPHPRL-NH$_2$ (SEQ ID No. 7) present in 25% aqueous serum after 30, 60, 120, 240, and 360 min as well as the two detected metabolites Ac-ONNRPVYIPQPRPPHPR-OH (SEQ ID NO. 164—cleavage of C-terminal leucine amide) and Ac-ONNRPVYIPQPRPPHP-OH (SEQ ID NO. 165—cleavage of two C-terminal residues) as quantified by the peak areas obtained by RP-HPLC using UV detection.

This first objective is solved by the peptide or peptide derivative according to the invention, with at Fast 16 residues and the general formula (Formula 1)
Sub$_1$-X$_1$-N-X$_2$-X$_3$-P-V-Y-I-P-X$_4$-X$_5$-R-P-P-H-P-Sub$_2$ SEQ ID NO: 169 wherein

X$_1$ is a neutral residue or a moiety having a net positive charge or a positively charged side chain under physiological conditions, which still carries a positive charge after modification with Subi. Preferred residues X$_1$ is preferably selected from the group of neutral residues (such as cis-4-hydroxyproline, trans-4-hydroxyproline, cis-3-hydroxyproline, trans-3-hydroxyproline, citrulline, N-methylserine, N-methylglycine, dihydroxyphenylalanine, N-ethylasparagine, N-ethylglycine, homoserine, penicillamine, tetrahydropyranylglycine, allo-threonine, 3,5-dinitrotyrosine) or positively charged residues including arginine, δ-hydroxylysine, homoarginine, β-homoarginine, D-arginine, methylarginine (preferably alpha-N-methylarginine), nitroarginine (preferably N(G)-Nitroargenine), nitrosoarginine (preferably N(G)-Nitrosoargenine), arginal (—COOH in Arginine is replaced by —CHO), guanidine propionic acid, 2,4-diaminobutyric acid, β-homoarginine, ε-N-methyllysine, allo-hydroxylysine, 2,3-diaminopropionic acid, 2,2'-diaminopimelic acid, lysine, ornithine, sym-dimethylarginine, asym-dimethylarginine, 2,6-diaminohexynoic acid, histidine, 1-methyl-histidine, 3-methyl-histidine, p-aminobenzoic acid, and 3-amino-tyrosine; nitrosoarginine (preferably N(G)-Nitrosoargenine), arginal, guanidine propionic acid, ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexynoic acid, histidine, 1-methyl-histidine, p-aminobenzoic acid, 3-methyl-histidine, and 3-amino-tyrosine;

X$_2$ is a residue with a polar side chain (such as asparagine, serine, citrulline or glutamine) or a moiety having a net positive charge or a positively charged side chain under physiological conditions (such as lysine or arginine, ornithine or homoarginine). Preferred residues X$_2$ are selected from the groups including asparagine, glutamine, serine, threonine, citrulline, cis-4-hydroxyproline, trans-4-hydroxyproline, cis-3-hydroxyproline, trans-3-hydroxyproline, citrulline, N-methylserine, N-methylglycine, dihydroxyphenylalanine, N-ethylasparagine, N-ethylglycine, homoserine, penicillamine, tetrahydropyranylglycine, allo-threonine, 3,5-dinitrotyrosine as well as arginine, lysine, δ-hydroxylysine, homoarginine, 2,4-diaminobutyric acid, homoarginine, β-homoarginine, D-arginine, methylarginine (preferably alpha-N-methylarginine), nitroarginine (preferably N(G)-Nitroargenine), nitrosoarginine (preferably N(G)-Nitrosoargenine), arginal, guanidino propionic acid, ε-N-methyllysine, allo-hydroxylysine, 2,3-diaminipropionic acid, 2,2'-diaminopimelic acid, ornithine, sym-dimethylarginine, asym-dimethylarginine, 2,6-diaminohexynoic acid, histidine, 1-methyl-histidine, 3-methyl-histidine, p-aminobenzoic acid, and 3-amino-tyrosine;

X$_3$ is a moiety having a net positive charge or a positively charged side chain under physiological conditions. Preferred residues X$_3$ are selected from the group including arginine, lysine, δ-hydroxylysine, homoarginine, 2,4-diaminobutyric acid, homoarginine, β-homoarginine, D-arginine, methylarginine (preferably alpha-N-methylarginine), nitroarginine (preferably N(G)-Nitroargenine), nitrosoarginine (preferably N(G)-Nitrosoargenine), arginal, guanidino propionic acid, ε-N-methyllysine, allo-hydroxylysine, 2,3-diaminipropionic acid, 2,2'-diaminopimelic acid, ornithine, sym-dimethylarginine, asym-dimethylarginine, 2,6-diaminohexynoic acid, histidine, 1-methyl-histidine, p-aminobenzoic acid, 3-methyl-histidine, and 3-amino-tyrosine;

$X_4$ is a neutral residue with a polar side chain, such as asparagine or citrulline, or a moiety having a net positive charge or a positively charged side chain under physiological conditions. Preferred residues $X_4$ are selected from the groups including asparagine, homoglutamine, cis-4-hydroxyproline, trans-4-hydroxyproline, cis-3-hydroxyproline, trans-3-hydroxyproline, citrulline, N-methylserine, N-methylglycine, dihydroxyphenylalanine, N-ethylasparagine, N-ethylglycine, homoserine, penicillamine, tetrahydropyranylglycine, allo-threonine, and 3,5-dinitrotyrosine as well as arginine, lysine, δ-hydroxylysine, homoarginine, 2,4-diaminobutyric acid, β-homoarginine, D-arginine, methylarginine (preferably alpha-N-methylarginine), nitroarginine (preferably N(G)-Nitroargenine), nitrosoarginine (preferably N(G)-Nitrosoargenine), arginal, guanidino propionic acid, ε-N-methyllysine, allo-hydroxylysine, 2,3-diaminipropionic acid, 2,2'-diaminopimelic acid, ornithine, sym-dimethylarginine, asym-dimethylarginine, 2,6-diaminohexynoic acid, histidine, p-aminobenzoic acid, 1-methyl-histidine, 3-methyl-histidine, and 3-amino-tyrosine;

$X_5$ is proline or a proline derivative, like cis-4-hydroxyproline, trans-4-hydroxyproline, cis-3-hydroxyproline, trans-3-hydroxyproline, β-cyclohexylalanine, 3,4-cis-methanoproline, 3,4-dehydroproline, homoproline or pseudoproline;

A neutral residue is defined as an amino acid residue having an uncharged side chain under physiological conditions. Physiological conditions are defined as pH 7.4, 37° C. and an osmotic pressure of 300 mosmol/kg. A polar side chain is defined as a side chain bearing at least one polar group (e.g. a hydroxyl, amino, amide or sulfhydryl group) that allows the formation of a hydrogen bond with another polar group. A proline derivative is a structure derived from proline containing a substituted or unsubstituted Pyrrolidine-ring. A moiety having a net positive charge or a positively charged side chain under physiological conditions is a basic amino acid residue. A hydrophobic moiety is a neutral residue without polar groups in the aliphatic or aromatic amino acid side chain, preferably being more hydrophobic than alanine.

$Sub_1$ being the free N-terminal amino group of the amino acid $X_1$ or a modification of the N-terminal amino group (replacing the N-terminal amino group of the amino acid $X_1$ sequence by $Sub_1$) with the general formula $NR_1R_2$. $Sub_1=NR_1R_2$, whereas $R_1$ and $R_2$ are independent from each other preferably selected from hydrogen or the groups consisting of:

(i) a straight chain, branched, cyclic or heterocyclic alkyl group, such as methyl, ethyl, n-propyl, isopropyl, n-butyl, isobutyl, cyclohexyl;
(ii) a straight chain, branched, cyclic or heterocyclic alkanoyl group, such as acetyl or methanoyl(formyl), propionyl, n-butyryl, isobutyryl, pentanoyl, hexanoyl, or cyclohexanoyl;
(iii) a reporter group, such as a fluorescent dye (e.g. fluorescein, Alexa488) or biotin;
(iv) together with $COR_3$ (see underneath) a linker bridging the N- and C-termini thereof to obtain a cyclic peptide, e.g. based on guanidine, ethyleneglycol oligomers, 2,4-diaminobutanoic acid, 2,3-diaminipropionic acid, 2,2'-diaminopimelic acid, desmosin, or isodesmosine.

$Sub_2$ being the free C-terminal carboxyl group of the C-terminal amino acid or a modification of the C-terminal carboxyl group, preferably with the general formula $COR_3$ ($R_3$ replacing the hydroxyl group of the last amino acid) $X_6$—$COR_3$ or $X_7$—$COR_3$ or $X_6X_7$—$COR_3$.

$COR_3$ is preferably selected from the group consisting of:

(i) carboxyl ($R_3$ being a free hydroxyl), an ester ($R_3$ being alkoxy), an amide ($R_3$ being an amine) or an imide;
(ii) together with $Sub_1$ a linker bridging the N- and C-termini thereof to obtain a cyclic peptide
(iii) $COR_3$ with $R_3$ being an additional amino acid residue selected from the group consisting of Pro, Ile, Leu, Arg, Val or $R_3$ being a peptide with, preferably two to three, amino acids containing at least one amino acid selected from the group consisting of Pro, Ile, Leu, Arg, Val substituted by a member of the group consisting of carboxyl ($R_3$ being a free hydroxyl), an ester ($R_3$ being an alcohol, such as methanol, ethanol, propanol, iso-propanol or butanol), an amide ($R_3$ being an amine) or an imide ($R_3$ being a alkyl amine or dialkylamine, such as methylamine, ethylamine, dimethyamine, or cyclohexylamine).
(iv) $COR_3$ with $R_3$ being an additional branched amino acid to form a dimeric or oligomeric structure, such as lysine, hydroxylysine, ornithine, 2,4-diaminobutanoic acid, 2,3-diaminopropionic acid, 2,2'-diaminopimelic acid, desmosin, isodesmosine or combinations of these branched amino acids.

In this way C-terminal peptide derivatives can be in particular formed as an ester ($R_3$=alkoxy), an amide ($R_3$=amide), an imide or an peptide elongated by additional amino acids selected from the group consisting of Pro, Ile, Arg, Val modified again at the C-terminal end as ester, amide, or imide. Further peptide derivatives can be formed by modifications at the N-terminal or C-terminal ends of the peptide. These changes can, for instance, be addition of an alkyl or alkanoyl group (either having a straight chain or being branched or cyclic or heterocyclic) or a guanidino group or addition of a macromolecule or a reporter moiety, either via a permanent linkage or a connection that can be cleaved under certain conditions (such as disulfide bridges or acid labile linkers).

All the natural amino acids, non natural amino acids or amino acid derivatives (like imino acids) forming the peptides or peptide derivatives of the invention can be either in the L- or D-configuration. However, if not otherwise specified, the amino acids building blocks in the sequences are preferably in the L-configuration.

$X_6$ and $X_7$ are optional additional residues. Thus in case $X_6$ and $X_7$ are absent, the last Proline (P) in the above mentioned sequence has a free C-terminal carboxyl group or is connected to $Sub_2$.

Thus in case a least one of the residues X6 and X7 are present, the peptide has for example one of the following general formula:

```
                                              (Formula 2)
Sub₁-X-N-X₂-X₃-P-V-Y-I-P-X₄-X₅-R-P-P-
H-P-X₆-X₇-COR₃ SEQ ID NO: 170

(Formula 3)
Sub₁-X₁-N-X₂-X₃-P-V-Y-I-P-X₄-X₅-R-P-
P-H-P-X₆-COR₃ SEQ ID NO: 171

(Formula 4)
Sub₁-Xi-N-X₂-X₃-P-V-Y-I-P-X₄-X₅-R-P-
P-H-P-X₇-COR₃ SEQ ID NO: 172
```

$X_6$ is selected from proline or a proline derivative or a moiety having a net positive charge or a positively charged side chain under physiological conditions. Preferred residues $X_6$ are selected from the groups including pro line, cis-4-hydroxyproline, trans-4-hydroxyproline, cis-3-hydroxyproline, trans-3-hydroxyproline, β-cyclohexylalanine, 3,4-cis-methanoproline, 3,4-dehydroproline, homoproline, pseudoproline as well as arginine, preferably D-arginine, δ-hydroxylysine, homoarginine, 2,4-diaminobutyric acid, β-homoarginine, ε-N-methyllysine, allo-hydroxylysine, 2,3-diaminipropionic acid, 2,2'-diaminopimelic acid, lysine, arginine, ornithine, methylarginine (preferably alpha-N-methylarginine), nitroarginine (preferably N(G)-Nitroargenine), nitrosoarginine (preferably N(G)-Nitrosoargenine), arginal, guanidino propionic acid, sym-dimethylarginine, asym-dimethylarginine, 2,6-diaminohexynoic acid, histidine, 1-methyl-histidine, 3-methyl-histidine, or 3-amino-tyrosine.

$X_7$ is selected from proline or proline derivatives, a polar moiety (such as serine) or a hydrophobic moiety. Preferred residues $X_7$ are selected from the groups including proline, cis-4-hydroxyproline, trans-4-hydroxyproline, cis-3-hydroxyproline, trans-3-hydroxyproline, β-cyclohexylalanine, 3,4-cis-methanoproline, 3,4-dehydroproline, homoproline or pseudoproline, serine, threonine, δ-hydroxylysine, citrulline, homoserine, or allo-threonine as well as phenylalanine, N-methyl-leucine, leucine, isoleucine, valine, methionine, tert.-butyl glycine, cyclohexylalanine, alanine, β-alanine, 1-amino-cylcohexyl carbonic acid, N-methyl-isoleucine, norleucine, norvaline, N-methylvaline, or a short peptide sequence, with preferably one to 3 residues, preferably selected of proline, isoleucine or any of the before mentioned moieties, or a branched linker containing several peptide units, such as lysine, hydroxylysine, ornithine, 2,4-diaminobutanoic acid, 2,3-diaminopropionic acid, 2,2'-diaminopimelic acid, desmosin, isodesmosine, The C-terminal amino acid is for example the last proline (P) in Formula 1, $X_6$ (in Formula 3) or $X_7$ (in Formula 2 and 4).

The natural sequences with the unmodified apidaecin 1a and 1b according to SEQ ID No. 1 (GNNRPVYIPQPRPPH-PRI-OH) and SEQ ID No. 2 (GNNRPVYIPQPRPPHPRL-OH) in which OH is standing for a free carboxyl group at the C-terminus ($Sub_1$=$NH_2$ and $Sub_2$=RI—OH or RL-OH, $R_3$=—OH), are excluded from the scope of the invention.

The peptides or peptide derivatives according to the invention possess at least one of the following advantages compared to the natural occurring apidaecin peptides:
  (i) an increased half-live in mammalian serum due to a higher protease resistance and
  (ii) an increased antimicrobial activity against one or several bacterial strains, especially human pathogens, or fungus or other microbial infections and
  (iii) the peptides are not toxic to human cells including erythrocytes.

Examples of peptides and peptide derivatives according to the invention have the sequences according to SEQ ID No. 3 to 121 as well as 122 to 159 (see also Table 2 in example 1). Less preferred are the peptides and peptide derivatives according to SEQ ID No. 92, 141 and 142 (see also Table 2 in example 1).

The peptides and/or multimeric peptide constructs of this invention, which are modified to improve the antimicrobial or antifungal activity and to extend the activity spectrum to other bacteria or fungi and to improve the stability against proteases and peptidases, are characterized by the high antibacterial and/or antifungal potency and good metabolic stability in mammalian serum.

Appropriate modifications in positions 3 ($X_2$), 4 ($X_3$), and 10 ($X_4$) improve the antibacterial activity of the wild-type apidaecin sequence against different bacteria, as discussed below and shown in the examples.

The first positions ($Sub_1$, $X_1$, $X_2$ and $X_3$) are assumed to be responsible for a better transport through the membrane into the cell whereas position 10 ($X_4$) might also contribute to inhibition of an intracellular target. Moreover, residue $X_2$ can further stabilize the N-terminal peptide sequence against degradation and thereby increase the half life in serum.

Preferred examples according to the invention are the sequences with a positively charged residues $X_4$ (position 10), like the sequences selected from the sequences according to SEQ ID No. 9 to 18, 20 to 25, 27 to 31, 34 to 40, 45 to 49, 55 and 56, 64 to 69, 81 to 83, 86 to 91, 97 to 100, 102 to 104, 112, 113, 117, 119, 122 to 128, 131, 134, 137, 138, 145 to 147 and 150 to 159. Less preferred are sequences with a Glutamine (Q) at $X_4$ (position 10).

Preferred examples according to the invention are the sequences with positively charged residues as $X_3$ (position 4), like the sequences selected from the sequences according to SEQ ID No. 10, 68, 95, 97, 100, 122 to 131, 134, 137 and 155.

Moreover, the free N-terminal amino group and C-terminal carboxyl group are preferably modified, as these termini are prone to peptidase and protease degradation in serum, body fluids in general, tissues, organs, or cells, and appear to be very critical for the antibiotic activity of the peptides, peptide derivatives and multimers thereof. Increasing the protease resistance increases the half-life of the peptide in the serum. Additionally, modification of the termini also allows for coupling of the peptide to other moieties, such as other amino acid sequences (thereby possibly creating multimeric peptides or proteins), or other biomolecules which can function as carrier or label. In a specific embodiment the carrier molecule also functions as a targeting molecule, which is able to localize the bacterial infection and can bind to the bacterium, in order to bring the antibiotic compound in the vicinity of the (bacterial) cell to attack or even transport it through the bacterial membrane into the bacterial cell. Such targeting moieties can be molecules which are known to bind to the lipopolysaccharide (LPS) molecules, which form the outside of Gram-negative bacteria. Known compounds for this use are, for instance, anchor peptides, such as the AcmA motif of Lactobacillus, or antibodies directed to lipopolysaccharide. The latter are preferred since they also have an intrinsic antibiotic effect and thus could be used for enhancing the action of the peptide of the invention.

As the N-terminal amino acid, that is $Sub_1$-$X_1$, it is very advantageous to have a moiety which has a positive charge under physiological circumstances, i.e. in the (human) body. Physiological circumstances thus mean a pH of about 6-8 and a temperature of about 30-40° C. This positive charge either in $Sub_1$ or $X_1$ in the peptide or peptide-derivative is most likely necessary for the antibacterial function.

One example to achieve a N-terminal stabilization against proteolytic cleavage is acylation ($Sub_1$=Acyl-NH—), like acetylation ($Sub_1$=Acetyl-NH—) of the α-amino group of a positively charged amino acid, like ornithine or lysine ($Sub_1$-$X_1$=Acyl-Orn or Acyl-Lys). This acylation (preferably acetylation) does leave the positive charge on the side chain of the amino acid intact.

Another example to achieve a N-terminal stabilization against proteolytic cleavage is guanidination (with preferably $Sub_1$=N(CH$_3$)$_2$—(C—N$^+$(CH$_3$)$_2$)—NH—), which introduces at the same time a positively charged group on position 1.

More preferred examples according to the invention are the sequences with positively charged residues as $X_1$ and $X_4$ (position 1 and 10), like the sequences selected from the sequences according to SEQ ID No. 12 and 13, 16, 18, 21 to 24, 27 to 30, 35 to 40, 64, 65, 66, 81-83, 86-88, 112, 113, 117, 119, 124 to 128, 131, 134 and 137.

Further preferred examples according to the invention are the sequences with proline, a proline derivative or a positively charged residue as $X_6$ (position 17), like the sequences selected from the sequences according to SEQ ID No. 10, 23, 24, 27, 28, 70, 109 to 113, 121, 127, 128, 131-134, 136, 138, 139, 145, 146 and 148-155.

Other preferred examples according to the invention are the sequences with proline, a proline derivative, a polar moiety or a hydrophobic moiety as $X_7$ (position 18) like the sequences selected from the sequences according to SEQ ID No. 10, 24, 27-37, 42, 44, 46, 47, 68 to 77, 83, 93, 94, 96, 107-110, 114, 115 and 126, 144.

Very preferred examples are peptides with a positive charged amino acid in position 1 ($X_1$) or 10 ($X_4$) (like Ornithine, Arginine or Lysine) and an modified C-Terminus, in particular the peptides according to SEQ ID No. 7 to 8, 11 to 13, 20, 21, 22, 25, 38 to 40, 45, 65 to 67, 131, 134 and 137.

Most preferred peptides contain ornithine in position 1 (residue $X_1$), arginine in position 10 (residue $X_4$), proline or hydroxyproline in position 11 (residue $X_5$), arginine or a derivative thereof (like ornithine, homoarginine) in position 17 (residue $X_6$ in $Sub_2$) and an acetylated or guandidated N-terminus, such as SEQ ID No. 40, 88, 131, 134 and 137.

From the examples it can be seen that already a small modification of the C-terminus to an amide ($Sub_2$=—$NH_2$) improves the inhibitory effect against *E. coli* and *S. typhi* significantly. Preferred sequences with an amide as C-terminus are SEQ ID No. 4, 6, 7, 8, 14, 20, 38, 39 and 134.

Also preferred are modifications, such as methyl, propyl, amide, and proline, at position(s) 17 ($X_6$) and/or 18 ($X_7$) and/or the C-terminus ($Sub_2$) to reduce C-terminal degradation. From the experimental results it can be gleaned that apparently the amino acids at positions 17 and 18 are also very critical for antibiotic action, since single amino acid replacement at these positions by alanine abolished the efficacy with respect to wild-type apidaecin antibiotic activity.

Most preferred examples according to the invention are peptides, which fulfill all the advantages:
  (i) an increased half-live in mammalian serum due to a higher protease resistance and
  (ii) an increased antimicrobial activity against one or several bacterial strains, especially human pathogens, or fungus or other microbial infections and
  (iii) the peptides are not toxic to human cells including erythrocytes.

The action of antimicrobial peptides is very complex, as they have to penetrate the bacterial cell membrane and enter the cytoplasm to inhibit specifically an intracellular bacterial target without being toxic to mammalian cells and blood cells. Another important point to address is the stability of the peptides or peptide derivatives against degradation by peptidases or proteases. Thus the ideal peptide has high antibacterial activity (low MIC values), no cellular toxicity, not hemolytic activity, and a half-life in blood of several hours. Relative to the native apidaecin sequences the best peptide derivatives described in this invention have a more than tenfold increased antimicrobial activity. This was partially achieved by amidation of C-terminus and substitution of Gln in position 10 ($X_4$) by a basic residue, most favorably argenine or ornithine. As the half-life of these peptides if relatively short in serum, the N-terminus is preferably modified (formylated, acetylated or guanidated) to reduce degradation by aminopeptidases or aminoproteases. At the N-terminus a positive charge is preferred in order to achieve a good antibacterial activity. The glycine in position 1 ($X_1$) of the native apidaecin sequence is preferably replaced by a basic residue like arginine, lysine or ornithine, most favorably by ornithine, as its C-terminal peptide bond is not cleaved by trypsin and related enzymes. For the same reason Arg-17 ($X_6$) of the native apidaecin sequence is preferably substituted to reduce cleavage of the peptide bond between Arg-17 ($X_6$) and Leu/Ile-18 ($X_7$) by endoproteases. Examples are substitution of Arg-17 ($X_6$) by ornithine or N-methylation of Leu-18 ($X_7$) that both increased the serum stability more than 24 times from a half-time of 15 min to more than 360 min. Although none of the peptides is toxic to COS-7 cell lines or red blood cells, substitution of Pro-11 ($X_5$) by trans-4-Hyp has the potential to further reduce possible site effects, as polar substitutions reduce the tendency of peptides or peptide derivatives to bind to mammalian cell membranes without reducing the antibacterial activity.

Advantageously, the peptides or peptide derivatives according to the invention do not induce resistance or induce less resistance than the wild type peptides.

Advantageously, a number of peptides or peptide derivatives according to the invention show an enlarged spectrum of antimicrobial activity, showing an activity against bacteria like *Baccilus subtilis* and *Mycobacterium vaccae*, which is not observed for the native wt apidaecin peptides. The common feature of these sequences with activity against *B. subtilis* is a positively charged N-terminus. The common feature of these sequences with activity against *M. vaccae* is a positively charged N-terminus, a charged residue (preferably arginine or ornithine) as $X_4$ (position 10) and a charged residue (preferably ornithine) as $X_1$ (position 1). Examples of these preferred sequences are selected from SEQ ID No. 65, 83, 131 and 155.

The term "peptide" as used herein means a sequence of amino acids coupled by a peptide bond, wherein the amino acids are preferably one of the twenty naturally peptide-building amino acids and wherein the amino acids can be in the L-configuration or in the D-configuration, or, for isoleucine and threonine in the D-allo configuration (only inversion at one of the chiral centers).

The term peptide derivative (or peptidomimetics) according to the invention does not only include peptides, which are modified, e.g. on the N- or C-terminus by the above mentioned groups $Sub_1$ and $Sub_2$. It further comprises peptides are altered by substitutions and/or modifications of one or more of the amino acid residues by chemical moieties other than natural protein-building amino acid residues, such as non-proteinogenic α-amino acids, β-amino acids, or peptides with an altered backbone. Altered back bone meaning at least one peptide bond has been replaced by e.g. a non-cleavable bond like a reduced amide bond, an alkylated amide bond, or a thioamide bond.

Also comprised are moieties that can form a covalent bond with both the COOH-group of the preceding amino acid residue and the $NH_2$-group of the following amino acid residue, and which thus not necessarily need to maintain the peptide backbone structure, such as sugar amino acid dipeptide isosters, azapeptides, 6-homopolymers, y-peptides, Y-lactam analogues, oligo(phenylene ethylene)s, vinylogous sulfonopeptides, poly-N-substituted glycines, or oligocarbamates. These modifications are preferred at positions prone to enzymatic degradation, especially at the three N-terminal residues (positions 1 to 3—$X_1$—N—$X_2$) and the two C-terminal residues (after position 16—$X_6$—$X_7$). Thus, preferably at least one of the bonds between $X_1$—N (e.g., Gly-Asn), N—$X_2$ (e.g., Asn-Asn), $X_2$—$X_3$ (e.g., Asn-Arg), $X_6$—$X_7$ (e.g. Arg-Leu or Arg-Ile) is a non-cleavable bond.

This non-cleavable bond is defined as a bond, which is not susceptible to cleavage by proteases and is preferably selected from the group consisting of a reduced amide bond, alkylated amide bond, or a thioamide bond. A reduced amide bond is a peptide bond, in which the carbonyl moiety (C=O)

is either reduced to a hydroxyl moiety (HCOH) or a methylene moiety ($CH_2$). An alkylated amide bond is a peptide bond in which either the nitrogen (N-alpha) or the carbon (C-alpha) is substituted with alkyl, preferably with 1 to 3 C-atoms, a preferred example being N-methylation.

The peptide or peptide derivative according to the invention can be linear, i.e. wherein the first and last amino acid of the sequence have a free $NH_2$— and COOH-group or are modified by $Sub_1$ and $Sub_2$ respectively, or they may be cyclic, i.e. when the first and the last amino acid are coupled by a peptide bond or a linker.

Further objects of the invention are methods to produce the above-mentioned novel antibiotic compounds.

The peptides or peptide derivatives of the invention can be produced synthetically or, where applicable, recombinantly by conventional methods. Specific embodiments of apidaecin-derived antibiotic peptides or peptide derivatives are disclosed in detail in the experimental part below. Preferably, the peptides or peptide derivatives of the invention are prepared conventionally by known chemical synthesis techniques, such as, for instance, are disclosed by Merrifield [23].

Alternatively, the peptides of the invention may be produced by recombinant DNA techniques by cloning and expressing within a host microorganism or cell a DNA fragment carrying a nucleic acid sequence encoding one of the above-described peptides. Nucleic acid coding sequences can be prepared synthetically [24], or may be derived from existing nucleic acid sequences (e.g. the sequence coding for wild-type apidaecin) by site-directed mutagenesis. The so prepared coding sequences can be amplified from RNA (or DNA) using accordingly designed primers in a polymerase chain reaction (PCR) by known techniques. After purification by agarose gel electrophoresis for example, the PCR product is ligated in a vector, and in a host cell finally transformed with the appropriate recombinant plasmid. Various host cells are well known in recombinant technology, such as *E. coli, Bacillus, Lactobacillus, Streptomyces*, mammalian cells (e.g. Chinese Hamster ovary cells (CHO) or COS-1 cells), yeasts (e.g. *Saccharomyces, Schizophyllum*), insect cells or viral expression systems (e.g. baculovirus systems). The selection of other suitable host cells and methods for transformation, culture, amplification, screening, product production and purification can be performed by one of skill in the art by reference to known techniques [25]. When produced by conventional recombinant means, the peptides of this invention may be isolated either from the host cell by conventional lysis techniques or from cell medium by conventional methods, such as liquid chromatography, preferably affinity chromatography. The antimicrobial peptide can be expressed as a single peptide, or an oligomer of several peptide sequences combined either N- or C-terminally, or even an N- or C-terminal tag to allow easier purification of the recombinant peptide or protein constructs. Conventional molecular biology techniques and site-directed mutagenesis may be further employed to modify the sequences and provide desired non-native peptide sequences. All these recombinant techniques are known to the skilled person and have been reported for many antimicrobial peptides including apideacin [26], perinerin [27], and defensin [28].

It is also possible to include non-naturally occurring amino acids in peptides through genetic engineering techniques. This has been extensively described by Noren et al. and Ellman et al. [29, 30].

Subsequently, the peptide can be isolated from the culture of the host cells or the in-vitro translation system. This can be achieved by common protein purification and isolation techniques which are state of the art. Such techniques may for example involve immuno-adsorption or -chromatography. It is also possible to provide the peptides with a tag (such as a histidine tag) during synthesis, which allows for a rapid binding and purification, after which the tag is enzymatically removed to obtain the active peptide.

If the peptide itself cannot be encoded or expressed but is very similar to a peptide that can be encoded or expressed, the method can be applied to prepare the peptide to which the peptide is similar, followed by one or more steps in which said peptide is modified by chemical or enzymatic techniques to prepare the final peptide or peptidomimetic. Some more comprehensive summaries of methods which can be applied in the preparation of the peptides are described in the literature [31, 32, 33, 34, 35].

The peptides and peptide derivatives of the invention can be used alone, or in combination, or in the form of multimers or in the form of branched multimers. Suitable combinations of peptides of the invention comprise concatemers of peptides of the invention serially coupled to each other via spacers, for instance in the form of a peptide dimer, a peptide trimer, etc., wherein the individual peptides are subsequently aligned. This multimer can be composed by peptides and peptide-derivatives with identical sequences or of several of the sequences according to formula 1.

Single peptide or peptide-derivatives can be coupled to a biocompatible protein, such as human serum albumin, humanized antibody, liposome, micelle, synthetic polymer, nanoparticle, and phage. Alternatively, multimers of individually combined peptides or peptide derivatives of the invention are prepared in the form of dendrimers, or clusters, wherein three or more peptides are linked to one common centre.

In one embodiment, multiple peptides or peptide derivatives of the formula 1 described above are organized in multimeric constructs or compositions. For example, optional amino acids (e.g., -Gly-Ser-) or other amino acid or chemical compound spacers are included at the N- or C-termini of the peptides for the purpose of linking two or more peptides together or to a carrier. This composition may take the form of one or more of the above-described peptides expressed as a synthetic peptide coupled to a carrier protein. Alternatively, a composition contains multiple peptides, each expressed as a multiple antigenic peptide, optionally coupled to a carrier protein. Alternatively, the selected peptides are linked sequentially and expressed as a recombinantly produced protein or polypeptide. As one embodiment, multiple peptides are linked sequentially, with or without spacer amino acids between, to form a larger recombinant protein. Alternatively, the recombinant protein can be fused in frame with a carrier protein.

In another embodiment the multimeric construct contains at least two of the above-defined peptides (which may be the same or different peptides of the formula 1), one peptide is attached to any amino acid of the other peptide(s). Any number of additional peptides may be attached to any amino acid of the other peptides in the composition. In another embodiment of a multimeric composition containing at least two peptides, the second or additional peptides are attached to a branched construct of the other peptides in the composition. Alternatively, each additional peptide is covalently linked to $Sub_1$ or $Sub_2$ of another peptide in the composition.

In another embodiment of a multimeric construct or composition containing at least two of the peptides, at least one or more of the peptides are attached to a carrier. In another embodiment, one or more of said peptides is a synthetic peptide fused to a carrier protein. Still alternatively multiple of the above-described peptides with or without flanking sequences, may be combined sequentially in a polypeptide. The peptides or this polypeptide are either coupled to the same carrier, or different peptides may be coupled individually as peptides to the same or different immunologically inert carrier proteins.

Suitable carriers may enhance stability or delivery, improve the production, or change the activity spectrum of the peptide. Examples for carriers are human albumin, polyethylene glycol, other biopolymers or other naturally or non-naturally occurring polymers. In one embodiment, the moiety is desirably a protein or other molecule which can enhance the stability of the peptide. One of skill in the art can readily select an appropriate conjugation moiety.

Preferred examples of a multimeric composition according to this invention have the structure (Ac-OrnAsnAsnArgProValTyrIleProArgProArgProProHisProArgLeu)$_2$-Dab and (OrnAsnAsnArgProValTyrIleProArg-ProArgProProHisProArgLeu)$_2$-Dab corresponding to SEQ ID No. 83 and 119.

Further preferred dimers are selected from:

| SEQ ID No. | Sequence/Structure |
| --- | --- |
| 124 | (Ac-ONNRPVYIPRPRPPHPRL)$_2$-Dab |
| 125 | (Guan-ONNRPVYIPRPRPPHPRL)$_2$-Dab |
| 127 | (Ac-ONNRPVYIPRPRPPHPOL)$_2$-Dab |
| 128 | (Guan-ONNRPVYIPRPRPPHPOL)$_2$-Dab |
| 129 | (Ac-GNNRPVYIPQPRPPHPRL)$_2$-Dab |
| 130 | (Guan-GNNRPVYIPQPRPPHPRL)$_2$-Dab |

In yet another embodiment, the peptides are in the form of a multiple antigenic peptide ("MAP"), which can e.g. be designed according to the "MAP-system" as described by Tam et al. [36]. This system makes use of a core matrix of lysine residues onto which multiple copies of the same peptide of the invention are synthesized as described [see, e.g., 37]. Each MAP contains multiple copies of one or more of the peptides of this invention. One embodiment of a MAP contains at least three, and preferably four or more peptides. One of skill in the art may readily make any number of multimeric constructs from the peptides of the formula identified above with resort to only conventional skills and knowledge in light of this specification. All such multimeric compositions and constructs are intended to be included in this invention.

Yet other combinations in the form of multimers are formed by beads on the surface of which the peptides or peptidomimetics of the invention are exposed. The bead may then function as a carrier for the peptide or peptidomimetic, and may similarly function as a detectable label. Multimers can, for example, be prepared by biotinylating the N-terminus of peptide or peptidomimetic chains and subsequent complexation with streptavidin. As streptavidin is able to bind four biotin molecules or conjugates with high affinity, very stable tetrameric peptide complexes can be formed by this method. Multimers may be composed of identical or different peptides or peptidomimetics according to the invention. Preferably, however, the multimers of the invention are composed of two or more peptides or peptidomimetics, in which each component constitutes to one asset of the total biocidal activity (targeting, antimicrobial activity, scavenging).

An other objective of the invention is the use of the inventive peptides or peptide derivatives in medicine or pharmacy, e.g. for antibiotic therapy or in an antimicrobial (in particular bactericidal) composition.

A further object of the invention are pharmaceutical compositions comprising one or more of the peptides or peptides derivatives of the invention or multimeric constructs, whether or not in the presence of other pharmaceutically active compounds.

Also part of the invention is the use of a peptide according to the invention as a pharmaceutical and/or for the preparation of a drug which can be used as an antibiotic.

The peptides may be employed in pharmaceutical compositions individually. Alternatively, for the purposes of enhancing pharmacokinetics or bioavailability without eliciting immune responses, one or more peptides are fused or conjugated to other moieties as described above. Any number of single peptides or multimeric constructs may be mixed together to form a single composition.

A pharmaceutical composition of the invention comprises a therapeutically effective amount of one or more peptides or peptide derivatives of the present invention. Once formulated, the pharmaceutical compositions of the invention can be administered directly to the subject in a method of treating microbial (in particular bacterial) infection comprising administering to a subject in need thereof a therapeutically effective amount of the composition of the invention.

The compositions of this invention are designed to treat infections by the selected bacterium or fungus of an infected mammal, e.g., human. At least one, or alternatively, several of the peptides or multimeric constructs of the present invention may be formulated into an antimicrobial (in particular antibacterial or anti-fungal) composition with a pharmaceutically acceptable carrier and other optional components. For use in such compositions, the selected peptide may be produced preferably synthetically, but also recombinantly, as disclosed above.

Direct delivery of the compositions will generally be accomplished by topical application or other forms of administration, either orally, parenterally, subcutaneously, sublingually, intralesionally, intraperitoneally, intravenously or intramuscularly, pulmonarily, or delivered to the interstitial space of a tissue.

The pharmaceutical composition may also comprise a suitable pharmaceutically acceptable carrier or diluent and may be in the form of a capsule, tablet, lozenge, dragee, pill, droplet, suppository, powder, spray, vaccine, ointment, paste, cream, inhalant, patch, aerosol, and the like. As pharmaceutically acceptable carrier, any solvent, diluent or other liquid vehicle, dispersion or suspension aid, surface active agent, isotonic agent, thickening or emulsifying agent, preservative, encapsulating agent, solid binder or lubricant can be used which is most suited for a particular dosage form and which is compatible with the peptide, peptidomimetics (peptide derivative), peptide-conjugate or peptidomimetics-conjugate.

The pharmaceutical composition thus preferably contains a pharmaceutically acceptable carrier. The term "pharmaceutically acceptable carrier" also includes a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable pharmaceutically acceptable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Salts of peptides or functional equivalents are prepared by known methods, which typically involve the mixing of the peptide or peptidomimetic or peptide-conjugate or peptidomimetics-conjugate with either a pharmaceutically acceptable acid to form an acid addition salt, or with a pharmaceutically acceptable base to form a base addition salt. Whether an acid or a base is pharmaceutically acceptable can be easily decided by a person skilled in the art after taking the specific intended use of the compound into consideration. For instance, not all acids and bases that are acceptable for ex vivo applications can be used for therapeutic compositions. Depending on the intended use, pharmaceutically acceptable acids include organic and inorganic acids such as formic acid, acetic acid, propionic acid, lactic acid, glycolic acid, oxalic acid, pyruvic acid, succinic acid, maleic acid, malonic acid, cinnamic acid, sulfuric acid, hydrochloric acid, hydrobromic acid, nitric acid, perchloric acid, phosphoric acid, and thiocyanic acid, which form ammonium salts with free amino groups of peptides and functional equivalents. Pharmaceutically acceptable bases, which form carboxylate salts with free carboxylic groups of peptides and functional equivalents, include ethylamine, methylamine, dimethylamine, triethylamine, isopropylamine, diisopropylamine, and other mono-, di- and trialkylamines, as well as arylamines. Moreover, also pharmaceutically acceptable solvates are encompassed.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable recipients is available in Remington's Pharmaceutical Sciences (Mack Pub. Co., N.J., 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

For therapeutic treatment peptide, peptide-derivative, peptide-conjugate or peptide-derivative-conjugate may be produced as described above and applied to the subject in need thereof. The peptide peptide-derivative, peptide-conjugate or peptide-derivative-conjugate may be administered to a subject by any suitable route, preferably in the form of a pharmaceutical composition adapted to such a route and in a dosage which is effective for the intended treatment.

Pharmaceutical compositions of this invention may contain other active agents, such as conventional antibiotics (like e.g. vancomycin, streptomycin, tetracyclin, penicillin) or other antimicrobial compounds, such as antifungals, e.g. itraconazole or myconazole. Also compounds which alleviate other infection symptoms, such as fever (e.g. salicylic acid) or skin rash may be added.

Next to therapeutic use for treatment of infections, also in biological warfare, it is also possible to use the peptides or peptide derivatives of the invention in a disinfecting or cleaning agent (e.g., a bactericidal composition), which can be used to disinfect or clean surfaces and/or equipment. Another field of application is in packaging, where peptides can be linked to or embedded in packaging material or as a preserving agent for other material which is easily degradable by micro-organisms. The peptides or peptide derivatives of the invention are specifically usable for packaging of food, since they are not toxic upon contact or ingestion.

Another part of the invention provides a method of treating a mammalian microbial (in particular bacterial or fungal) infection comprising administering to a mammal having said infection an effective an antimicrobial amount of a pharmaceutical composition described herein.

The term "therapeutically effective amount" as used herein refers to an amount of a therapeutic, that is a peptide, peptidomimetic, peptide-conjugate, or peptidomimetic-conjugate according to the present invention, to reduce or prevent growth and colonization of bacteria, or to exhibit a detectable therapeutic or prophylactic effect. The effect can be detected by, for example, culturing biopsies and assaying for bacterial activity or by any other suitable method of assessing the progress or severity of bacterial infection. The precise effective amount for a subject will depend upon the subject's size and health, the nature and extent of the condition, and the therapeutics or combination of therapeutics selected for administration. Specifically, the compositions of the present invention can be used to reduce or prevent bacterial infection and/or accompanying biological or physical manifestations, such as reduction of fever. Methods that permit the clinician to establish initial dosages are known in the art. The dosages determined to be administered must be safe and efficacious.

The amount of the protein, peptide or nucleic acid sequences of the invention present in each antibacterial effective dose is selected with regard to consideration of the pathogen causing the infection, the severity of infection, the patient's age, weight, sex, general physical condition and the like. The amount of active component required to induce an effective anti-bacterial or anti-fungal effect without significant adverse side effects varies depending upon the pharmaceutical composition employed and the optional presence of other components, e.g., antibiotics, antifungals and the like. For purposes of the present invention, an effective dose will be from about 0.01 µg/kg to 50 mg/kg, preferably 0.5 µg/kg to about 10 mg/kg of the peptide, peptidomimetic, peptide-conjugate, or peptidomimetic-conjugate in the individual to which it is administered.

Initial doses of the peptides, peptidomimetics, multimers, or peptide-conjugates, peptide-mimetics-conjugates of this invention are optionally followed by repeated administration. Dosage frequency depends upon the factors identified above, and preferably ranges from 1 to 6 doses per day for a duration of about 3 days to a maximum of about 1 week.

Yet in another alternative embodiment, the peptide or peptidomimetic or peptide-conjugate or peptidomimetic-conjugate or compositions of the invention are administered from a controlled or sustained release matrix inserted in the body of the subject.

In one embodiment a compound of the invention is administered in a transmucosal dosage form. This route of administration is non-invasive and patient-friendly; at the same time it probably leads to an improved bioavailability of the compound compared to oral administration, especially if the compound is not stable in the fluids of the digestive system, or if it is too large to be absorbed from the gut effectively. Transmucosal administration is possible, for instance, via nasal, buccal, sublingual, gingival, or vaginal dosage forms. These dosage forms can be prepared by known techniques; they can be formulated to represent nasal drops or sprays, inserts, films, patches, gels, ointments, or tablets. Preferably, the excipients used for a transmucosal dosage form include one or more substances providing for mucoad-hesion, thus prolonging the contact time of the dosage form with the site of absorption and thereby potentially increasing the extent of absorption.

In a further embodiment, the compounds are administered via the pulmonary route, using a metered dose inhaler, a nebulizer, an aerosol spray, or a dry powder inhaler. Appropriate formulations can be prepared by known methods and techniques. Transdermal, rectal, or ocular administration may also be feasible in some cases.

It can be advantageous to use advanced drug delivery or targeting methods to deliver a compound of the invention more effectively. For instance, if a non-parenteral route of administration is chosen, an appropriate dosage form may contain a bioavailability enhancing agent, which may be any substance or mixture of substances which increases the availability of the compound. This is achieved, for instance, by the protection of the compound from degradation, such as by an enzyme inhibitor or an antioxidant. More preferably, the enhancing agent increases the bioavailability of the compound by increasing the permeability of the absorption barrier, which is typically a mucosa. Permeation enhancers can act via various mechanisms; some increase the fluidity of mucosal membranes, while others open or widen the gap junctions between mucosal cells. Still others reduce the viscosity of the mucus covering the mucosal cell layer. Among the preferred bioavailability enhancers are amphiphilic substances such as cholic acid derivatives, phospholipids, ethanol, fatty acids, oleic acid, fatty acid derivatives, EDTA, carbomers, polycarbophil, and chitosan.

Indications for which the peptides, peptide derivatives, conjugates, or multimers of the invention can be used are bacterial infections by both Gram-positive and Gram-negative bacteria, such as *Escherichia coli, Enterobacter cloacae, Erwinia amylovora, Klebsiella pneumoniae, Morganella morganii, Salmonella typhimurium, Salmonella typhi, Shigella dysenteriae, Yersinia enterocolitica, Acinetobacter calcoaceticus, Agrobacterium tumefaciens, Francisella tularensis, Legionella pneumophila, Pseudomonas syringae, Rhizobium meliloti, Haemophilus influenzae.*

Another object of the invention is the use of a peptide or peptide derivative or a mulitmer according to the invention in biotechnical or pharmaceutical research or in a screening assay, in particular for identifying a compound, which has a potential bactericidal or antifungal effect.

In this respect the invention provides a method for identifying a compound, which has a potential antibactericial or antifungial effect, comprising:
  (i) performing a competitive assay with:
    (a) a microorganism susceptible to a peptide or peptide derivative or multimer according to the invention,
    (b) a peptide or peptide derivative or multimer according to the invention,
    (c) at least one compound to be tested;
    by exposing (a) to (b) and (c); and
  (ii) selecting a test compound which competitively displaces the binding of the peptide or peptide derivative or multimer to the microorganism.

This screening method identifies test compounds which compete with the peptides, peptide derivatives or multimeric compositions of this invention for binding to the unknown receptor on the pathogen. Thus small molecules specifically binding to the same site targeted by the peptide can be effectively identified in a high-throughput screening. Thereby, the test compounds posses most likely same mode of action as the original peptide sequence and thus will be active also against multiresistent microbes killed by apidaecin or one of its analogs described in this invention.

This screening method is carried out by known means, however using at least one peptide or peptide derivative or multimer according to the invention. In one embodiment the peptide or peptide derivative or multimer is labeled with a fluorescent, radioactive or other marker and the binding of the labeled peptide or peptide derivative or multimer to the microorganism is detected and compared in presence or absence of the substance(s) to be tested.

Preferably thereafter, the test compounds, which compete with the peptides or multimeric constructs of this invention for binding to the receptor are identified and screened for anti-bacterial or antifungal use.

In one embodiment the bimolecular fluorescence complementation (BIFC) method is used in the competitive assay. This method enables the direct visualization of intracellular protein interactions, which was exemplified for the interaction of the SH3 domain from the c-Abl tyrosine kinase with both natural and designed targets in *E. coli* [38]. The assay is sensitive enough to enable the detection of interactions between proteins that are poorly expressed in bacteria. It bases on the association of two fragments of the functional yellow fluorescent protein (YFP) after the SH3 domain bound to its partner. Once these two proteins bind to each other, the two fragments of YFP form a complex very similar to the structure of the native protein. This can be monitored by the obtained fluorescence of the YFP complex, as the individual fragments do not show any fluorescence activity. A similar construct can be designed to screen for compounds competing with the peptides and peptide derivatives described in this invention. A high-throughput screening can be easily adapted to 386-well microtiter plates by one of skill in the art.

In another embodiment the peptides are employed in a suitable competitive assay method with test compounds to assess the ability of the test compound to competitively displace the peptide from binding to its presently unknown receptor on the pathogen. Where desired, and depending on the assay selected, a microorganism (e.g., bacterium, virus or fungus) to which the selected peptide(s) are known to bind, e.g., *E. coli* or *K. pneumoniae* strains, may be immobilized directly or indirectly on a suitable surface, e.g., in an ELISA format. Such immobilization surfaces are well known. For example, an inert bead may be used. Further, the ligand may be bound to a 96 well plate. Thereafter selected amounts of the test compounds and the peptides of this invention are exposed to the immobilized microorganism and those test compounds selected which can compete with the peptides for binding to the immobilized microorganism. Once those test compounds, which compete with the peptides for binding to the receptor on the bacteria or fungi are identified, they may be further screened for antibacterial or anti-fungal activities in the methods described in the examples below.

In yet a further aspect, the invention provides an isolated nucleic acid molecule comprising a nucleotide sequence encoding a peptide or multimer according to the invention. The nucleic acid encodes the anti-bacterial or anti-fungal peptide or multimeric compositions of the invention in operative association with a regulatory sequence directing the expression thereof in a host cell. In yet another aspect, the invention provides a host cell transfected or transformed with the above-described nucleic acid molecule.

The invention is illustrated by the following examples without being limited to these:

EXAMPLE 1

Solid Phase Peptide Synthesis

All peptides and peptide derivatives were synthesized by conventional solid-phase peptide synthesis using the Fmoc/

'Bu-strategy [39]. Amino acid derivatives were from Multi-SynTech GmbH (Witten, Germany). Peptides and peptide derivatives with a free C-terminus (COOH-group) were synthesized on polystyrene-based wang resin (loading capacity 1.33 mmol/g) from Merck Biosciences (Schwalbach, Germany). Peptides and peptide derivatives with a C-terminal amide (—$CONH_2$-group) were synthesized on polystyrene-based 4-methylbenzhydrylamine (MBHA) resin (loading capacity 0.64 mmoL/g) from Merck Biosciences. Peptides and peptide derivatives were synthesized on a Syro2000 multiple peptide synthesizer (MultiSynTech GmbH) using four equivalents of the amino acid derivative activated with 2-(1-H-benzotriazole-1-yl)-tetramethyluronium hexafluorophosphate (HBTU; MultiSynTech GmbH) and N,N'-diisopropylethylamine (DIPEA; (Fluka, Buchs, Switzerland) in dimethylformamide (DMF; Biosolve V. B., Valkenswaard, The Netherlands). The side chain protecting groups were triphenylmethyl(trityl) for Asn, His, and Gln, tert.-butyl ether for Tyr, Ser, and Thr, tert.-butyl ester for Asp and Glu, N-omega-2,2,4,6,8-pentamethyldihydrobenzofuran-5-sulfonyl for Arg and βHar, and tert.-butyloxy-carbonyl for Lys and Orn. The temporary Fmoc-protecting group was cleaved with 40% piperidine in DMF (v/v) for 3 min and again with fresh 40% piperidine in DMF (v/v) for 10 min.

The N-termini of the peptides or peptide derivatives were acetylated with ten equivalents of acetic acid activated with HBTU and DIPEA in DMF, as described above for the Fmoc amino acid derivatives. The guanidation of the N-termini of the peptides or peptide derivatives was performed with ten equivalents of HBTU and DIPEA in DMF, as described by Gausepohl et al. [40].

After completion of the synthesis the peptide or peptide derivatives resins were washed thoroughly with DMF and DCM and dried under vacuum. The resin-bound peptides were cleaved from the solid support and simultaneously were the side-chains deprotected with a mixture of 5% water, 4% m-cresol, 5% thioanisole and 2% (by vol.) ethanedithiol in trifluoroacetic acid (TFA) at room temperature for 4 h. The peptides or peptide derivatives were precipitated with cold diethyl ether and centrifuged at 3000 G. The pellet was washed twice with cold ether, dried and dissolved in 0.1% aqueous TFA (UV-spectroscopy grade, Fluka). The samples were stored at −20° C.

C-terminally methylated peptides and peptide derivatives, i.e., containing a methyl (CO—OMe) or propyl (CO—OPr) ester, were synthesized on 4-hydroxymethylbenzoic acid AM resin (HMBA-AM resin, loading capacity 1.1 mmol/g, Novabiochem, Merck-Biosciences, Darmstadt, Germany). The first amino acid was coupled manually to the resin as a symmetric anhydride using 10 eq. of the Fmoc-amino acid derivative, 5 eq. diisopropylcarbodiimide (DIC), and 0.1 eq. N,N-dimethyl-4-amino pyridine in DCM. The loading capacity was determined in a piperidine fulvene assay by cleaving the Fmoc-group with 50% piperidine in DMF for 1 h, based on the absorption recorded at 301 nm [41]. Typical loading capacities were about 0.8 mmol/g. The automatic synthesis was performed as described above. After completion of the peptide synthesis the peptide HMBA-AM resin was washed thoroughly with DMF and DCM and dried under vacuum. The protecting groups of the resin-bound peptides were cleaved with 5% water, 4% m-cresol, 5% thioanisole and 2% (by vol.) ethanedithiol in trifluoroacetic acid (TFA) at room temperature for 4 h. The resin was washed with TFA and DMF. The resin was swollen in DMF and the peptide or peptide derivative was cleaved off the resin with DIPEA/MeOH/DMF (1:5:5 by vol.; 50 mL solution per g resin) to obtain the C-terminal methyl ester. To obtain the C-terminal propyl ester the peptide or peptide derivative was synthesized on 4-Sulfamylbutyryl AM resin (loading capacity 1.1 mmol/g, Novabiochem, Merck-Biosciences, Darmstadt, Germany) and cleaved with 50 eq. propylamine in DMF after activation with trimethylsilyldiazomethane in THF. The solvents were removed in vacuum, the peptides (or peptide derivatives) were precipitated with cold diethyl ether and centrifuged at 3000 G. The pellet was washed twice with cold ether, dried and dissolved in 0.1% aqueous TFA (UV-spectroscopy grade, Fluka). The samples were stored at −20° C. To obtain dimeric peptide derivatives $Fmoc_2$-Dab was coupled to the resin. After cleavage of the Fmoc-protecting groups two free N-termini were obtained and the peptide derivatives were synthesized as described above. The PEG3000 peptide derivatives were synthesized by activating PEG3000-OH with HBTU and DIPEA in DMF and coupling it to the N-terminus of the peptide or peptide derivatives, as described above for Fmoc amino acid derivatives.

Crude peptides and peptide derivatives were purified on an Äkta HPLC System (Amersham Bioscience GmbH, Freiburg, Germany) using a Jupiter C18-column (20 mm×250 mm, Phenomenex Inc., Torrance, USA). Elution was performed by a linear acetonitrile gradient, typically starting at 5% aqueous acetonitrile, with an increase of 1% acetonitrile per minute in the presence of 0.1% TFA as ion pair reagent. The flow rate was 10 mL/min and the peptides were detected by absorption at 220 nm. The purity of the peptides was determined by analytical RP-HPLC using a Jupiter C18-column (4.6 mm×150 mm, Phenomenex Inc., Torrance, USA) and matrix-assisted laser desorption/ionization time-of-flight mass spectrometry (MALDI-TOF-MS; 4700 proteomic analyzer, Applied Biosystems GmbH, Darmstadt, Germany).

The following peptides represented in table 2 were synthesized:

TABLE 2

| SEQ ID No. | Synthesis No. | Name | Sequence |
|---|---|---|---|
| 1 | A24 C3 | Apidaecin 1a acid | GNNRPVYIPQPRPPHPRI-OH |
| 2 | A24 C4 | Apidaecin 1b acid | GNNRPVYIPQPRPPHPRL-OH |
| 3 | A17 A3 ac. | Api 1a Amide ac. | Ac-GNNRPVYIPQPRPPHPRI-$NH_2$ |
| 4 | A17 A3 | Api 1a Amide | GNNRPVYIPQPRPPHPRI-$NH_2$ |
| 5 | A17 A6 ac. | Api 1b Amide ac. | Ac-GNNRPVYIPQPRPPHPRL-$NH_2$ |
| 6 | A17 A6 | Api 1b Amide | GNNRPVYIPQPRPPHPRL-$NH_2$ |

TABLE 2-continued

| SEQ ID No. | Synthesis No. | Name | Sequence |
|---|---|---|---|
| 7 | A18 G5 ac. | Api 1b O1 ac. | Ac-ONNRPVYIPQPRPPHPRL-NH$_2$ |
| 8 | A18 G5 | Api 1b O1 | ONNRPVYIPQPRPPHPRL-NH$_2$ |
| 9 | A17 A4 | Api 1a, O10 | GNNRPVYIPOPRPPHPRI-NH$_2$ |
| 10 | A21 E5 | Api.1b K4 R10 V19 | GNNKPVYIPRPRPPHPRLV-OH |
| 11 | A18 B4 | Api 1b O10 Hyp 11 | GNNRPVYIPO-4'Hyp-RPPHPRL-NH$_2$ |
| 12 | A20 B1 | Api 1b O1 O10 | ONNRPVYIPOPRPPHPRL-NH$_2$ |
| 13 | A20 B1 ac. | Api 1b O1 O10 ac. | Ac-ONNRPVYIPOPRPPHPRL-NH$_2$ |
| 14 | A14 B3 | Api 1a R10 | GNNRPVYIPRPRPPHPRI-NH$_2$ |
| 15 | A17 B3 | Api 1a R 10 Hyp 11 | GNNRPVYIPR-4'Hyp-RPPHPRI-NH$_2$ |
| 16 | A17 B5 | Api 1a O1 R10 | ONNRPVYIPRPRPPHPRI-NH$_2$ |
| 17 | A14 B4 | Api 1a K10 | GNNRPVYIPKPRPPHPRI-NH$_2$ |
| 18 | A17 B5 ac. | Api 1a R10 O1 ac. | Ac-ONNRPVYIPRPRPPHPRI-NH$_2$ |
| 19 | A14 D1 | Api 1a, Hyp5 | GNNR-4'Hyp-VYIPQPRPPHPRI-NH$_2$ |
| 20 | A17 B2 | Api.1b R10 Hyp11 | GNNRPVYIPR-4'Hyp-RPPHPRL-NH$_2$ |
| 21 | A24 C1 | Api 1b K1 K10 | KNNRPVYIPKPRPPHPRL-NH$_2$ |
| 22 | A24 C1 ac. | Api 1b K1 K10, ac. | Ac-KNNRPVYIPKPRPPHPRL-NH$_2$ |
| 23 | A21 A5 | Api O1 R10 PIRV | ONNRPVYIPRPRPPHPRPIRV-OH |
| 24 | A21 A5 ac. | Api O1 R10, PIRV, ac. | Ac-ONNRPVYIPRPRPPHPRPIRV-OH |
| 25 | A20 A5 | Api 1b V19 R10 | GNNRPVYIPRPRPPHPRLV-NH$_2$ |
| 26 | A14 B5 | Api 1a, L8 | GNNRPVYLPQPRPPHPRI-NH$_2$ |
| 27 | A24 A1 | Api O1 R10 PIRV | ONNRPVYIPRPRPPHPRPIRV-NH$_2$ |
| 28 | A24 A1 ac. | Api O1 R10 PIRV ac. | Ac-ONNRPVYIPRPRPPHPRPIRV-NH$_2$ |
| 29 | A21 B3 | Api 1b O1 V19 acid | ONNRPVYIPQPRPPHPRLV-OH |
| 30 | A21 B3 ac. | Api 1b O1 V19 acid ac. | Ac-ONNRPVYIPQPRPPHPRLV-OH |
| 31 | A21 A6 | Api 1b V19 R10 acid | GNNRPVYIPRPRPPHPRLV-OH |
| 32 | A25 D5 Orn ac. | Api MeLeu18 O1 ac. | Ac-ONNRPVYIPQPRPPHPR-MeLeu-NH$_2$ |
| 33 | A25 D5 Gly | Api MeLeu18 | GNNRPVYIPQPRPPHPR-MeLeu-NH$_2$ |
| 34 | A26 C2 | Api MeLeu18 R10 | GNNRPVYIPRPRPPHPR-MeLeu-NH$_2$ |
| 35 | A26 C5 Orn | Api Cha18 O10 O1 | ONNRPVYIPOPRPPHPR-Cha-NH$_2$ |
| 36 | A26 C3 Orn ac. | Api MeLeu R10 O1 ac. | Ac-ONNRPVYIPRPRPPHPR-MeLeu-NH$_2$ |
| 37 | A26 C4 | Api Cha18 R10 | GNNRPVYIPRPRPPHPR-Cha-NH$_2$ |
| 38 | A18 G6 | Api 1b O1 R10 | ONNRPVYIPRPRPPHPRL-NH$_2$ |
| 39 | A18 G6 ac. | Api 1b O1 R10 ac. | Ac-ONNRPVYIPRPRPPHPRL-NH$_2$ |
| 40 | A26 B2 ac. | Api 1b R10 Hyp11 O1 ac. | Ac-ONNRPVYIPR-4'Hyp-RPPHPRL-NH$_2$ |
| 41 | A26 B4 ac. | Api F18 O1 ac. | Ac-ONNRPVYIPQPRPPHPRF-NH$_2$ |
| 42 | A26 B4 | Api F18 O1 | ONNRPVYIPQPRPPHPRF-NH$_2$ |
| 43 | A26 B5 | Api 1b without R17 | GNNRPVYIPQPRPPHPL-NH$_2$ |

TABLE 2-continued

| SEQ ID No. | Synthesis No. | Name | Sequence |
|---|---|---|---|
| 44 | A26 B3 | Api F18 | GNNRPVYIPQPRPPHPRF-NH$_2$ |
| 45 | A26 B2 | Api 1b O1 R10 Hyp11 | ONNRPVYIPR-4'Hyp-RPPHPRL-NH$_2$ |
| 46 | A26 C5 Orn ac. | Api Cha18 O10 O1 ac. | Ac-ONNRPVYIPOPRPPHPR-Cha-NH$_2$ |
| 47 | A26 C3 Orn | Api MeLeu O1 R10 | ONNRPVYIPRPRPPHPR-MeLeu-NH$_2$ |
| 48 | A27 B6 ac. | Api 1b meth. O1 R10 ac. | Ac-ONNRPVYIPRPRPPHPRL-OMe |
| 49 | A27 B5 ac. | Api. 1b meth O1 O10 ac. | Ac-ONNRPVYIPOPRPPHPRL-OMe |
| 50 | A27 B4 ac. | Api 1b meth O1 ac. | Ac-ONNRPVYIPQPRPPHPRL-OMe |
| 51 | A14 C3 | Api 1a K15 | GNNRPVYIPQPRPPKPRI-NH$_2$ |
| 52 | A14 C4 | Api K15 P18 | GNNRPVYIPQPRPPKPRP-NH$_2$ |
| 53 | A14 C5 | Api R15 | GNNRPVYIPQPRPPRPRI-NH$_2$ |
| 54 | A14 A5 | Api I18 → PI | GNNRPVYIPQPRPPHPRPI-NH$_2$ |
| 55 | A14 B6 | Api L8, R10 | GNNRPVYLPRPRPPHPRI-NH$_2$ |
| 56 | A14 C1 | Api L8, K10 | GNNRPVYLPKPRPPHPRI-NH$_2$ |
| 57 | A14 D2 | Api 1a Hyp9 | GNNRPVYI-4'Hyp-QPRPPHPRI-NH$_2$ |
| 58 | A14 D3 | Api 1a Hyp11 | GNNRPVYIPQ-4'Hyp-RPPHPRI-NH$_2$ |
| 59 | A14 D4 | Api 1a Hyp13 | GNNRPVYIPQPR-4'Hyp-PHPRI-NH$_2$ |
| 60 | A14 D5 | Api 1a Hyp14 | GNNRPVYIPQPRP-4'Hyp-HPRI-NH$_2$ |
| 61 | A14 D6 | Api 1a Hyp16 | GNNRPVYIPQPRPPH-4'Hyp-RI-NH$_2$ |
| 62 | A18 A1 | Api 1a O1 | ONNRPVYIPQPRPPHPRI-NH$_2$ |
| 63 | A18 A1 ac. | Api 1a O1 | Ac-ONNRPVYIPQPRPPHPRI-NH$_2$ |
| 64 | A18 A2 | Api 1a O1 R10 | ONNRPVYIPRPRPPHPRI-NH$_2$ |
| 65 | A18 A2 ac. | Api 1a O1 R10 ac. | Ac-ONNRPVYIPRPRPPHPRI-NH$_2$ |
| 66 | A18 A5 | Api. 1b R10 | GNNRPVYIPRPRPPHPRL-NH$_2$ |
| 67 | A18 A5 ac. | Api. 1b R10 acety. | Ac-GNNRPVYIPRPRPPHPRL-NH$_2$ |
| 68 | A18 B1 | Api 1b K4 R10 V19 | GNNKPVYIPRPRPPHPRLV-NH$_2$ |
| 69 | A20 B4 | Api. 1b V19, R10 | GNNRPVYIPRPRPPHPRLV-OH |
| 70 | A21 A6 | Api. I18 --> PIRV | GNNRPVYIPQPRPPHPRPIRV-OH |
| 71 | A25 D3 Orn | Api. O1, Cha18, ac. | Ac-ONNRPVYIPQPRPPHPR-Cha-NH$_2$ |
| 72 | A25 D4 Orn | Api O1 D-Leu18 ac. | Ac-ONNRPVYIPQPRPPHPR-(D-Leu)-NH$_2$ |
| 73 | A25 D6 Orn | Api O1 tertGly18 ac. | Ac-ONNRPVYIPQPRPPHPR-tertGly-NH$_2$ |
| 74 | A25 E1 Orn | Api O1 βAla18 ac. | Ac-ONNRPVYIPQPRPPHPRβAla-NH$_2$ |
| 75 | A25 E2 Orn | Api O1 Chex18 ac. | Ac-ONNRPVYIPQPRPPHPR-Chex-NH$_2$ |
| 76 | A25 D3 Gly | Api Cha18 ac. | GNNRPVYIPQPRPPHPR-Cha-NH$_2$ |
| 77 | A25 D4 Gly | Api D-Leu18 ac. | GNNRPVYIPQPRPPHPR-(D-Leu)-NH$_2$ |
| 78 | A25 D6 Gly | Api tertGly18 ac. | GNNRPVYIPQPRPPHPR-tertGly-NH$_2$ |
| 79 | A25 E1 Gly | Api βAla18 ac | GNNRPVYIPQPRPPHPR-βAla-NH$_2$ |

TABLE 2-continued

| SEQ ID No. | Synthesis No. | Name | Sequence |
|---|---|---|---|
| 80 | A25 E2 Gly | Api Chex18 ac. | GNNRPVYIPQPRPPHPR-Chex-NH₂ |
| 81 | A29 C1 | Api 1b O1 R10 O17 | ONNRPVYIPRPRPPHPOL-NH₂ |
| 82 | A29 C1 ac. | Api 1b O1 R10 O17 ac | Ac-ONNRPVYIPRPRPPHPOL-NH₂ |
| 83 | A29 C4 ac. | Api. 1b O1 R10 Dab-Dimer | (Ac-ONNRPVYIPRPRPPHPRL)₂-Dab |
| 84 | A29 C5 FA | Formyl Api 1b | For-GNNRPVYIPQPRPPHPRL-NH₂ |
| 85 | A29 C5 guan | Api 1b N-guan. | Guan-GNNRPVYIPQPRPPHPRL-NH₂ |
| 86 | A28 A3 | Api O1 R10 PIRV Amide | ONNRPVYIPRPRPPHPRPIRV-NH₂ |
| 87 | A28 A3 ac. | Api O1 R10 PIRV Amide ac. | Ac-ONNRPVYIPRPRPPHPRPIRV-NH₂ |
| 88 | A30 C1 guan | Api O1 R10 guan. | Guan-ONNRPVYIPRPRPPHPRL-NH₂ |
| 89 | A17 A5 | Api Cit10 | GNNRPVYIP-Cit-PRPPHPRI-NH₂ |
| 90 | A17 B1 | Api 1a R10 Hyp11 | GNNRPVYIPR-4'Hyp-RPPHPRI-NH₂ |
| 91 | A17 B4 | Api 1a Cit 10 Hyp11 | GNNRPVYIP-Cit-4'Hyp-RPPHPRI-NH₂ |
| 92 | A17 C1 | Api 1a shortened | NNRPVYIPQPRPPHPRI-NH₂ |
| 93 | A14 C6 | Api P15 P18 | GNNRPVYIPQPRPPPPRP-NH₂ |
| 94 | A14 A6 | Api.1a K15 I18 → PI | GNNRPVYIPQPRPPKPRPI-NH₂ |
| 95 | A18-A6 | Api 1b K4 | GNNKPVYIPQPRPPHPRL-NH₂ |
| 96 | A18 B2 | Api 1b S3 V19 | GNSRPVYIPQPRPPHPRLV-NH₂ |
| 97 | A18 B3 | Api 1b S3 R10 K4 | GNSKPVYIPRPRPPHPRL-NH₂ |
| 98 | A18 F4 | Api 1a β-Homoarg10 | GNNRPVYIP-βHar-PRPPHPRI-NH₂ |
| 99 | A18 F5 | Api 1b β-Homoarg10 | GNNRPVYIP-βHar-PRPPHPRL-NH₂ |
| 100 | A19 C4 | Api 1b K4 R10 | GNNKPVYIPRPRPPHPRL-NH₂ |
| 101 | A19 C5 | Api 1b S3 | GNSRPVYIPQPRPPHPRL-NH₂ |
| 102 | A20 A6 | Api 1b O1 O10 Hyp11 | ONNRPVYIPO-4'Hyp-RPPHPRL-NH₂ |
| 103 | A20 A6 ac. | Api 1b O1 O10 Hyp11 ac | Ac-ONNRPVYIPO-4'Hyp-RPPHPRL-NH₂ |
| 104 | A20 B2 | Api 1b O10 Hyp11 | GNNRPVYIPO-4'Hyp-RPPHPRL-NH₂ |
| 105 | A20 B3 | Api. 1b O1 Hyp11 | ONNRPVYIPQ-4'Hyp-RPPHPRL-NH₂ |
| 106 | A20 B3 ac. | Api 1b O1 Hyp11 ac. | Ac-ONNRPVYIPQ-4'Hyp-RPPHPRL-NH₂ |
| 107 | A21 E4 | Api V18 | GNNRPVYIPQPRPPHPRV-NH₂ |
| 108 | A21 E6 | Api V18 | GNNRPVYIPQPRPPHPRV-OH |
| 109 | A24 A2 | Api PIPP Amide | GNNRPVYIPQPRPPHPRPIPP-NH₂ |
| 110 | A24 A3 | Api PIRV Amide | GNNRPVYIPQPRPPHPRPIRV-NH₂ |
| 111 | A24 B5 | Api 1b, P17 Amide | GNNRPVYIPQPRPPHPPL-NH₂ |
| 112 | A24 B6 | Api 1b O1 O10 P17 Amide | ONNRPVYIPOPRPPHPPL-NH₂ |
| 113 | A24 B6 ac. | Api 1b O1 O10 P17 Amide ac. | Ac-ONNRPVYIPOPRPPHPPL-NH₂ |
| 114 | A24 C2 | Api Y18 | GNNRPVYIPQPRPPHPRY-NH₂ |
| 115 | A24 C5 | Api without 18 | GNNRPVYIPQPRPPHPR-NH₂ |
| 116 | A27 B1 ac. | Api O1 ac I18 meth. | Ac-ONNRPVYIPQPRPPHPRI-OMe |

TABLE 2-continued

| SEQ ID No. | Synthesis No. | Name | Sequence |
|---|---|---|---|
| 117 | A27 B2 ac. meth. | Api O1 ac. O10 I18 | Ac-ONNRPVYIPOPRPPHPRI-OMe |
| 118 | A27 B3 ac. meth. | Api O1 ac. R10 I18 | Ac-ONNRPVYIPRPRPPHPRI-OMe |
| 119 | A29 C4 | Api O1 R10 Api.1b Dab-Dimer | (ONNRPVYIPRPRPPHPRL)$_2$-Dab |
| 120 | A30 C3 guan. | Api O1 guan. | Guan-ONNRPVYIPQPRPPHPRL-NH$_2$ |
| 121 | A30 C6 ac. | Api 1b β-Homoarg17 | ONNRPVYIPQPRPPHP-βHar-L-NH$_2$ |
| 122 | A32 C1 | Api 1b, R10, Dimer | (GNNRPVYIPRPRPPHPRL)$_2$-Dab |
| 123 | A32 C1 guan. | Api 1b, R10 guan, Dimer | (Guan-GNNRPVYIPRPRPPHPRL)$_2$-Dab |
| 124 | A32 C2 ac. | Api 1b O1 R10 Dimer | (Ac-ONNRPVYIPRPRPPHPRL)$_2$-Dab |
| 125 | A32 C2 guan | Api 1b O1 R10 Dimer | (Guan-ONNRPVYIPRPRPPHPRL)$_2$-Dab |
| 126 | A36 A6 | Api 1b O1 R10 PIRV | ONNRPVYIPRPRPPHPRPIRV-OH |
| 127 | A36 B2 ac. | Api 1b Dimer, O1 R10 O17 | (Ac-ONNRPVYIPRPRPPHPOL)$_2$-Dab |
| 128 | A36 B2 guan. | Api 1b Dimer, O1 R10 O17 | (Guan-ONNRPVYIPRPRPPHPOL)$_2$-Dab |
| 129 | A36 B3 ac. | Api 1b Dimer | (Ac-GNNRPVYIPQPRPPHPRL)$_2$-Dab |
| 130 | A36 B3 guan | Api 1b Dimer | (Guan-GNNRPVYIPQPRPPHPRL)$_2$-Dab |
| 131 | A36 B6 ac. | Api 1b O1, R10, Har17 | Ac-ONNRPVYIPRPRPPHP-Har-L-NH$_2$ |
| 132 | A36 C1 ac. | Api 1b Har17 | Ac-GNNRPVYIPQPRPPHP-Har-L-NH$_2$ |
| 133 | A36 C1 guan. | Api 1b Har17 | Guan-GNNRPVYIPQPRPPHP-Har-L-NH$_2$ |
| 134 | A37 A1 guan. | Api. 1b O1 R10 O17 guan | Guan-0NNRPVYIPRPRPPHPOL-NH$_2$ |
| 135 | A37 C3 PEG | Api 1b O1 R10 PEG3000 | PEG-ONNRPVYIPRPRPPHPRL-NH$_2$ |
| 136 | A44 A4 F1 | Api 1b A7, A17 | GNNRPVYIAQPRPPHPAL-NH$_2$ |
| 137 | A47 A1 guan. | Api 1b O1 R10 acid, guan | Guan-ONNRPVYIPRPRPPHPRL-OH |
| 138 | A49 A1 | Api 1b O1 R10 Cit17 | ONNRPVYIPRPRPPHP-Cit-L-NH$_2$ |
| 139 | A49 A3 | Api 1b A17 | GNNRPVYIPQPRPPHPAL-NH$_2$ |
| 140 | A49 A4 | Api 1b A9 | GNNRPVYIAQPRPPHPRL-NH$_2$ |
| 141 | A49 A5 | Inverse Api. 1b | LRPHPPRPQPIYVPRNNG-NH$_2$ |
| 142 | A49 A6 | Api 1b, GNN shortend | RPVYIPQPRPPHPRL-NH$_2$ |
| 143 | A49 B1 | Api 1b E4 | GNNEPVYIPQPRPPHPRL-NH$_2$ |
| 144 | A49 B2 | Api 1b -L shortend | GNNRPVYIPQPRPPHPR-OH |
| 145 | A49 B3 | Api 1b O1 R10 Arginal17 | ONNRPVYIPRPRPPHPArginal-Leu-NH$_2$ |
| 146 | A53 G5 guan. | Api 1b O1 R10, Agp17 | Guan-ONNRPVYIPRPRPPHP-Agp-L-NH$_2$ |
| 147 | A53 H1 guan. | Api 1b O, R10 propylester, guan | Guan-ONNRPVYIPRPRPPHPRL-OPr |
| 148 | A34 B6 ac. | Api 1b Cit17 ac | Ac-GNNRPVYIPQPRPPHP-Cit-L-NH$_2$ |

TABLE 2-continued

| SEQ ID No. | Synthesis No. | Name | Sequence |
|---|---|---|---|
| 149 | A34 B6 guan. | Api Ib; Cit17 guan | Guan-GNNRPVYIPQPRPPHP-Cit-L NH$_2$ |
| 150 | A34 C1 ac. | Api 1b O1 R10 Cit17 | Ac-ONNRPVYIPRPRPPHP-Cit-L-NH$_2$ |
| 151 | A34 C1 guan. | Api 1b, O1 R10 Cit17 | Guan-ONNRPVYIPRPRPPHP-Cit-L NH$_2$ |
| 152 | A35 D2 ac. | Api 1b O1 R10 D-R17 | Ac-ONNRPVYIPRPRPPHP-DR-L-NH$_2$ |
| 153 | A35 D4 ac. | Api 1b O1 R10 Me-R17 | Ac-ONNRPVYIPRPRPPHP-MeR-L-NH$_2$ |
| 154 | A35 D5 ac. | Api 1b O1 R10 NO2-R17 | Ac-ONNRPVYIPRPRPPHP-NO2R-L-NH$_2$ |
| 155 | A38 A1 guan. | Api 1b O1 R10 Har17 | Guan-ONNRPVYIPRPRPPHP-Har-L NH$_2$ |
| 156 | A57 A1 guan. | Api 1b O1 R10 4tHyp 5, guan | Guan-ONNR-4'Hyp-VYIPRPRPPHPRL-NH$_2$ |
| 157 | A57 A2 guan. | Api 1b O1 R10 4tHyp 9 guan | Guan-ONNRPVYI-4'Hyp-RPRPPHPRL-NH$_2$ |
| 158 | A57 A3 guan. | Api 1b O1 R10 4tHyp 11, guan | Guan-ONNRPVYIPR-4'Hyp-RPPHPRL-NH$_2$ |
| 159 | A32 C5 guan | Api 1b R10 guan | Guan-GNNRPVYIPRPRPPHPRL-NH$_2$ |
| 160 | Dy675 A36 B5 | Api 1b O1, R10, Dy675 | N-alpha-Dy675-ONNRPVYIPRPRPPHPRL-NH$_2$ |

DR: D-arginine, MeR=Methylarginine, preferably alpha-N-methylarginine (5-(diaminomethylideneamino)-2-methylaminopentanoic acid), NO2R=Nitroarginine, preferably N(G)-Nitroarginine (2-amino-5-[(amino-nitramidomethylidene)amino]pentanoic acid), Cit: Citrulline; Ac=Acetyl, For=Formyl, Guan=Guanido group are examples for modified N-termini (modified alpha-aminogroup of the N-terminal amino acid, Sub$_1$=Acetyl-NH, Formyl-NH or Guanido).

Agp: alpha-Amino-beta-guanidinopropionic acid Arginal: —COOH in Arginine is replaced by —CHO, Cha: cyclohexylalanine, Chex: 1-amino-cyclohexylcarbonic acid, Cit: Citrulline, OMe is standing for a methylester at the c-terminus (Sub$_2$=OR$_3$=OMe), OPr is standing for a propylester at the C-terminus (Sub$_2$=OR$_3$=O—Pr); MeLeu=N-Methylleucine—a leucine with a methylation of the peptide bond; Ac=Acetyl, For=Formyl, Guan=Guanido group are examples for modified N-termini (modified alpha-aminogroup of the N-terminal amino acid, Sub$_1$=Acetyl-NH, Formyl-NH or Guanido); βAla and βHar are examples for beta-amino acids.

EXAMPLE 2

Serum Stability

Serum stability studies were carried out in duplicate as described by Hoffmann et al. [42]. Briefly, 28 µL of an aqueous peptide or peptidomimetics solution (0.5 mg/mL) was added to 0.2 mL freshly pooled 25% mouse serum (Sigma-Aldrich GmbH, Taufkirchen, Germany) in water. The mixtures were incubated at 37° C. under gentle stirring. The proteins were precipitated with 40 µL of 15% aqueous TCA after incubation times of 0, 0.5, 1, 2, 4 and 6 h at 0° C. for 20 min before centrifuged (13500×G) at 4° C. for 5 min. The supernatants of all samples (240 µL) were neutralized with 1 mol/L aqueous NaOH and immediately stored at −20° C. The supernatants were analyzed by RP-HPLC using a linear acetonitrile gradient as described above with 0.1% TFA as ion pair reagent. Collected fractions of the main peaks were further analyzed by tandem mass spectrometry (MALDI-TOF/TOF-MS, 4700 Proteomics Analyzer, Applied Bio systems GmbH, Weiterstadt, Germany) in positive ion reflector mode using α-cyanohydroxycinnamic acid (50% CH$_3$CN in 0.1% aqueous TFA) as matrix to identify the degradation products of the peptides and peptidomimetics, i.e., metabolites, at the different time points. Serum control samples consisted of 200 µL of pooled 25% mouse serum in water, which were also precipitated with 40 µL 15% aqueous TCA, as described before. Peptide reference samples consisted of 28 µL of the peptide stock solution diluted in 0.2 mL water and 40 µL of 15% aqueous trichloroacetic acid (TCA).

The serum stabilities of several peptides are represented in table 3:

TABLE 3

| SEQ ID No. | Peptide | Sequence | Half-life time |
|---|---|---|---|
| 1 | A24 C3 | GNNRPVYIPQPRPPHPRI-OH | 120 min |
| 2 | A24 C4 | GNNRPVYIPQPRPPHPRL-OH | 120 min |

TABLE 3-continued

| SEQ ID No. | Peptide | Sequence | Half-life time |
|---|---|---|---|
| 4 | A17 A3 amide | GNNRPVYIPQPRPPHPRI-NH$_2$ | 15 min |
| 6 | A29 C2 | GNNRPVYIPQPRPPHPRL-NH$_2$ | 15 min |
| 7 | A18 G5 ac. | Ac-ONNRPVYIPQPRPPHPRL-NH$_2$ | 15 min |
| 8 | A18 G5 | ONNRPVYIPQPRPPHPRL-NH$_2$ | 30 min |
| 12 | A20 B1 | ONNRPVYIPOPRPPHPRL-NH$_2$ | 15 min |
| 13 | A20 B1 ac. | Ac-ONNRPVYIPOPRPPHPRL-NH$_2$ | 15 min |
| 23 | A21 A5 | ONNRPVYIPRPRPPHPRPIRV-OH | 240 min |
| 24 | A21 A5 ac. | Ac-ONNRPVYIPRPRPPHPRPIRV-OH | 240 min |
| 32 | A25 D5 Orn ac. | Ac-ONNRPVYIPQPRPPHPR-MeLeu-NH$_2$ | >360 min |
| 81 | A29 C1 | Ac-ONNRPVYIPRPRPPHPOL-NH$_2$ | 120 min |
| 82 | A29 C1 ac. | Ac-ONNRPVYIPRPRPPHPOL-NH$_2$ | >360 min |
| 83 | A29 C4 ac. | (Ac-ONNRPVYIPRPRPPHPRL)$_2$-Dab | 15 min |
| 88 | A30 C1 guan | Guan-ONNRPVYIPRPRPPHPRL-NH$_2$ | 15 min |
| 110 | A24 A3 | GNNRPVYIPQPRPPHPRPIRV-NH$_2$ | 360 min |
| 131 | A36 B6 ac. | Ac-ONNRPVYIPRPRPPHP-Har-L-NH$_2$ | 120 min |
| 134 | A37 A1 guan | Guan-ONNRPVYIPRPRPPHPOL-NH$_2$ | >360 min |
| 137 | A47 A1 guan | Guan-ONNRPVYIPRPRPPHPRL-OH | >360 min |
| 155 | A38 A1 guan | Guan-ONNRPVYIPRPRPPHP-Har-L-NH$_2$ | >360 min |

The native (wt) apidaecin sequences SEQ ID NO. 1 and 2 are degraded from both ends, i.e., N-terminal and C-terminal residues or peptides are cleaved off.

Thus, the peptide sequence is preferably be stabilized at both ends against exopeptidases or exoproteases as well as endoproteases. A bond susceptible to endoproteases is especially the bond between arginine in position 17 and isoleucine or leucine in position 18. The degradation was monitored by MALDI-MS by determining the molecular masses of the peptidic metabolites and the tandem mass spectrum of the corresponding peptides. The N-terminal degradation resulted in sequences shortened by one to three residues.

N-terminal acetylation (SEQ ID No. 7, 13, 24, and 32) for example reduced this degradation pathway significantly without major impact on the C-terminal degradation. For example, peptide Ac-ONNRPVYIPQPRPPHPRL-NH$_2$ (SEQ ID No. 7) and Ac-ONNRPVYIPRPRPPHPRL-NH$_2$ (SEQ ID No. 13) were not degraded N-terminally, but only from the C-terminal end cleaving either the C-terminal leucine amide or the two C-terminal residues (FIG. 1).

N-terminal guanidation is even superior to acetylation in reducing N-terminal degradation (SEQ ID No. 134, 137 and 155).

FIG. 1 shows the amounts of peptide Ac-ONNRPVYIPQPRPPHPRL-NH$_2$ (SEQ ID No. 7) present in 25% aqueous serum after 30, 60, 120, 240, and 360 min as well as the two detected metabolites Ac-ONNRPVYIPQPRPPHPR-OH (SEQ ID NO. 164—cleavage of C-terminal leucine amide) and Ac-ONNRPVYIPQPRPPHP-OH (SEQ ID NO. 165—cleavage of two C-terminal residues) as quantified by the peak areas obtained by RP-HPLC using UV detection.

Similarly the C-terminal degradation was reduced by amidation of the C-terminus for example, which did not affect the N-terminal degradation either. Thus, the combination of both N- and C-terminal modifications significantly reduced the degradation by exopeptidases or exoproteases (SEQ ID No. 7, 13 and 32). The cleavage C-terminal to Arg-17, i.e., Arg-Leu or Arg-Ile, was effectively reduced by N-methylation of this peptide bond. Preferably, a peptide is stabilized against all three possible degradation pathways as illustrated for Ac-ONNRPVYIPQPRPPHPRMeLeu-NH$_2$ (SEQ ID No. 32), which showed a half-life (25% aqueous serum, 37° C.) of more than 6 hrs. The same stability was obtained for sequence Ac-ONNRPVYIPRPRPPHPOL-NH$_2$ (SEQ ID No. 82) by replacing Arg-17 by ornithine, as ornithine is not tryptic cleavage site.

EXAMPLE 3

Antibacterial Assays

1. Inhibition Zone Assay (Agar Plate Assay)

The purified apidaecin-derived peptides and peptide derivatives were diluted to a final concentration of 500 µg/mL in water. Aliquots of 10 µL and controls (10 µL water or antibiotic solution) were applied to an agar plate seeded with a suspension of a midlogarithmic phase bacterial culture. The plates were incubated at 37° C. in the darkness. The diameter of the inhibition zones was measured after 20 h. In general the bacteria were grown on 1% tryptic soy broth (TSB, Fluka, Neu-Ulm, Germany) and 1.2% agar (Fluka). All tests were done under aerobic conditions.

Figure 2:
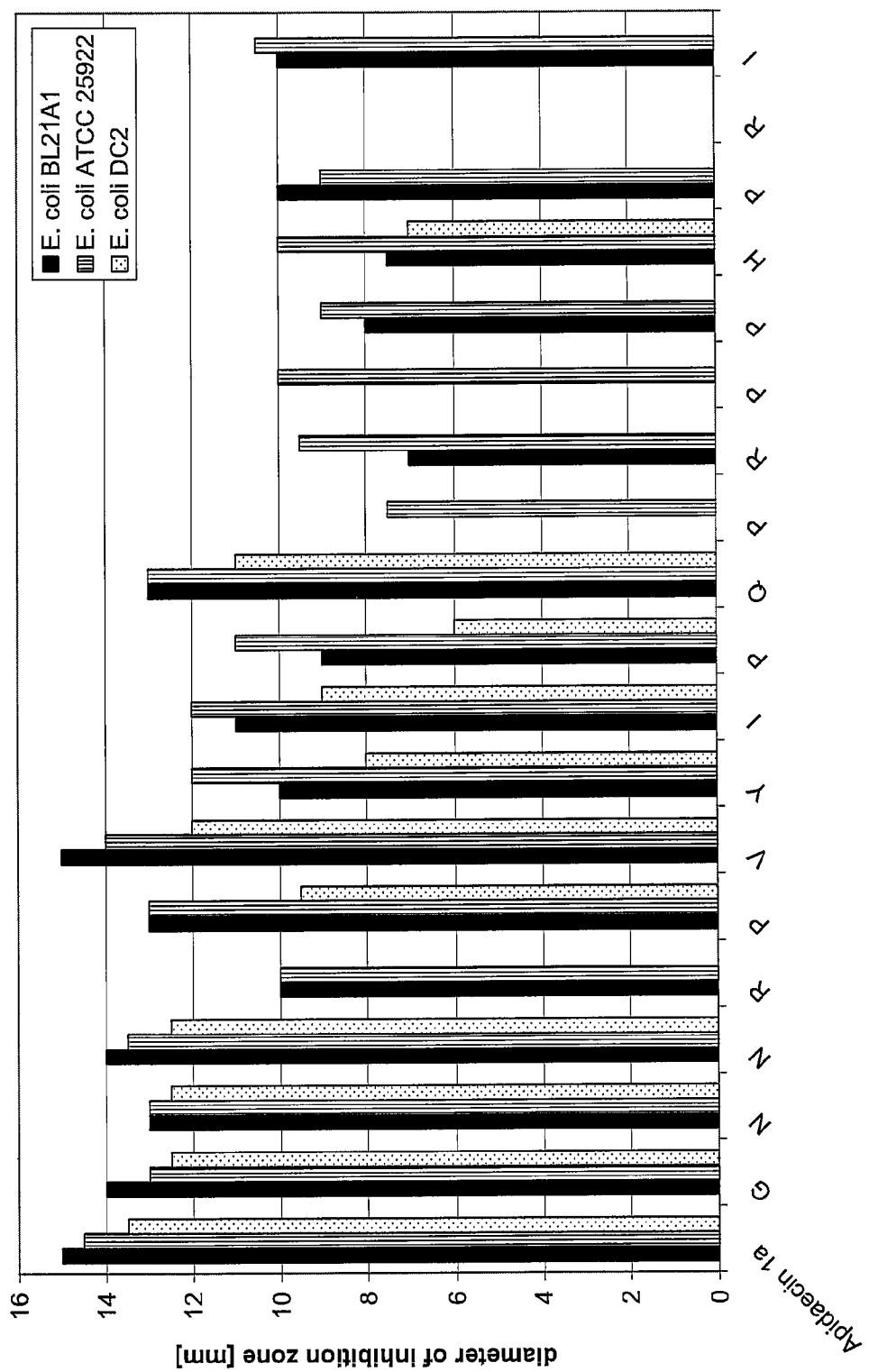
FIG. 2 shows the Antibacterial activity of apidaecin 1a analogs (alanine-scan) against different *E. coli* strains using an agar plate assay.
Figure 3:
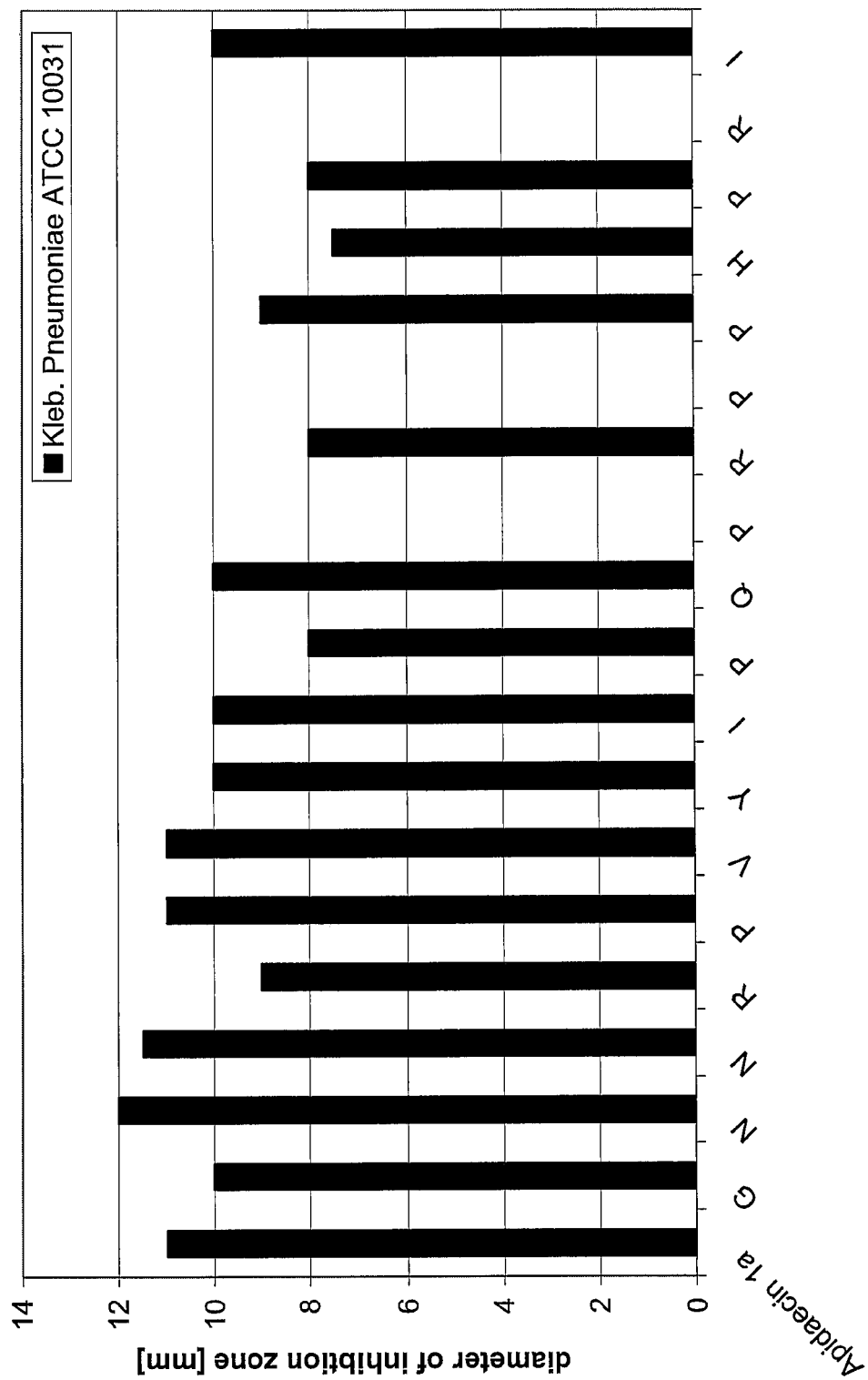
FIG. 3 shows the Antibacterial activity of apidaecin 1a analogs (alanine-scan) against *Klebsiella pneumoniae* strain ATCC 10031 using an, agar plate assay.

An alanine scan of the native apidaecin sequence identified several residues responsible for the antimicrobial activity against three different *E. coli* strains (FIG. 2) and *K. pneumoniae* (FIG. 3).

FIG. 2 shows the Antibacterial activity of apidaecin 1a analogs (alanine-scan) against different *E. coli* strains using an agar plate assay.

FIG. 3 shows the Antibacterial activity of apidaecin 1a analogs (alanine-scan) against *Klebsiella pneumoniae* strain ATCC 10031 using an agar plate assay.

In the diagrams shown in FIG. 2 and FIG. 3 the sequence of the natural peptide apidaecin 1a GNNRPVYIPQPRPPHPRI (SEQ ID NO. 1) is shown in the X-axis. Each residue represents the corresponding peptide, wherein the residue is replaced by an alanine, e.g. G at position 1 standing for: ANNRPVYIPQPRPPHPRI (SEQ ID NO. 166), N at position 2 standing for GANRPVYIPQPRPPHPRI (SEQ ID NO. 167), and so on.

The bar represents the diameter of the inhibition zone. Thus, the higher the bar the higher antibacterial activity of the alanine modified peptide.

With the alanine scan all positions responsible to the antibacterial activity in apidaecin 1 were determined. The antibacterial activity was strongly reduced if positions Pro11 to Ile18, Arg4, Tyr7 and Pro9 were replaced by alanine. In further experiments specific amino acid positions were replaced by other similar amino acids to increase the activity and the protease resistance. In most cases a strong decrease in the activity was obtained.

All tested strains from both bacteria showed a very similar response to the various single site mutations with Pro in position 11 and Arg in position 17 of the native sequence being obligatory to restore at least a partial activity.

2. Growth Inhibition Assay

The minimal inhibition concentrations (MIC) of the apidaecin-derived peptides and peptide-derivatives were determined by a growth inhibition assay using a serial peptide dilution in sterilized round-bottom 96-well plates (polystyrene, U-bottom, Greiner Bio-One GmbH) with a final volume of 100 µL per well. The bacteria, e.g., *E. coli* BL21 AI, were grown in nutrient broth (NB, Carl Roth GmbH+Co. KG, Karlsruhe, Germany) at 37° C. over night. To each well of the 96-well plate, 50 µL of the overnight culture adjusted to $5 \times 10^6$ CFU/mL in 1% TSB were added. Lyophilized peptides and peptidomimetics were dissolved in 1% TSB (tryptic soy broth) or water to give a final concentration of 250 µg/mL. Fifty µL of the peptide or peptidomimetics solution were added to the first well of a row on the plate and mixed. Fifty µL of the first well containing the peptide solution were transferred to the second well, mixed and again 50 µL transferred to the next well and so on. Thereby, a two-fold dilution series was obtained starting at 250 µg/mL in the first well down to 120 ng/mL in the $12^{th}$ well of a row giving a final peptide or peptidomimetics concentration from 125 µg/mL (well 1) to 60 ng/mL (well 12). Plates were incubated at 37° C. for 20 hrs. The absorbance was measured at 595 nm using a TECAN micro plate spectrophotometer (Tecan, Germany). All peptides and peptidomimetics were measured in triplicates. Sterilized water was used as a negative control. The MIC value expresses the lowest concentration at which no bacterial growth was observed after incubation at 37° C. for at least 20 hrs.

The MIC values of the tested peptides and peptide derivatives against bacteria of several multidrug resistant bacteria are summarized in table 4.

The following multidrug resistant bacteria strains were tested:
*Eschericha coli* 45849 and D31,
*Klebsiella pneumoniae* 123132 and K6,
*Salmonella typhi* S5 and *Salmonella enterica* subsp. enterica serovar *Typhimurium* (ATCC 700408),
*Rhizobium radiobacter* (ATCC 15955 deposited as *Agrobacterium tumefaciens*).

TABLE 4

| SEQ ID No. | Synthesis No. | E. coli 45849 | K. Pneumonia 123132 | S. typhi S5 | E. coli D31 | K. Pneumonia K6, ATCC 700603 | S. enterica subsp. Enterica serovar. typhi G10215 ATCC 700408 | R. radiobacter ATCC 15955 |
|---|---|---|---|---|---|---|---|---|
| 1 | A24 C3 | | | | 64 | 64 | 2 | |
| 2 | A24 C4 | | | | 32 | 64 | 2 | |
| 6 | A29 C2 | 0.5 | 16 | 0.125 | 1 | 16 | 0.125 | n.t. |
| 7 | A18 G5 ac. | 1 | 16 | 2 | 4-8 | 64 | 0.5-1 | <0.16 |
| 8 | A18 G5 | <0.25 | 1 | <0.5 | 2 | 16 | <0.25 | <0.16 |
| 9 | A17 A4 | 1 | 8 | 2 | 16 | 16 | 0.5 | <0.16 |
| 11 | A18 B4 | 1 | 8 | <0.5 | 8 | 8 | <0.25 | <0.16 |
| 12 | A20 B1 | 1 | 4 | <0.5 | 4 | 4 | <0.25 | 0.65 |
| 13 | A20 B1 ac. | 2 | 8 | <0.5 | 4 | 8 | <0.25 | <0.16 |
| 14 | A14 B3 | | | | 64 | 8 | 2 | |
| 15 | A17 B3 | 1 | 4 | 2 | 64 | 16 | 2 | 0.33 |
| 16 | A17 B5 | | | | 128 | 32 | 2 | |
| 17 | A14 B4 | 8 | 16 | 16 | 32 | 32 | 4 to 8 | 0.65 |
| 20 | A17 B2 | 1 | 4 | <0.5 | 32 | 8 | 0.5 | 0.33 |
| 21 | A24 C1 | <0.25 | 4 | 1 | 8 | 8 | 0.25-0.5 | 0.65 |
| 22 | A24 C1 ac. | 1 | 16 | 1 | 16 | 16 | 1 | <0.16 |
| 23 | A21 A5 | 8 | 16 | 8 | 64 | 32 | 8 | 0.65 |
| 25 | A20 A5 | 1 | 16 | 2 | 64 | 16 | 1 | 0.65 |
| 26 | A14 B5 | 16 | 32 | 32 | >128 | 128 | 4 | 2.6 |
| 32 | A25 D5 Orn ac. | 8 | >64 | 32 | 64 | >128 | 8 | 1.3 |
| 33 | A25 D5 Gly | | | | 32 | >128 | 8 | |
| 34 | A26 C2 | 4 | 32 | 8 | 8 | 32 | 4 to 8 | 1.3 |
| 35 | A26 C5 Orn | 16 | 32 | 16 | 8 | 16 | 4 to 8 | 2.6 |
| 36 | A26 C3 Orn ac. | 4 | 32 | 16-32 | 8 | 64-128 | 4 to 8 | 1.3 |
| 37 | A26 C4 | 16 | 16 | 16 | 8 | 32 | 8 | 10.5 |

TABLE 4-continued

| SEQ ID No. | Synthesis No. | E. coli 45849 | K. Pneumonia 123132 | S. typhi S5 | E. coli D31 | K. Pneumonia K6, ATCC 700603 | S. enterica subsp. Enterica serovar. typhi G10215 ATCC 700408 | R. radiobacter ATCC 15955 |
|---|---|---|---|---|---|---|---|---|
| 38 | A18 G6 | 0.5 | 2 | <0.5 | 2 | 4 | 2 | 1.3 |
| 39 | A18 G6 ac. | 1 | 4 | <0.5 | 4 | 16 | 4 | 0.33 |
| 40 | A26 B2 ac. | 1 | 4 | <0.5 | 8 | 16 | 4 | 0.33 |
| 41 | A26 B4 ac. | 4 | 32 | 8 | >128 | 128 | 8 | 5.25 |
| 43 | A26 B5 | | | | >128 | >64 | >64 | |
| 44 | A26 B3 | | | | | 128 | 64 | 4 |
| 45 | A26 B2 | 1 | 4 | <0.5 | 8 | 4 | 2 | 0.65 |
| 46 | A26 C5 Orn ac. | 32 | 32-64 | 32 | 16 | 32-64 | 8 | 10.5 |
| 47 | A26 C3 Orn | 4 | 32 | 32 | 8 | 32-64 | 8 | 1.3 |
| 48 | A27 B6 | 4 | 32 | 4 | 64 | 128 | 16 | 1.3 |
| 49 | A27 B5 | 2 | 64 | 4 | 32 | 128 | 8 | 1.3 |
| 50 | A27 B4 | | | | >128 | >128 | 32 | |
| 81 | A29 C1 | 8 | 8 | 4 | 8 | 16 | 4 | n.t. |
| 82 | A29 C1 ac. | 16 | 8 | 8 | 32 | 32 | 8 | n.t. |
| 83 | A29 C4 ac. | 8 | 8 | 4 | 2 | 8 | 4 | n.t. |
| 84 | A29 C5 guan | 0.5 | 32 | 0.25 | 1 | 32 | 0.25 | n.t. |
| 85 | A29 C5 FA | 2 | 16 | 0.5 | 16 | 64 | 0.5 | n.t. |
| 88 | A30 C1 guan | 0.5 | 1 | 0.125 | 0.5 | 0.5 | 0.125 | n.t. |
| 120 | A30 C3 guan | 0.25 | 4 | 0.125 | 0.5 | 8 | 0.125 | n.t. |
| 121 | A30 C6 guan | 128 | 128 | n.t. | 16 | >128 | n.t. | n.t. |
| 133 | A37 A1 guan | 16 | 16 | 16 | 16 | 16 | 2 | n.t. |
| 137 | A47 A1 guan | <1 | 1 | <1 | <1 | 4 | <1 | n.t. |
| 155 | A38 A1 guan | 4 | 2 | 4 | 4 | 4 | 0.5 | n.t. |
| 159 | A32 C5 guan | 1 | 4 | 0.25 | 1 | 4 | 0.25 | n.t. |

SEQ ID No. Nr. 1, 2 are the wild type sequences as comparison examples, SEQ ID No. 4, 19, 26, 32, 33, 41, 43, 44, 50, 121 and 133 are less preferred examples according to the invention (with a Q as $X_4$—in position 10). The other SEQ ID No. shown, are preferred peptides or peptide derivatives according to the invention. Most preferred examples are SEQ ID No. 6, 7-8, 11-13, 20-22, 25, 39, 40, 45, 65, 67, 84, 85, 88, 137, 155 and 159.

Amidation of the C-terminus results not only in better antimicrobial activities, i.e., lower MIC values, but also reduces C-terminal degradation by exoproteases. Similarly modification, preferably acetylation or guanidation, of the N-terminal amino group reduces N-terminal degradation, as described above. However, N-terminal acetylation reduces the MIC values for some of the tested bacterial strains (e.g., SEQ ID No. 21 compared to SEQ ID No. 22 and SEQ ID No. 38 compared to SEQ ID No. 39), which indicates that the N-terminal residues should carry a positive charge. Consequently, glycine in the $X_1$ position was replaced by residues carrying a positively charged side chain, like lysine (e.g. SEQ ID No. 21), arginine and ornithine (e.g. SEQ ID No. 12). Another possibility to introduce a positive charge at the N-terminus is N-terminal guanidation, which at the same time stabilizes the N-terminus against degradation (e.g. SEQ ID No. 133 and 137). These N-terminally modified peptides carrying a residue with positively charged side chain in Position $X_1$ showed better MIC values than the acetylated wt apidaecin sequences. Another important residue to improve the antimicrobial activity is substitution of glutamine in position 10 (residue $X_4$) by a residue carrying a positively charged side chain, such as ornithine (e.g. SEQ ID No. 12 and 13), lysine (e.g. SEQ ID No. 21 and 22) or arginine (e.g. SEQ ID No. 38 and 39). This substitution in position 10 (residue $X_4$) by a residue carrying a positively charged side chain does not reduce the protease resistance, as the following position contains a proline, which effectively reduces the proteolytic cleavage of the N-terminal peptide bond by endoproteases.

Substitution of proline in position 11 (residue $X_5$) by hydroxyproline does neither influence the MIC values within the error range of the assay nor reduce the protease resistance of its N-terminal peptide bond. Whereas this substitution by hydroxyproline in position 11 (residue $X_5$) does neither affect the MIC values nor the serum stability, the higher polarity further reduces the cell toxicity and the haemolytic activity, as more polar peptides bind less to cell membranes. Thus a very preferred peptide contains ornithine in position 1 (residue $X_1$), arginine in position 10 (residue $X_4$) and hydroxyproline in position 11 (residue $X_5$, an acetylated N-terminus, and a C-terminal amide, such as SEQ ID No. 40). Furthermore, the peptide bond between positions 17 and 18, i.e., Arg and Leu/Ile of the original sequence, is modified to increase its protease or peptidase resistance, such as N-methylation (e.g. SEQ ID No. 33, 34). Alternatively arginine in position 17 (residue $X_6$) is replaced by a basic residue not prone the proteolysis, such as ornithine (e.g. SEQ ID No. 38, 131 to 133, 146 to 155).

The MIC values of the tested peptides and peptide derivatives against bacteria of several species are summarized in table 5.

The bacteria strains were tested:

Eschericha coli 1103, 10233, BL 21 AI, DC 2,

Klebsiella pneumoniae 681,

Micrococcus luteus ATCC 10240,

Mycobacterium vaccae

Bactillus subtillis 347.

TABLE 5

| SEQ ID No. | Synthesis No. | E. coli 10233 | E. coli BL 21 AI | M. luteus ATCC 10240 | E. coli 1103 | E. coli DC 2 | K. pneumonia 681 | Mycobacterium vaccae | B. subtilis 347 |
|---|---|---|---|---|---|---|---|---|---|
| 1 | A24 C3 | 1.95 | 0.98 | 31.25 | 1.95 | 3.91 | 15.62 | >125 | >125 |
| 2 | A24 C4 | 1.95 | 0.98 | 31.25 | 7.81 | | 62.5 | | >125 |
| 7 | A18 G5 ac. | | 0.49 | 3.91 | 1.95 | 3.9 | 1.95 | 125 | >125 |
| 8 | A18 G5 | | 0.24 | 7.84 | 1.95-0.95 | 0.98 | 1.95 | 125 | >125 |
| 9 | A17 A4 | | 0.49 | 1.95 | 3.9 | 1.95 | 3.9 | 125 | >125 |
| 11 | A18 B4 | 3.91 | 0.49 | 1.95 | 3.9 | 0.98 | 1.95 | 125 | 125 |
| 12 | A20 B1 | 0.98-1.95 | 0.98 | 1.95 | 3.91 | | 7.81 | | 62.5 |
| 13 | A20 B1 ac. | 1.95 | 1.95 | 1.95 | 3.81 | | 3.91 | | 125 |
| 14 | A14 B3 | | 0.49 | 0.98 | 0.98 | 7.81 | 15.62 | | |
| 15 | A17 B3 | | 0.98 | 1.95 | 1.95 | 3.9 | 3.9 | 125 | >125 |
| 16 | A17 B5 | | 0.98 | 3.91 | | | | | |
| 17 | A14 B4 | | 0.98 | 0.98 | 1.95 | 31.25 | 31.25 | | |
| 20 | A17 B2 | | 0.49 | 1.95 | 3.9 | 1.95-3.91 | 3.9 | 125 | >125 |
| 21 | A24 C1 | | 1.95-3.91 | 1.95-0.98 | | | | | |
| 22 | A24 C1 ac. | | 1.95 | 1.95 | | | | | |
| 23 | A21 A5 | 3.91 | 1.95-3.91 | 0.12 | 7.81 | | 62.5 | | 125 |
| 25 | A20 A5 | | 3.91 | 1.95 | | | | | |
| 26 | A14 B5 | | 3.91 | 1.95 | 3.91 | 7.81 | 15.62 | | |
| 32 | A25 D5 Orn ac. | 31.25 | 15.63 | 7.81 | 31.4 | | >125 | | >125 |
| 33 | A25 D5 Gly | 15.63 | 15.63 | 31.25 | 62.5 | | >125 | | >125 |
| 38 | A18 G6 | 1.95 | 1.95 | 1.95 | 3.91 | 0.98 | 1.95 | 125 | 62.5 |
| 39 | A18 G6 ac. | 1.95 | 1.95 | 0.98 | 3.91 | 0.98 | 3.9 | 125 | 125 |
| 40 | A26 B2 ac. | 1.95 | | | 3.91 | | 3.91 | | 125 |
| 45 | A26 B2 | 1.95-3.91 | | | 7.81 | | 7.81 | | 62.5 |
| 62 | A18 A1 | | 1.95 | 7.81 | | | | | |
| 63 | A18 A1 ac. | | 3.91 | 3.91 | | | | | |
| 65 | A18 A2 ac. | | 0.98 | 0.98 | 1.95 | 7.81 | 7.81 | 62.5 | 125 |
| 66 | A18 A5 | | 1.95 | 1.95 | 3.9 | 1.95 | 3.9 | 125 | 62.5 |
| 67 | A18 A5 ac. | | 3.91 | 1.95 | 3.9 | 3.9 | 3.9 | 125 | 125 |
| 68 | A18 B1 | | 7.81 | 0.24 | 3.9 | 7.81 | 31.25 | 125 | >125 |
| 69 | A20 B4 | | 7.81 | 0.24 | | | | | |
| 70 | A21 A6 | | 15.63 | 0.49 | | | | | |
| 71 | A25 D3 Orn | | 62.5-31.25 | 7.81-3.91 | | | | | |
| 72 | A25 D4 Orn | | >125 | 7.81 | | | | | |
| 73 | A25 D6 Orn | | 62.5 | 7.81 | | | | | |
| 74 | A25 E1 Orn | | >125 | 7.81 | | | | | |
| 75 | A25 E2 Orn | | >125 | 7.81 | | | | | |
| 76 | A25 D3 Gly | | 62.5 | 15.63 | | | | | |
| 77 | A25 D4 Gly | | >125 | 31.25 | | | | | |
| 78 | A25 D6 Gly | | 125-62.5 | 31.25 | | | | | |
| 79 | A25 E1 Gly | | >125 | 62.5 | | | | | |
| 80 | A25 E2 Gly | | >125 | 15.63 | | | | | |
| 83 | A29 C4 ac. | 31.25 | 1.95 | 1.95 | | | 125 | | 15.6 |
| 84 | A29 C5 for | 1.95 | 1.95 | 3.91 | | | 62.5 | | >125 |
| 85 | A29 C5 guan | 1.95 | 0.24 | 15.63 | | | 31.25 | | >125 |
| 86 | A28 A3 | | 3.91 | 0.98 | | | | | 62.5 |
| 88 | A30 C1 guan | 1.95 | 0.98 | 1.95 | | | 7.81 | | 62.5 |
| 89 | A17 A5 | | 1.95 | 15.63 | | | | | |
| 90 | A17 B1 | | 0.98 | 7.81 | | | | | |
| 91 | A17 B4 | | 1.95 | 7.81 | | | | | |
| 92 | A17 C1 | | 3.91 | 31.25 | | | | | |
| 102 | A20 A6 | | 1.95 | 1.95 | | | | | |
| 103 | A20 A6 ac. | | 1.95 | 3.91 | | | | | |
| 131 | A36 B6 ac. | | 4 | 0.5 | 16 | | 16 | | 32 |
| 132 | A36 C1 ac | | 32 | 32 | 64 | | 32 | | 128 |
| 133 | A36 C1 guan | | 64 | 32 | 16 | | 8 | | |
| 134 | A37 A1 guan | | 2 | 4 | 32 | | 16 | | >128 |
| 135 | A37 C3 PEG | >125 | >125 | 8 | >125 | | >125 | | >125 |
| 136 | A44 A4 F1 | | >125 | >125 | | | | | |
| 137 | A47 A1 guan | | <0.5 | 8 | 8 | | 2 | | 64 |
| 138 | A49 A1 | | 64 | 64 | | | | | |
| 139 | A49 A3 F1 | | >125 | >125 | | | | | |
| 140 | A49 A4 F1 | | >125 | 125 | | | | | |
| 141 | A49 A5 | >125 | >125 | >125 | >125 | | >125 | | >125 |
| 142 | A49 A6 F1 | | 125 | 125 | | | | | |
| 144 | A49 B2 | | >125 | >125 | | | | | |
| 146 | A53 G5 | | 32 | 4 | 64 | | 32 | | 125 |
| 147 | A53 H1 guan | | 4 | 16 | 16 | | 8 | | 64 |
| 148 | A34 B6 ac. | | >125 | >125 | | | | | |
| 150 | A34 C1 ac. | | 32 | 32 | | | | | |
| 151 | A34 C1 | | 16 | 64 | | | | | |

TABLE 5-continued

| SEQ ID No. | Synthesis No. | E. coli 10233 | E. coli BL 21 AI | M. luteus ATCC 10240 | E. coli 1103 | E. coli DC 2 | K. pneumonia 681 | Mycobacterium vaccae | B. subtilis 347 |
|---|---|---|---|---|---|---|---|---|---|
| 152 | A35 D2 ac. guan | | 32 | 32 | | | | | |
| 153 | A35 D4 ac. | | 16 | 32 | | | | | |
| 154 | A35 D5 ac. | | 16 | 32 | | | | | |
| 155 | A38 A1 guan | | 4 | 1 | 4 | | 4 | | 32 |

SEQ ID No. Nr. 1, 2 are the wild type sequences as comparison examples. SEQ ID No. 32, 33, and 70-80, as well as SEQ ID No. 132, 133, 135, 136, 139, 140, 143, 144 and 148 are less preferred examples according to the invention (with Q as $X_4$—position 10). Inverse apidaecin (SEQ ID No. 141) and the shortened apidaecin peptides (SEQ ID No. 92 and 142) are also less preferred. The other SEQ ID No. shown, are preferred peptides or peptide derivatives according to the invention. Most preferred examples are SEQ ID No. 7, 8, 9, 11-17, 20-23, 25, 38 40, 45, 65-67, 84, 85, 88, 134 and 137.

Generally, the measured antibacterial activity in the microdilution assay for the peptide sequences tested is very similar to the data presented in table 4 and discussed afterwards. Briefly, amidation of the C-terminus is desired as it significantly reduces the MIC values for the tested bacteria. Acetylation of the N terminus reduces the N-terminal degradation by peptidases or proteases, as described above. The best MIC values were obtained for peptides and peptidomimetics carrying a positively charged group at the N-terminal end of the peptide, thus it is advantageous to substitute glycine in position 1 by lysine (e.g. SEQ ID No. 21 and 22), argenine or ornithine (e.g. SEQ ID No. 7 and 8) that all carry a positively charged side chain. Ornithine is preferred as it does not introduce a tryptic cleavage side. These N-terminally acetylated peptides showed better MIC values than the acetylated wt sequences. Another important residue to improve the antimicrobial activity is substitution of glutamine in position 10 (residue $X_4$) by residues carrying a positively charged side chain, such as ornithine (e.g. SEQ ID No. 12 and 13), lysine (e.g. SEQ ID No. 21 and 22) or arginine (e.g. SEQ ID No. 38 and 39). This substitution does not reduce the protease resistance, as the following position contains a proline, which effectively reduces the proteolytic cleavage of the N-terminal peptide bond. As an alternative to N-terminal acetylation the guanidation (e.g. SEQ ID No. 88, 134 and 137) was also very effective and additionally extended the activity to B. subtilis that is resistant to the wt apidaecin sequences as well as most analogs. Substitution of proline in position 11 (residue $X_5$) by hydroxyproline does neither reduce the MIC values nor the protease resistance, but as a more polar amino acid it further reduces the cell toxicity and the haemolytic activity. Thus a preferred peptide contains ornithine in position 1 (residue $X_1$), arginine or ornithine in position 10 (residues $X_4$) and hydroxyproline in position 11 (residue $X_5$), an acetylated or guandidated N-terminus, and a C-terminal amide, such as SEQ ID No. 40, 103.

Interestingly, some modifications introduced an activity against B. subtilis, which is not observed for the native wt apidaecin peptides. The common feature of these sequences with activity against B. subtilis is a positively charged N-terminus, i.e. free amino group or guandidated N-terminus, an arginine or ornithine in position 10 (residues $X_4$) and preferably an ornithine in position 1 (residue $X_1$) of the apidaecin 1b sequence (Leucine in position 18—e.g. SEQ ID No. 12, 38, 45, 66, 131-134 and 155). The corresponding homologous apidaecin 1a peptides (Isoleucine in position 18) were not active against B. subtilis. The same sequence modifications (charged N-terminus, an arginine or ornithine in position 10 and an ornithine in position 1) of the apidaecin 1a sequence extended the activity towards M. vaccae (SEQ ID No. 65).

EXAMPLE 4

Assays for Toxicity to Mammalian Cells

1. Hemolytic Assay

To determine whether the peptides and peptide derivatives according to the invention were toxic to mammalian cells, several peptides and peptidomimetics from Example 1 above, a positive control, and a negative control were examined for hemolytic activity. The hemolytic activity was assayed with human erythrocytes [43]. A human erythrocyte concentrate was provided in sodium chloride adenin-glucose-mannitol buffer from the Leipzig University Hospital (Leipzig, Germany). The erythrocytes were centrifuged at 1000 G and washed three times with 10 volumes of cold phosphate-buffered saline (PBS, pH 7.4). The erythrocytes were diluted to a final concentration of 1% in PBS. One hundred microliters of this human erythrocyte suspension in PBS was added to each well of a V-shaped 96-well polypropylene microtiter plate (Greiner Bio-One GmbH). To each well 100 µL peptide dissolved in PBS were added to obtain a dilution series starting from 600 µg/mL to 4.8 µg/mL in seven dilution steps. The microtiter plate was incubated at 37° C. for 1 h and subsequently centrifuged for 10 min at 1000 G. One hundred microliters of the supernatant was transferred to a 96-well flat-bottomed polystyrene microtiter plate (Greiner Bio-One GmbH) and the absorption at 405 nm recorded in a micro plate spectrophotometer (Tecan) to evaluate the heme release. PBS and 0.1% Triton X-100 were used as negative and positive controls. The hemolysis percentage was calculated by the following equation [44]:

$$(E_{peptide} - E_{PBS})/(E_{Triton} - E_{PBS}) \times 100\% \text{ with}$$
$$E = \text{Extinction at 405 nm}$$

Figure 4:
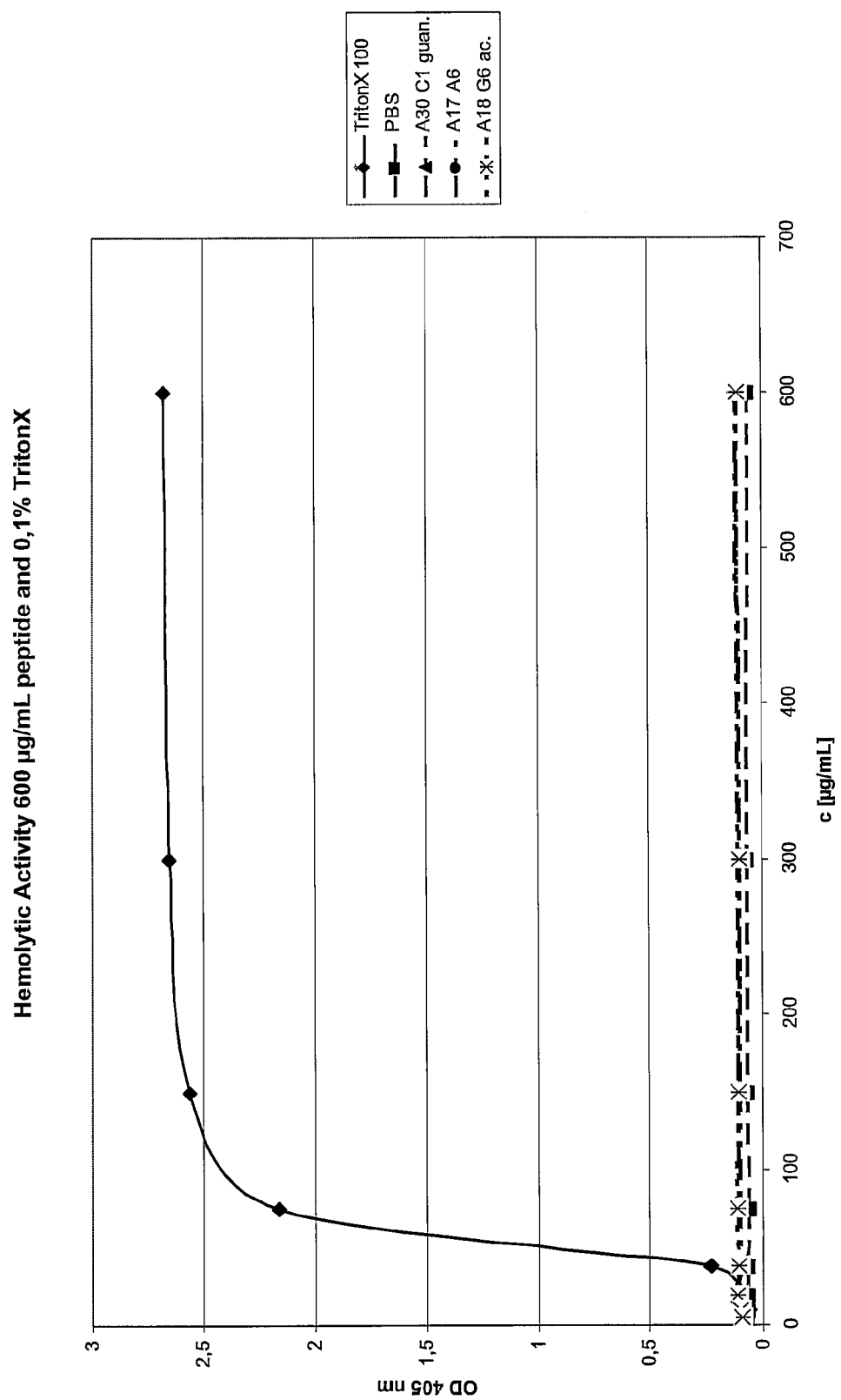
FIG. 4 shows the result of the hemolytic assay for the peptides A30 C1 guan. (SEQ ID NO: 88) and A18 G6 ac. (SEQ ID NO: 39) and A17 A6 (SEQ ID NO: 6), peptide concentration 600 μg/mL, PBS and TritonX-100™ (p-tert-Octylphenoxy)polyethoxyethanol, 0.1%) as controls.

All hemolytic assays were performed in duplicates. FIG. 4 and table 6 show the average of three independent experiments.

FIG. 4 shows the result of the hemolytic assay for the peptides A30 C1 guan. (SEQ ID No. 88) and A18 G6 ac. (SEQ ID No. 39) and A17 A6 (SEQ ID NO. 6), peptide concentration 600 µg/mL, PBS and TritonX-100® (p-tert-Octylphenoxy)polyethoxyethanol, 0.1%) as controls.

Results for further peptides and peptide derivatives are summarized in table 6:

TABLE 6

| Seq. ID No. | Synthesis No. | Haemolysis rate [%] |
|---|---|---|
| 1 | A24 C3 | 0.9 |
| 2 | A24 C4 | 0.8 |
| 38 | A18 G6 | 1.0 |
| 39 | A18 G6 ac. | 1.4 |
| 23 | A21 A5 | 1.1 |
| 24 | A21 A5 ac. | 0.9 |
| 83 | A29 C4 ac. | 1.3 |
| 84 | A29 C5 FA | 0.8 |
| 33 | A25 D5 Gly | 0.6 |
| 88 | A30 C1 guan. | 1.3 |
| 120 | A30 C3 guan | <1 |
| 131 | A36 B6 ac | <1 |
| 133 | A36 C1 guan | <1 |
| 134 | A37 A1 guan | <1 |
| 135 | A37 C3 PEG | <1 |
| 151 | A34 C1 guan | <1 |
| 155 | A38 A1 guan | <1 |
| | Triton X-100 ® | 100 |

None of the examined peptides showed any hemolytic activity up to a peptide concentration of 600 µg/mL, i.e., even at 100 to 1200 times higher concentrations than the obtained MIC values. The hemolytic rates for all peptides were only about 1% relative to triton, which is within the background of this assay. The non-ionic tenside Triton X-100® was used as a positive control, as it completely destroys the red blood cells in the experimental setup within one hour. This cell assay indicates that the peptides and peptide derivatives can be applied in blood at high concentrations without any side effects on the red blood cells. In conclusion, all tested peptides and peptide derivatives fulfill the requirement that ideal antimicrobial compounds should not show any hemolytic activity at 100 fold higher concentrations than the MIC values.

2. Assays for Toxicity to COS Cells

COS-7 cells were grown in Dulbecco's modified Eagle medium (Cellgro, Meidatech Inc., Herndon, Va., U.S.A.) containing 10% fetal bovine serum at 37° C. in an atmosphere of 10% $CO_2$. The cells ($5 \times 10^3$ cells/well) were plated in 24-well tissue culture dishes and incubated for 24 h prior to peptide addition. The peptides were dissolved in 0.5 mL water and inoculated into 1 mL medium to final concentrations of 60, 200 and 600 µg/mL in duplicates. The plates were incubated for 24 h more at 37° C. in an atmosphere of 10% $CO_2$. The medium was aspirated and the assay was terminated by adding 100 µL of trypsin ethylenediamine tetraacetate (EDTA) (0.25% trypsin/0.1% EDTA in Hank's balanced salt solution; Cellgro). The treated and control samples were harvested, washed in PBS and fixed with cold 70% aqueous ethanol for 2 hrs. The cells were then resuspended in PBS containing 10 µg/mL of propidium iodide (PI) and 250 µg/mL of RNAse and incubated for 30 min at 37° C. The necrotic/apoptotic rates were assessed by flow cytometry analyses performed on a Guava® EasyCyte™ Mini System (Guava Technologies, Hayward, Calif., USA).

This assays studies the effect of the tested peptides and peptide derivatives in doublets at different concentrations on the cell cycle of a COS-7 cell culture, i.e., the percentage of cells in G1, S, G2/M phase as well as necrotic and apoptotic cells. The data are evaluated relative to a blank (no peptides and peptide derivatives added) and a solution of 10% DMSO, which completely destroys the cells.

The results are summarized in table 7. As shown in the previous table, none of the peptides and peptide derivatives had any detectable influence on the cell cycle distribution, as they were all within the error range of the two blanks, even at the highest concentrations of 600 µg/mL. Most important necrosis and apoptosis were not elevated compared to the blank. This data in combination with the hemolytic activities (Tab. 6) proof that the studied peptides and peptide derivatives are not cytotoxic at the cellular level even at concentrations up to 600 µg/mL, which is more than 100 times above the MIC values.

TABLE 7

| SEQ ID No. | Peptide | Concentration [µg/mL] | Necrosis and Apoptosis % | G1 % | S1 % | G2/M % |
|---|---|---|---|---|---|---|
| 8 | A18 G5 | 600 | 11 | 39 | 26 | 24 |
| | | 600 | 15 | 38 | 26 | 21 |
| | | 200 | 17 | 47 | 26 | 9 |
| | | 200 | 16 | 43 | 27 | 14 |
| | | 60 | 18 | 44 | 29 | 9 |
| 32 | A25 D5 Orn ac. | 600 | 10 | 35 | 28 | 27 |
| | | 600 | 13 | 42 | 28 | 17 |
| | | 200 | 29 | 29 | 27 | 15 |
| | | 200 | 18 | 37 | 32 | 13 |
| | | 60 | 18 | 39 | 29 | 14 |
| 45 | A26 B2 | 600 | 11 | 40 | 25 | 23 |
| | | 600 | 16 | 43 | 27 | 14 |
| | | 200 | 20 | 49 | 26 | 6 |
| | | 200 | 18 | 50 | 24 | 9 |
| | | 60 | 18 | 45 | 25 | 13 |
| 23 | A21 A5 | 600 | 11 | 40 | 27 | 22 |
| | | 600 | 11 | 38 | 28 | 24 |
| | | 200 | | | | |
| | | 200 | 19 | 39 | 29 | 13 |
| | | 60 | 20 | 40 | 28 | 13 |
| controls | blank | | 12 | 35 | 28 | 25 |
| | blank1 | | 23 | 33 | 33 | 10 |
| | blank2 | | 17 | 41 | 22 | 20 |
| | 10% DMSO 1 | 10% (v/v) | 0 | 0 | 0 | 0 |
| | 10% DMSO 2 | 10% (v/v) | 0 | 0 | 0 | 0 |

EXAMPLE 5

Induction of Resistance

The induction of resistance strains was determined according to the macro dilution method under NCCLS-conditions (National Committee for Clinical Laboratory Standards—now Clinical and Laboratory Standards Institute Wayne, Pa., USA, NCCLS-Guideline, M7-A5, Vol. 20, Nr. 2; 2000).

Firstly, minimal inhibition concentrations (MIC) were determined for the peptides to be examined as described in example 3.2. To determine induction of resistance continued dilutions of the peptide with concentrations ranging from 3 fold to 4 fold above to below the MIC were chosen. The test was performed in sterile 96-well microtiter plates with round bottoms (Polystyrene, U-bottom, Greiner Bio-One GmbH, Germany) and 200 µL final volume per well. The freeze-dried peptide or peptide derivatives were dissolved in water and diluted in respect to the MIC in 1% TSB (tryptic soy broth) to obtain a volume of 100 µL. As example for an MIC-value of 2 µg/mL the dilution series were chosen from 32 µg/mL to 0.25 µg/mL. The dilutions within the series were twofold.

The bacteria, E. coli BL21 AI, were grown overnight at 37° C. in nutrient broth (NB, Carl Roth GmbH+Co. KG, Karlsruhe, Germany) and diluted to $5 \times 10^6$ colony forming units (CFU)/mL in 1% TSB. To start the assay 100 µL of the bacteria dilution was added per well of the microtiter plate loaded with peptide. After incubating the plates for 24 h at 37°

C., the absorption was determined at 595 nm using a TECAN microtiter plate reader (Tecan, Germany).

MIC values were calculated as described in example 3.2. The test was repeated using new dilution series with peptide concentrations adapted to the new determined MIC values and using the bacteria culture that grew despite the presence of the inhibitory peptide. This bacteria culture (1$^{st}$ passage) was diluted to 5×10$^6$ CFU/mL in 1% TSB. After incubation with the new peptide dilution series for 24 h at 37° C., absorption was determined at 595 nm and again MIC-values were calculated. The test was repeated again with using new dilution series with peptide concentrations adapted to the new determined MIC values and using the bacteria culture that grew despite the presence of the inhibitory peptide (2$^{nd}$ passage). The same procedure was applied for about 8 further passages.

As a control a untreated E. coli BL21 AI culture was chosen and passaged without inhibitory peptides. All peptides and peptide derivatives were measured in triplicates. The number of passages was chosen dependent on the rapidity of induction of resistance and commonly was 10 passages over 10 continuous days.

FIG. 5 shows the induction of resistance, comparing wild type Apidaecin 1b (SEQ. ID No. 2) and two optimized sequences according to the invention (SEQ. ID No. 88 and 137):

| SEQ ID No. | Name | Sequence |
|---|---|---|
| 2 | Apidaecin 1b acid | GNNRPVYIPQPRPPHPRL-OH |
| 88 | Api 1b O1 R10 guan. | Guan-ONNRPVYIPRPRPPHPRL-NH$_2$ |
| 137 | Api 1b O1 R10 acid guan | Guan-ONNRPVYIPRPRPPHPRL-OH |

For the wild type Apidaecin sequence the first resistance strains were obtained already after the 2nd passage. Resistance increased up to a MIC-value of 128 μg/mL in the 10$^{th}$ passage.

However, for the two sequences according to the invention (SEQ. ID No. 88 and 137) no induction of resistance was observed at all. Thus, the induction of resistance does not depend on the C-terminus.

The MIC-values of the untreated E. coli BL21 AI control, which was passaged along, did not change during the test.

These results illustrate that the compounds according to the invention can be advantageously applied for a long period of time as novel antibiotics without the induction of resistance in E. coli.

EXAMPLE 6

Measuring In Vivo Distribution

The in vivo distribution was measured in mice using fluorescent-labelled peptides derivatives.

Near-infrared absorbing fluorescent dye Dy675 (Dyomics GmbH, Jena, Germany) was activated with DIC and coupled to the N-terminus of the peptide derivatives after completion of the solid phase peptide synthesis (see example 1). Afterwards the peptides were cleaved with TFA and purified by RP-HPLC (see example 1).

Forty μg of the labelled peptide derivatives were injected subcutaneously (sc) or intra-peritional (ip) into shaved and isoflurane anesthetized female Balb/c mice. The animals were placed into the fluorescence microscope chamber under continuous isoflurane exposure. Fluorescence exposure pictures were taken with an IVIS microscope set to 695 nm emission wavelength at every minute in the first 10 min after peptide addition and every 5 min afterwards until 65 min.

Figure 6B:
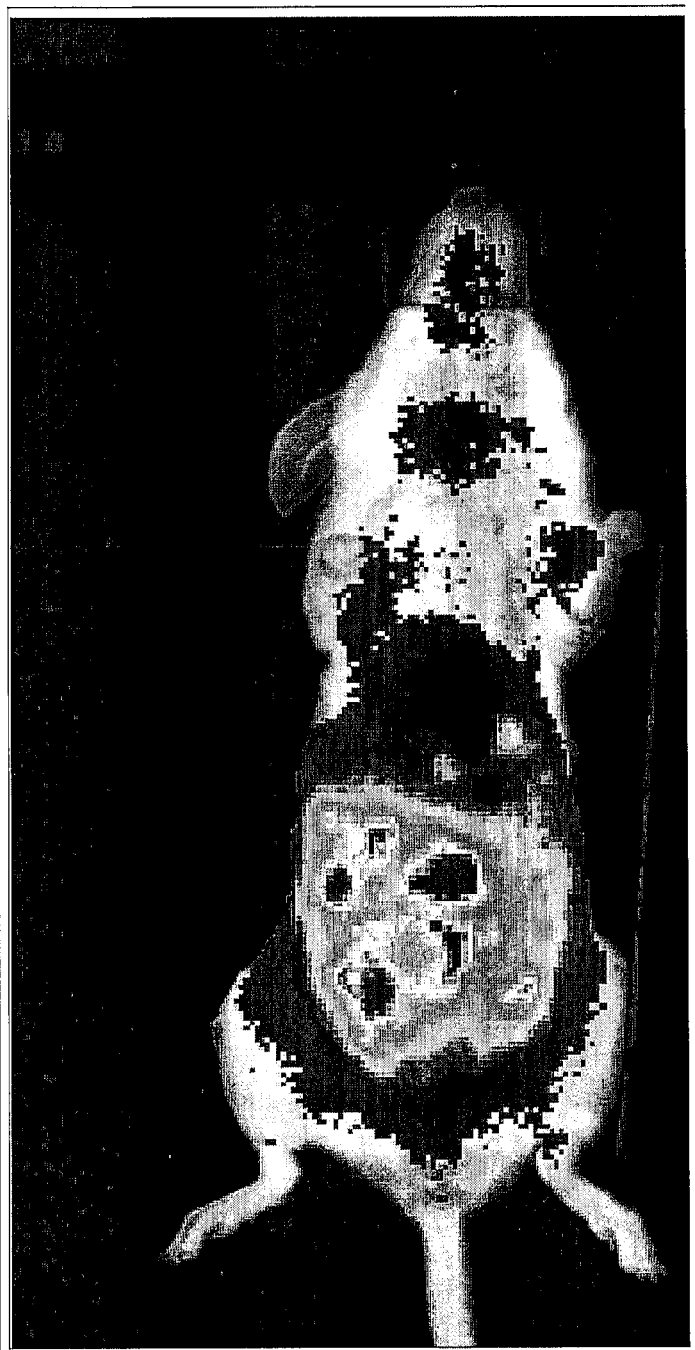
Figure 6C:
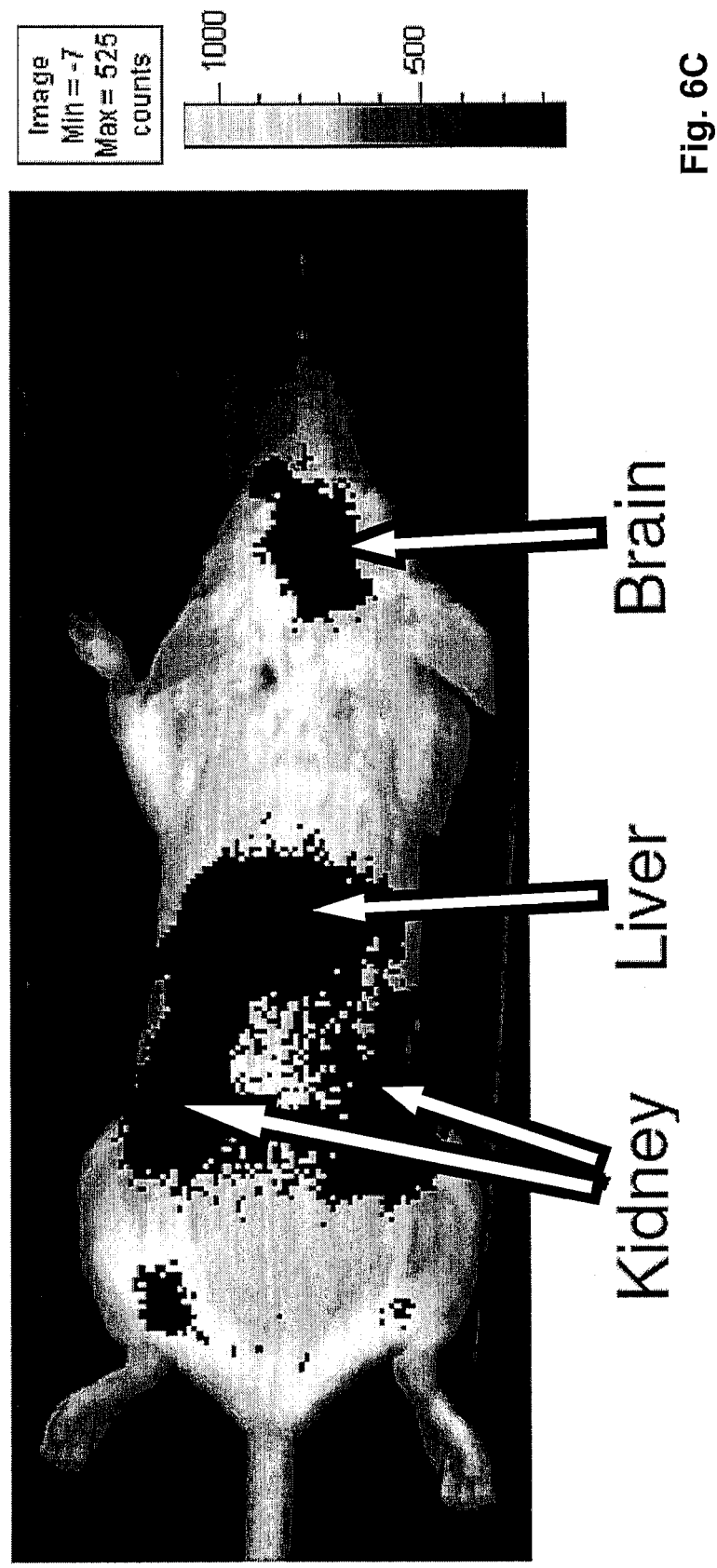

FIGS. 6A-6C show the in vivo imaging and biodistribution of the fluorescent labelled peptide Dy675-ONNRPVY-IPRPRPPHPRL-NH$_2$ (SEQ ID No. 160) 60 and 65 minutes after intra-peritional injection. Shown are the images after 60 min (FIG. 6A, belly, low intensity), 65 min (FIG. 6B, belly, high intensity) and after 65 min (FIG. 6C, back, high sensitivity). The colour bar indicates the fluorescence intensity. The labelled fluorescent peptide derivative was injected i.p. and its distribution was studied by in-vivo imaging at several time points. FIG. 6C taken from the back clearly shows that the peptides were enriched in brain, liver, and both kidneys. In FIG. 6B the brain is also stained whereas the kidneys and liver are not seen due to the high peptide concentration at the injection site.

Most of the inoculated peptide remained after 60 min at the site of drug administration. Small amounts of the peptide were distributed throughout the body.

The pharmaceutical promise of the new peptide derivatives is that they reach different organs of the animals within 60 min including brain, liver and kidney, which clearly shows that the peptides are distributed by blood to all organs in the body.

Abbreviations:

The following abbreviations are used throughout to refer to amino acids:

| | | |
|---|---|---|
| | Agp | Guanidino propionic acid |
| A | Ala | Alanine |
| | βAla or bAla | beta-Alanine, beta-Aminoproponic acid |
| R | Arg | Arginine |
| | Har | Homoarginine |
| | βHar or bHar | beta-Homoarginine |
| | Cha | Cyclohexylalanine |
| | Chex | 1-Amino-cyclohexylcarbonic acid |
| | Dab or Dbu: | Diaminobutyric acid |
| D | Asp | Aspartic acid |
| N | Asn | Asparagine |
| | Cit | Citrulline |
| C | Cys | Cysteine |
| | GABA | Gamma (γ)-aminobutyric acid |
| Q | Gln | Glutamine |
| E | Glu | Glutamic acid |
| G | Gly | Glycine |
| H | His | Histidine |
| | Hyl | δ-Hydroxylysine |
| I | Ile | Isoleucine |
| L | Leu | Leucine |
| | MeLeu | N-Methylleucine |
| K | Lys | Lysine |
| M | Met | Methionine |
| O | Orn | Ornithine |
| P | Pro | Proline |
| | 3Hyp | 3-Hydroxyproline in cis or trans |
| | 4Hyp | 4-Hydroxyproline in cis or trans |
| | 3$^c$Hyp | cis-3-Hydroxyproline |
| | 3$^t$Hyp | trans-3-Hydroxyproline |
| | 4$^c$Hyp | cis-4-Hydroxyproline |

| | | |
|---|---|---|
| | 4'Hyp | trans-4-Hydroxyproline |
| F | Phe | Phenylalanine |
| T | Thr | Threonine |
| | tertGly | tert.-butylglycine |
| Y | Tyr | Tyrosine |
| S | Ser | Serine |
| W | Trp | Tryptophan |
| V | Val | Valine |

Other abbreviations include the following:
Ac: Acetyl,
Api: Apidaecin
AMP: Antimicrobial peptides,
BSA: Bovine serum albumin,
CFU: Colony forming units,
DCM: Dichloromethane,
DMF: Dimethylformamide,
EDTA: Ethylenediamine tetraacetate,
ESI: Electrospray ionization,
DIPEA: N,N'-Diisopropylethylamine,
For: Formyl(Methanoyl),
Fmoc: 9-Fluorenylmethoxycarbonyl,
Guan: Guanidino-group,
HBTU: 2-(1-H-benzotriazole-1-yl)-tetramethyluronium hexafluorophosphate,
HPLC: High performance liquid chromatography,
HMBA: 4-Hydroxymethylbenzoic acid,
MALDI: Matrix-assisted laser desorption/ionization,
Me: Methyl,
MeCN: Acetonitrile,
MeOH: Methanol,
MIC: Minimal inhibitory concentration,
MS: Mass spectrometry,
NB: Nutrient broth,
OMe: Methylester
PBS: Phosphate buffered saline,
PI: Propidium iodide,
RP: Reversed-phase,
RT: Room temperature,
'Bu: tert.-butyl,
TCA: Trichloroacetic acid,
TFA: Trifluoroacetic acid,
TOF: Time-of-flight,
TSB: Tryptic soy broth,
UV: Ultra violet.

LITERATURE

The following non-patent-literature is cited in the application:

1. Thomasz, A. (1994) Multiple-antibiotic-resistant bacteria. *New Engl. J. Med.* 330: 1247-1251.
2. Wenzel, R. P. (1988) The mortality of hospital-acquired bloodstream infections: need for a vital statistic? *Int. J. Epidemiol.* 17: 225-227.
3. Moellering, R. C, Jr. (1998) Problems with antimicrobial resistance in Gram-positive cocci. *Clin. Infect. Dis.* 26: 1177-1178.
4. Hand, W. L. (2000) Current challenges in antibiotic resistance. *Adolesc. Med.* 11: 427-438.
5. Hooper, D. C. (2001) Emerging mechanisms of fluoroquinolone resistance. *Emerg. Infect. Dis.* 7: 337-341.
6. Jones, R. N. (2001) Resistance patterns among nosocomial pathogens: trends over the past few years. *Chest* 119: 397S-404S.
7. Prachayasittikul, V., Lawung, R., and Bulow, L. (2000) Episome profiles and mobilizable beta lactamase plasmid in *Haemophilus ducreyi*. *Southeast Asian J. Trop. Med. Public Health* 31: 80-84.
8. Teuber, M. (1999) Spread of antibiotic resistance with food-borne pathogens. *Cell. Mol. Life Sci.* 30: 755-763.
9. Boman, H. G. (1995) Peptide antibiotics and their role in innate immunity. *Annu. Rev. Immunol.* 13: 61-92.
10. Barra, D., Simmaco, M., and Boman, H. G. (1998) Gene encoded peptide antibiotics and innate immunity. Do 'animacules' have defense budgets? *FEBS Lett.* 430: 130-134.
11. Ludtke, S., He, K., and Huang, H. (1995) Membrane thinning caused by magainin 2. *Biochemistry* 34: 16764-16769.
12. Wimley, W. C., Selsted, M. E., and White, S. H. (1994) Interactions between human defensins and lipid bilayers: evidence for formation of multimeric pores. *Protein Sci.* 3: 1361-1373.
13. Shai, Y. (1995) Molecular recognition between membrane-spanning polypeptides. *Trends Biochem. Sci.* 20: 460-464.
14. Wade, D., Boman, A., Wahlin, B., Drain, C. M., Andreu, D., Boman, H. G., and Merrifield, R. B. (1990) *Proc. Natl. Acad. Sci. USA* 87: 4761-4765.
15. Steiner, H., Andreu, D., and Merrifield, R. B. (1988) *Biochim. Biophys. Acta* 939: 260-266.
16. Otvos, L., Jr., Bokonyi, K., Varga, I., Otvos, B. I., Hoffmann, R., Ertl, H. C. J., Wade, J. D., McManus, A. M., Craik, D. J., and Bulet, P. (2000) Insect peptides with improved protease-resistance protect mice against bacterial infection. *Protein Sci.* 9: 742-749.
17. Boman, H. G. (1995) Peptide antibiotics and their role in innate immunity. *Annu. Rev. Immunol.* 13: 61-92.
18. Casteels, P., Ampe, C., Jacobs, F., Vaeck, M., and Tempst, P. (1989) Apidaecins: antibacterial peptides from honeybees. *EMBO J.* 8: 2387-2391.
19. Casteels, P., and Tempst, P. (1994) Apidaecin-type peptide antibiotics function through a non-poreforming mechanism involving stereospecificity. *Biochem. Biophys. Res. Commun.* 199: 339-45.
20. Bulet, P., Dimarcq, J.-L., Hetru, C., Lagueux, M., Charlet, M., Hegy, G., van Dorsselaer, A., and Hoffmann, J. A. (1993) A novel inducible antibacterial peptide from *Drosophila* carries an O-glycosylated substitution. *J. Biol. Chem.* 268: 14893-14897.
21. Mackintosh, J. A., Veal, D. A., Beattie, A. J., and Gooley, A. A. (1998) Isolation from an ant *Myrmecia gulosa* of two inducible O-glycosylated proline-rich antibacterial peptides. *J. Biol. Chem.* 273: 6139-6143.
22. Cociancich, S., Dupont, A., Hegy, G., Lanot, R., Holder, F., Hetru, C., Hoffmann, J. A., and Bulet P. (1994) Novel inducible antibacterial peptides from a hemipteran insect, the sap sucking-bug *Pyrrhocoris apterus*. *Biochem. J.* 300: 567-575.
23. Merrifield, R. B. (1963) Solid Phase Peptide Synthesis. I. The Synthesis of a Tetrapeptide J. Am. Chem. Soc. 85: 2149-2154
24. Stemmer, W. P., Crameri, A., Ha, K. D., Brennan, T. M., Heyneker, H. L. (1995) Single-step assembly of a gene and entire plasmid from large numbers of oligodeoxyribonucleotides. Gene 164: 49-53.
25. Gething, M. J. and Sambrook, J. (1981) Cell-surface expression of influenza haemagglutinin from a cloned DNA copy of the RNA gene. Nature. 293: 620-625.

26. Maeno, M., Taguchi, S., Momose, H. (1993) Production of antibacterial peptide 'apidaecin' using the secretory expression system of *Streptomyces*. Biosci. Biotechnol. Biochem. 57: 1206-1207.
27. Zhou, Q. F., Luo, X. G., Ye, L., Xi, T. (2007) High-level production of a novel antimicrobial peptide perinerin in *Escherichia coli* by fusion expression. Curr. Microbiol. 54: 366-370.
28. Si, L. G., Liu, X. C., Lu, Y. Y., Wang, G. Y., Li, W. M. (2007) Soluble expression of active human beta-defensin-3 in *Escherichia coli* and its effects on the growth of host cells. Chin. Med. J. (Engl). 120: 708-713.
29. Noren, C. J., Anthony-Cahill, S. J., Griffith, M. C. and Schultz, P. G. (1989) A general method for site-specific incorporation of unnatural amino acids into proteins. *Science* 244: 182-188.
30. Ellman, J., Mendel, D., Anthony-Cahill, S., Noren, C. J., Schultz, P. G. (1991) Biosynthetic method for introducing unnatural amino acids site-specifically into proteins. *Meth. Enzymol.* 202: 301-336.
31. W. F. Anderson (1998) Human gene therapy. *Nature* 392 Supp., 25-30
32. Pharmaceutical Biotechnology (Ed. D. J. A. Crommelin and R. D. Sindelar), Harwood Academic Publishers, 1997, pp. 8-20, 53-70, 123-152, 167-180.
33. Protein Synthesis: Methods and Protocols, Ed. R. Martin, Humana Press, 1998, pp. 1-442.
34. Amino Acid and Peptide Synthesis, Oxford University Press, 1997, pp. 1-89.
35. Solid-Phase Peptide Synthesis (Ed. G. B. Fields) Academic Press, 1997, p. 1-780
36. Tam, J. P. (1998) Synthetic Peptide Vaccine Design: Synthesis and Properties of a High-Density Multiple Antigenic Peptide System, *Proc. Natl. Acad. Sci. USA* 85: 5409-5413.
37. Posnett, D. N., McGrath, H. and Tam, J. P. (1988) A novel method for producing anti-peptide antibodies. Production of site-specific antibodies to the T cell antigen receptor beta-chain. *J. Biol. Chem.* 263: 1719-1725.
38. Morell, M., Espargaró, A., Avilés, F. X. and Ventura, S. (2007) Detection of transient protein-protein interactions by bimolecular fluorescence complementation: The Ab1-SH3 case. Proteomics 7: 1023-1036.
39. G. B. Fields and Noble, R. (1990) Solid phase peptide synthesis utilizing 9-fluorenylmethoxycarbonyl amino acids. *Int. J. Pept. Protein Res.* 35: 161-214
40. Gausepohl, H., Pieles, H., Frank, R. W. (1992) in "Peptides: chemistry, structure and biology" (ed. J. A. Smith and J. E. Rivier), p. 523, ESCOM, Leiden.
41. Fmoc Solid Phase Peptide Synthesis (Ed. W. C. Chan and P. D. White) in The Practical Approaches Series (Ed. B. D. Hames), University Press, Oxford, p. 63.
42. Hoffmann, R., Vasko M. and Otvos, L., Jr. 1997. Serum stability of phosphopeptides. *Anal. Chim. Acta* 352: 319-325.
43. Ryge, T. S. and Hansen, P. R. (2006) Potent antibacterial lysine-peptoid hybrids identified from a positional scanning combinatorial library. *Bioorg. Med. Chem.* 14: 4444-4451
44. Park, Y., Lee, D. G., Jang, S. H., Woo, E. R., Jeong, H. G., Choi, C. H., and Hahm, V. S. (2003). A Leu-Lys-rich antimicrobial peptide: activity and mechanism. *Biochim. Biophys. Acta* 1645: 172-182.

---

The invention claimed is:

1. A peptide or peptide derivative with at least 16 residues and the general formula $$\text{Sub}_1\text{-}X_1 \text{ N } X_2 \text{ } X_3 \text{ P V Y I P } X_4 \text{ } X_5 \text{ R P P H P-Sub}_2 \text{ (SEQ ID NO: 169)}$$

wherein
- $X_1$ is a residue having a net positive charge or a positively charged side chain under physiological conditions;
- $X_2$ is a residue with a polar side chain or a residue having a net positive charge or a positively charged side chain under physiological conditions;
- $X_3$ is a residue having a net positive charge or a positively charged side chain under physiological conditions;
- $X_4$ is a neutral residue with a polar side chain or a residue having a net positive charge or a positively charged side chain under physiological conditions;
- $X_5$ is proline or a proline derivative;
- $\text{Sub}_1$ being a guanidination modification of the N-terminal amino group;
- $\text{Sub}_2$ being the free C-terminal carboxyl group of the C-terminal amino acid or a modification of the C-terminal carboxyl group, wherein the peptide or peptide derivative exhibits one or more of increased antibacterial and/or antifungal potency, increased mammalian serum stability, increased protease resistance, decreased toxicity to mammalian cells, decreased induction of resistance in microorganisms, and enlarged spectrum of antimicrobial activity, relative to lacking $\text{Sub}_1$.

2. The peptide or peptide derivative according to claim 1, comprising at least one additional residue $X_6$ and/or $X_7$ in $\text{Sub}_2$, whereas $X_6$ is selected from proline, a proline derivative, or a residue having a net positive charge or a positively charged side chain under physiological conditions and $X_7$ is selected from the proline, proline derivatives, a polar residue or a hydrophobic residue.

3. The peptide or peptide derivative according to claim 1, whereas the residue $X_1$ is selected from the group consisting of arginine, lysine, δ-hydroxylysine, homoarginine, D-arginine, methylarginine, nitroarginine, nitrosoarginine, arginal, guanidino propionic acid, 2,4-diaminobutyric acid, β-homoarginine, ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, histidine, 1-methyl-histidine, 3-methyl-histidine, 3-amino-tyrosine, alpha-N-methylarginine, N(G)-nitroarginine and N(G)-nitrosoarginine.

4. The peptide or peptide derivate according to claim 1, whereas the residue $X_2$ is selected from the group consisting of serine, threonine, homoserine, allo-threonine, citrulline, arginine, lysine, δ-hydroxylysine, homoarginine, D-arginine, methylarginine, nitrosoarginine, nitroarginine, arginal, guanidino propionic acid, 2,4-diaminobutyric acid, β-homoarginine, ε-N-methyllysine, allo-hydroxylysine, 2,3-diaminopropionic acid, 2,2'-diaminopimelic acid, ornithine, sym-dimethylarginine, asym-dimethylarginine and 2,6-diaminohexynoic acid.

5. The peptide or peptide derivate according to claim 1, whereas the residue $X_3$ is selected from the group consisting of arginine, lysine, δ-hydroxylysine, homoarginine, 2,4-diaminobutyric acid, P-homoarginine, —N-methyllysine, allo-hydroxylysine, 2,3-diaminopropionic acid, 2,2'-diaminopimelic acid, lysine, arginine, ornithine, methylarginine, sym-dimethylarginine, asym-dimethylarginine, nitroarginine, nitrosoarginine, arginal, guanidino propionic acid, 2,6-diaminohexynoic acid, histidine, 1-methyl-histidine, 3-methyl-histidine, and 3-amino-tyrosine.

6. The peptide or peptide derivative according to claim 1, whereas the residue $X_4$ is selected from the group consisting of asparagine, N-methylserine, N-methylglycine, dihydroxyphenylalanine, N-ethylasparagine, N-ethylglycine, homoserine, penicillamine, tetrahydropyranylglycine, allo-threonine, 3,5-dinitrotyrosine, citrulline, arginine, lysine, δ-hydroxylysine, homoarginine, 2,4-diaminobutyric acid, β-homoarginine, ε-N-methyllysine, allo-hydroxylysine, 2,3-diaminipropionic acid, 2,2'-diaminopimelic acid, ornithine, methylarginine, sym-dimethylarginine, asym-dimethylarginine, nitroarginine, nitrosoarginine, arginal, guanidino propionic acid, 2,6-diaminohexynoic acid, histidine, 1-methyl-histidine, 3-methyl-histidine, and 3-amino-tyrosine.

7. The peptide or peptide derivative according to claim 1, whereas the residue $X_5$ is proline or a proline, selected from the group consisting of cis-4-hydroxyproline, trans-4-hydroxyproline, cis-3-bydroxyproline, trans-3-hydroxyproline, β-cyclohexylalanine, 3,4-cis-methanoproline, 3,4-dehydroproline, homoproline and pseudoproline.

8. The peptide or peptide derivative according to claim 2, whereas the residue $X_6$ is selected from the group consisting of proline, cis-4-hydroxyproline, trans-4-hydroxyproline, cis-3-hydroxyproline, trans-3-hydroxyproline, β-cyclohexylalanine, 3,4-cis-methanoproline, 3,4-dehydroproline, homoproline pseudoprolines, arginine, D-arginine, δ-hydroxylysine, homoarginine, 2,4-diaminobutyric acid, β-homoarginine, ε-N-methyllysine, allo-hydroxylysine, 2,3-diaminipropionic acid, 2,2'-diaminopimelic acid, lysine, ornithine, methylarginine, sym-dimethylarginine, asym-dimethylarginine, nitroarginine, nitrosoarginine, arginal, guanidino propionic acid, 2,6-diaminohexynoic acid, histidine, 1-methyl-histidine, 3-methyl-histidine, and 3-amino-tyrosine.

9. The peptide or peptide derivative according to claim 2, whereas the residue $X_7$ is selected from the group consisting of proline, cis-4-hydroxyproline, trans-4-hydroxyproline, cis-3-hydroxyproline, trans-3-hydroxyproline, β-cyclohexylalanine, 3,4-cis-methanoproline, 3,4-dehydroproline, homoproline, pseudoprolines, serine, threonine, citrulline, N-methylserine, N-methylglycine, dihydroxyphenylalanine, N-ethylasparagine, N-ethylglycine, homoserine, penicillamine, tetrahydropyranylglycine, allo-threonine, 3,5-dinitrotyrosine, δ-hydroxylysine, phenylalanine, leucine, isoleucine, valine, methionine, alanine, 1-amino-cylcohexyl carbonic acid, N-methylleucine, N-methylisoleucine, tert.-butylglycine, β-alanine, norleucine, norvaline, N-methylvaline, 6-aminocaproic acid, 2-aminoheptanoic acid, 2-aminoisobutyric acid, 3-aminoisobutyric acid, aminovaleric acid, 2-aminopimelic acid, pipecolonic acid, tryptophan, iodo-tyrosine, 3,5-diiodo-tyrosine, 3,5-dibromo-tyrosine, β-cyclohexylalanine, p-aminobenzoic acid, ε-aminocaproic acid, 3,4-cis-methanoproline, phenylglycine, 3,4-dehydroproline, 4-amino-5-cyclohexyl-3-hydroxypentanoic acid, O-phosphotyrosine, O-sulfotyrosine, aminoethylpyrrolecarboxylic acid, 4-aminopiperidine-4-carboxylic acid, α-aminoadipic acid, homoproline, homophenylalanine, p-fluoro-phenylalanine, 3,4-dichlorophenylalanine, p-bromo-phenylalanine, p-iodo-phenylalanine, and p-nitrophenylalanine.

10. The peptide or peptide derivative according to claim 2, selected from the sequences according to any one of SEQ ID NO: 88, 120, 125, 134, 137, 146, 147, 151 and 155 to 158.

11. The peptide or peptide derivate according to claim 1, wherein $X_1$ is ornithine.

12. The peptide or peptide derivate according to claim 1, wherein $Sub_1$ is $N(CH_3)_2$—$(C$—$N^+(CH_3)_2)$—$NH$—).

13. A multimer comprising at least two peptides or peptide derivatives coupled together wherein at least one of the peptides or peptide derivatives is a peptide or peptide derivative according to claim 1.

14. A pharmaceutical composition comprising at least one of the peptides or peptide derivatives of claim 1 or a multimer according to claim 13.

15. A method of treating a microbial, bacterial or fungal infection in a mammal by administering to a mammal having said infection an amount of the peptide of claim 1.

16. A method for identifying a compound, which has a potential antimicrobial, bactericial or antifungal effect, comprising:
  (i) performing a competitive assay with:
    (a) a microorganism susceptible to the peptide or peptide derivative according to claim 1;
    (b) the peptide or peptide derivative according to claim 1; and
    (c) at least one compound to be tested;
    by exposing (a) to (b) and (c); and
  (ii) selecting a test compound which competitively displaces the binding of the peptide or peptide derivative to the microorganism.

17. The method according to claim 16, wherein the selected compound is further screened for anti-bacterial or antifungal use.

18. The method according to claim 16, wherein the microorganism is a species belonging to one of the genera selected from *Escherichia coli, Enterobacter cloacae, Erwinia amylovora, Klebsiella pneumoniae, Morganella morganii, Salmonella typhimurium, Salmonella typhi, Shigella dysenteriae, Yersinia enterocolitica, Acinetobacter calcoaceticus, Agrobacterium tumefaciens, Francisella tularensis, Legionella pneumophila, Pseudomonas syringae, Rhizobium meliloti* and *Haemophilus influenzae*.

* * * * *

SEQUENCE LISTING

```
<160> NUMBER OF SEQ ID NOS: 172

<210> SEQ ID NO 1
<211> LENGTH: 18
<212> TYPE: PRT
<213> ORGANISM: Apis mellifera
<220> FEATURE:
<223> OTHER INFORMATION: C-term OH

<400> SEQUENCE: 1

Gly Asn Asn Arg Pro Val Tyr Ile Pro Gln Pro Arg Pro Pro His Pro
1               5                   10                  15

Arg Ile

<210> SEQ ID NO 2
<211> LENGTH: 18
<212> TYPE: PRT
<213> ORGANISM: Apis mellifera
<220> FEATURE:
<223> OTHER INFORMATION: C-term OH

<400> SEQUENCE: 2

Gly Asn Asn Arg Pro Val Tyr Ile Pro Gln Pro Arg Pro Pro His Pro
1               5                   10                  15

Arg Leu

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: N-term acetylated
<220> FEATURE:
<223> OTHER INFORMATION: C-term amidated

<400> SEQUENCE: 3

Gly Asn Asn Arg Pro Val Tyr Ile Pro Gln Pro Arg Pro Pro His Pro
1               5                   10                  15

Arg Ile

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 4

Gly Asn Asn Arg Pro Val Tyr Ile Pro Gln Pro Arg Pro Pro His Pro
1               5                   10                  15

Arg Ile

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 5

Gly Asn Asn Arg Pro Val Tyr Ile Pro Gln Pro Arg Pro Pro His Pro
1               5                   10                  15

Arg Leu

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 6

Gly Asn Asn Arg Pro Val Tyr Ile Pro Gln Pro Arg Pro Pro His Pro
1               5                   10                  15

Arg Leu

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated

```
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 7

Xaa Asn Asn Arg Pro Val Tyr Ile Pro Gln Pro Arg Pro Pro His Pro
1               5                   10                  15

Arg Leu

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 8

Xaa Asn Asn Arg Pro Val Tyr Ile Pro Gln Pro Arg Pro Pro His Pro
1               5                   10                  15

Arg Leu

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ornithine
<220> FEATURE:
<223> OTHER INFORMATION: C-term amidated

<400> SEQUENCE: 9

Gly Asn Asn Arg Pro Val Tyr Ile Pro Xaa Pro Arg Pro Pro His Pro
1               5                   10                  15

Arg Ile

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term OH

<400> SEQUENCE: 10

Gly Asn Asn Lys Pro Val Tyr Ile Pro Arg Pro Arg Pro Pro His Pro
1               5                   10                  15

Arg Leu Val

<210> SEQ ID NO 11
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ornithine
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 11

Gly Asn Asn Arg Pro Val Tyr Ile Pro Xaa Pro Arg Pro Pro His Pro
1               5                   10                  15

Arg Leu

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (10)..(10)
<223> OTHER INFORMATION: Ornithine
<220> FEATURE:
<223> OTHER INFORMATION: C-term amidated

<400> SEQUENCE: 12

Xaa Asn Asn Arg Pro Val Tyr Ile Pro Xaa Pro Arg Pro Pro His Pro
1               5                   10                  15

Arg Leu

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (10)..(10)
<223> OTHER INFORMATION: Ornithine
<220> FEATURE:
<223> OTHER INFORMATION: C-term amidated

<400> SEQUENCE: 13

Xaa Asn Asn Arg Pro Val Tyr Ile Pro Xaa Pro Arg Pro Pro His Pro
1               5                   10                  15

Arg Leu

<210> SEQ ID NO 14
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 14

Gly Asn Asn Arg Pro Val Tyr Ile Pro Arg Pro Arg Pro Pro His Pro
1               5                   10                  15

Arg Ile

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 15

Gly Asn Asn Arg Pro Val Tyr Ile Pro Arg Pro Arg Pro Pro His Pro
1               5                   10                  15

Arg Ile

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 16

Xaa Asn Asn Arg Pro Val Tyr Ile Pro Arg Pro Arg Pro Pro His Pro
1               5                   10                  15

Arg Ile

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 17

Gly Asn Asn Arg Pro Val Tyr Ile Pro Lys Pro Arg Pro Pro His Pro
1               5                   10                  15

Arg Ile
```

-continued

```
<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 18

Xaa Asn Asn Arg Pro Val Tyr Ile Pro Arg Pro Arg Pro Pro His Pro
1               5                   10                  15

Arg Ile

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4tHyp
<220> FEATURE:
<223> OTHER INFORMATION: C-term amidated

<400> SEQUENCE: 19

Gly Asn Asn Arg Pro Val Tyr Ile Pro Gln Pro Arg Pro Pro His Pro
1               5                   10                  15

Arg Ile

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 20

Gly Asn Asn Arg Pro Val Tyr Ile Pro Arg Pro Arg Pro Pro His Pro
1               5                   10                  15

Arg Leu

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 21
```

```
Lys Asn Asn Arg Pro Val Tyr Ile Pro Lys Pro Arg Pro Pro His Pro
1               5                   10                  15

Arg Leu

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 22

Lys Asn Asn Arg Pro Val Tyr Ile Pro Lys Pro Arg Pro Pro His Pro
1               5                   10                  15

Arg Leu

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term OH

<400> SEQUENCE: 23

Xaa Asn Asn Arg Pro Val Tyr Ile Pro Arg Pro Arg Pro Pro His Pro
1               5                   10                  15

Arg Pro Ile Arg Val
            20

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term OH

<400> SEQUENCE: 24

Xaa Asn Asn Arg Pro Val Tyr Ile Pro Arg Pro Arg Pro Pro His Pro
1               5                   10                  15

Arg Pro Ile Arg Val
            20

<210> SEQ ID NO 25
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 25

Gly Asn Asn Arg Pro Val Tyr Ile Pro Arg Pro Arg Pro Pro His Pro
1               5                   10                  15

Arg Leu Val

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 26

Gly Asn Asn Arg Pro Val Tyr Leu Pro Gln Pro Arg Pro Pro His Pro
1               5                   10                  15

Arg Ile

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 27

Xaa Asn Asn Arg Pro Val Tyr Ile Pro Arg Pro Arg Pro Pro His Pro
1               5                   10                  15

Arg Pro Ile Arg Val
            20

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 28

Xaa Asn Asn Arg Pro Val Tyr Ile Pro Arg Pro Arg Pro Pro His Pro
1               5                   10                  15

Arg Pro Ile Arg Val
            20
```

```
<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term OH

<400> SEQUENCE: 29

Xaa Asn Asn Arg Pro Val Tyr Ile Pro Gln Pro Arg Pro Pro His Pro
1               5                   10                  15

Arg Leu Val

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term OH

<400> SEQUENCE: 30

Xaa Asn Asn Arg Pro Val Tyr Ile Pro Gln Pro Arg Pro Pro His Pro
1               5                   10                  15

Arg Leu Val

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term OH

<400> SEQUENCE: 31

Gly Asn Asn Arg Pro Val Tyr Ile Pro Arg Pro Arg Pro Pro His Pro
1               5                   10                  15

Arg Leu Val

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
```

```
<221> NAME/KEY: MOD_RES
<222> LOCATION: (18)..(18)
<223> OTHER INFORMATION: MeLeu
<220> FEATURE:
<223> OTHER INFORMATION: C-term amidated

<400> SEQUENCE: 32

Xaa Asn Asn Arg Pro Val Tyr Ile Pro Gln Pro Arg Pro Pro His Pro
1               5                   10                  15

Arg Leu

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: MeLeu
<220> FEATURE:
<223> OTHER INFORMATION: C-term amidated

<400> SEQUENCE: 33

Gly Asn Asn Arg Pro Val Tyr Ile Pro Gln Pro Arg Pro Pro His Pro
1               5                   10                  15

Arg Leu

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: MeLeu
<220> FEATURE:
<223> OTHER INFORMATION: C-term amidated

<400> SEQUENCE: 34

Gly Asn Asn Arg Pro Val Tyr Ile Pro Arg Pro Arg Pro Pro His Pro
1               5                   10                  15

Arg Leu

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (10)..(10)
<223> OTHER INFORMATION: Ornithine
<220> FEATURE:
<221> NAME/KEY: MOD_RES
<222> LOCATION: (18)..(18)
<223> OTHER INFORMATION: Cha
<220> FEATURE:
<223> OTHER INFORMATION: C-term amidated
```

<400> SEQUENCE: 35

Xaa Asn Asn Arg Pro Val Tyr Ile Pro Xaa Pro Arg Pro Pro His Pro
1               5                   10                  15

Arg Ala

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (18)..(18)
<223> OTHER INFORMATION: MeLeu
<220> FEATURE:
<223> OTHER INFORMATION: C-term amidated

<400> SEQUENCE: 36

Xaa Asn Asn Arg Pro Val Tyr Ile Pro Arg Pro Arg Pro Pro His Pro
1               5                   10                  15

Arg Leu

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Cha
<220> FEATURE:
<223> OTHER INFORMATION: C-term amidated

<400> SEQUENCE: 37

Gly Asn Asn Arg Pro Val Tyr Ile Pro Arg Pro Arg Pro Pro His Pro
1               5                   10                  15

Arg Ala

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 38

Xaa Asn Asn Arg Pro Val Tyr Ile Pro Arg Pro Arg Pro Pro His Pro
1               5                   10                  15

Arg Leu

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 39

Xaa Asn Asn Arg Pro Val Tyr Ile Pro Arg Pro Arg Pro Pro His Pro
1               5                   10                  15

Arg Leu

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 40

Xaa Asn Asn Arg Pro Val Tyr Ile Pro Arg Pro Arg Pro Pro His Pro
1               5                   10                  15

Arg Leu

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 41

Xaa Asn Asn Arg Pro Val Tyr Ile Pro Gln Pro Arg Pro Pro His Pro
1               5                   10                  15

Arg Phe

<210> SEQ ID NO 42

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 42

Xaa Asn Asn Arg Pro Val Tyr Ile Pro Gln Pro Arg Pro Pro His Pro
1               5                   10                  15

Arg Phe

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 43

Gly Asn Asn Arg Pro Val Tyr Ile Pro Gln Pro Arg Pro Pro His Pro
1               5                   10                  15

Leu

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 44

Gly Asn Asn Arg Pro Val Tyr Ile Pro Gln Pro Arg Pro Pro His Pro
1               5                   10                  15

Arg Phe

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 45

Xaa Asn Asn Arg Pro Val Tyr Ile Pro Arg Pro Arg Pro Pro His Pro
1               5                   10                  15
```

Arg Leu

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (10)..(10)
<223> OTHER INFORMATION: Ornithine
<220> FEATURE:
<221> NAME/KEY: MOD_RES
<222> LOCATION: (18)..(18)
<223> OTHER INFORMATION: Cha
<220> FEATURE:
<223> OTHER INFORMATION: C-term amidated

<400> SEQUENCE: 46

Xaa Asn Asn Arg Pro Val Tyr Ile Pro Xaa Pro Arg Pro Pro His Pro
1               5                   10                  15

Arg Ala

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (18)..(18)
<223> OTHER INFORMATION: MeLeu
<220> FEATURE:
<223> OTHER INFORMATION: C-term amidated

<400> SEQUENCE: 47

Xaa Asn Asn Arg Pro Val Tyr Ile Pro Arg Pro Arg Pro Pro His Pro
1               5                   10                  15

Arg Leu

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term Ome

<400> SEQUENCE: 48

```
Xaa Asn Asn Arg Pro Val Tyr Ile Pro Arg Pro Arg Pro His Pro
1               5                   10                  15

Arg Leu

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (10)..(10)
<223> OTHER INFORMATION: Ornithine
<220> FEATURE:
<223> OTHER INFORMATION: C-term Ome

<400> SEQUENCE: 49

Xaa Asn Asn Arg Pro Val Tyr Ile Pro Xaa Pro Arg Pro Pro His Pro
1               5                   10                  15

Arg Leu

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term Ome

<400> SEQUENCE: 50

Xaa Asn Asn Arg Pro Val Tyr Ile Pro Gln Pro Arg Pro Pro His Pro
1               5                   10                  15

Arg Leu

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 51

Gly Asn Asn Arg Pro Val Tyr Ile Pro Gln Pro Arg Pro Pro Lys Pro
1               5                   10                  15

Arg Ile

<210> SEQ ID NO 52
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 52

Gly Asn Asn Arg Pro Val Tyr Ile Pro Gln Pro Arg Pro Pro Lys Pro
1               5                   10                  15

Arg Pro

<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 53

Gly Asn Asn Arg Pro Val Tyr Ile Pro Gln Pro Arg Pro Pro Arg Pro
1               5                   10                  15

Arg Ile

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 54

Gly Asn Asn Arg Pro Val Tyr Ile Pro Gln Pro Arg Pro Pro His Pro
1               5                   10                  15

Arg Pro Ile

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 55

Gly Asn Asn Arg Pro Val Tyr Leu Pro Arg Pro Arg Pro Pro His Pro
1               5                   10                  15

Arg Ile

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
```

```
<400> SEQUENCE: 56

Gly Asn Asn Arg Pro Val Tyr Leu Pro Lys Pro Arg Pro Pro His Pro
1               5                   10                  15

Arg Ile

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 4tHyp
<220> FEATURE:
<223> OTHER INFORMATION: C-term amidated

<400> SEQUENCE: 57

Gly Asn Asn Arg Pro Val Tyr Ile Pro Gln Pro Arg Pro Pro His Pro
1               5                   10                  15

Arg Ile

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 58

Gly Asn Asn Arg Pro Val Tyr Ile Pro Gln Pro Arg Pro Pro His Pro
1               5                   10                  15

Arg Ile

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: 4tHyp
<220> FEATURE:
<223> OTHER INFORMATION: C-term amidated

<400> SEQUENCE: 59

Gly Asn Asn Arg Pro Val Tyr Ile Pro Gln Pro Arg Pro Pro His Pro
1               5                   10                  15

Arg Ile

<210> SEQ ID NO 60
<211> LENGTH: 18
<212> TYPE: PRT
<213> ORGANISM: Artificial Sequence
```

<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: 4tHyp
<220> FEATURE:
<223> OTHER INFORMATION: C-term amidated

<400> SEQUENCE: 60

Gly Asn Asn Arg Pro Val Tyr Ile Pro Gln Pro Arg Pro Pro His Pro
1               5                   10                  15

Arg Ile

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: 4tHyp
<220> FEATURE:
<223> OTHER INFORMATION: C-term amidated

<400> SEQUENCE: 61

Gly Asn Asn Arg Pro Val Tyr Ile Pro Gln Pro Arg Pro Pro His Pro
1               5                   10                  15

Arg Ile

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 62

Xaa Asn Asn Arg Pro Val Tyr Ile Pro Gln Pro Arg Pro Pro His Pro
1               5                   10                  15

Arg Ile

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 63

Xaa Asn Asn Arg Pro Val Tyr Ile Pro Gln Pro Arg Pro Pro His Pro
1               5                   10                  15

Arg Ile

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 64

Xaa Asn Asn Arg Pro Val Tyr Ile Pro Arg Pro Arg Pro Pro His Pro
1               5                   10                  15

Arg Ile

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 65

Xaa Asn Asn Arg Pro Val Tyr Ile Pro Arg Pro Arg Pro Pro His Pro
1               5                   10                  15

Arg Ile

<210> SEQ ID NO 66
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 66

Gly Asn Asn Arg Pro Val Tyr Ile Pro Arg Pro Arg Pro Pro His Pro
1               5                   10                  15

Arg Leu

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: N-term acetylated
<220> FEATURE:
<223> OTHER INFORMATION: C-term amidated

<400> SEQUENCE: 67

Gly Asn Asn Arg Pro Val Tyr Ile Pro Arg Pro Arg Pro Pro His Pro
1               5                   10                  15

Arg Leu

<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 68

Gly Asn Asn Lys Pro Val Tyr Ile Pro Arg Pro Arg Pro Pro His Pro
1               5                   10                  15

Arg Leu Val

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term OH

<400> SEQUENCE: 69

Gly Asn Asn Arg Pro Val Tyr Ile Pro Arg Pro Arg Pro Pro His Pro
1               5                   10                  15

Arg Leu Val

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term OH

<400> SEQUENCE: 70

Gly Asn Asn Arg Pro Val Tyr Ile Pro Gln Pro Arg Pro Pro His Pro
1               5                   10                  15

Arg Pro Ile Arg Val
            20

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
```

```
<223> OTHER INFORMATION: Ornithine
<220> FEATURE:
<221> NAME/KEY: MOD_RES
<222> LOCATION: (18)..(18)
<223> OTHER INFORMATION: Cha
<220> FEATURE:
<223> OTHER INFORMATION: C-term amidated

<400> SEQUENCE: 71

Xaa Asn Asn Arg Pro Val Tyr Ile Pro Gln Pro Arg Pro Pro His Pro
1               5                   10                  15

Arg Ala

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (18)..(18)
<223> OTHER INFORMATION: D-Leu
<220> FEATURE:
<223> OTHER INFORMATION: C-term amidated

<400> SEQUENCE: 72

Xaa Asn Asn Arg Pro Val Tyr Ile Pro Gln Pro Arg Pro Pro His Pro
1               5                   10                  15

Arg Leu

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (18)..(18)
<223> OTHER INFORMATION: Tert-Gly
<220> FEATURE:
<223> OTHER INFORMATION: C-term amidated

<400> SEQUENCE: 73

Xaa Asn Asn Arg Pro Val Tyr Ile Pro Gln Pro Arg Pro Pro His Pro
1               5                   10                  15

Arg Gly

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (18)..(18)
<223> OTHER INFORMATION: Beta-Ala
<220> FEATURE:
<223> OTHER INFORMATION: C-term amidated

<400> SEQUENCE: 74

Xaa Asn Asn Arg Pro Val Tyr Ile Pro Gln Pro Arg Pro Pro His Pro
1               5                   10                  15

Arg Ala

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (18)..(18)
<223> OTHER INFORMATION: Chex
<220> FEATURE:
<223> OTHER INFORMATION: C-term amidated

<400> SEQUENCE: 75

Xaa Asn Asn Arg Pro Val Tyr Ile Pro Gln Pro Arg Pro Pro His Pro
1               5                   10                  15

Arg Xaa

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Cha
<220> FEATURE:
<223> OTHER INFORMATION: C-term amidated

<400> SEQUENCE: 76

Gly Asn Asn Arg Pro Val Tyr Ile Pro Gln Pro Arg Pro Pro His Pro
1               5                   10                  15

Arg Ala

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (18)..(18)
<223> OTHER INFORMATION: D-Leu
<220> FEATURE:
<223> OTHER INFORMATION: C-term amidated

<400> SEQUENCE: 77

Gly Asn Asn Arg Pro Val Tyr Ile Pro Gln Pro Arg Pro Pro His Pro
1               5                   10                  15

Arg Leu

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Tert-Gly
<220> FEATURE:
<223> OTHER INFORMATION: C-term amidated

<400> SEQUENCE: 78

Gly Asn Asn Arg Pro Val Tyr Ile Pro Gln Pro Arg Pro Pro His Pro
1               5                   10                  15

Arg Gly

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Beta-Ala
<220> FEATURE:
<223> OTHER INFORMATION: C-term amidated

<400> SEQUENCE: 79

Gly Asn Asn Arg Pro Val Tyr Ile Pro Gln Pro Arg Pro Pro His Pro
1               5                   10                  15

Arg Ala

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Chex
<220> FEATURE:
<223> OTHER INFORMATION: C-term amidated

<400> SEQUENCE: 80

Gly Asn Asn Arg Pro Val Tyr Ile Pro Gln Pro Arg Pro Pro His Pro
1               5                   10                  15

Arg Xaa
```

```
<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Ornithine
<220> FEATURE:
<223> OTHER INFORMATION: C-term amidated

<400> SEQUENCE: 81

Xaa Asn Asn Arg Pro Val Tyr Ile Pro Arg Pro Arg Pro Pro His Pro
1               5                   10                  15

Xaa Leu

<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Ornithine
<220> FEATURE:
<223> OTHER INFORMATION: C-term amidated

<400> SEQUENCE: 82

Xaa Asn Asn Arg Pro Val Tyr Ile Pro Arg Pro Arg Pro Pro His Pro
1               5                   10                  15

Xaa Leu

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: misc_feature
<222> LOCATION: (1)..(18)
<223> OTHER INFORMATION: Dipeptide

<400> SEQUENCE: 83

Xaa Asn Asn Arg Pro Val Tyr Ile Pro Arg Pro Arg Pro Pro His Pro
1               5                   10                  15

Arg Leu
```

```
<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term For
<220> FEATURE:
<223> OTHER INFORMATION: C-term amidated

<400> SEQUENCE: 84

Gly Asn Asn Arg Pro Val Tyr Ile Pro Gln Pro Arg Pro Pro His Pro
1               5                   10                  15

Arg Leu

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<223> OTHER INFORMATION: C-term amidated

<400> SEQUENCE: 85

Gly Asn Asn Arg Pro Val Tyr Ile Pro Gln Pro Arg Pro Pro His Pro
1               5                   10                  15

Arg Leu

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 86

Xaa Asn Asn Arg Pro Val Tyr Ile Pro Arg Pro Arg Pro Pro His Pro
1               5                   10                  15

Arg Pro Ile Arg Val
            20

<210> SEQ ID NO 87
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
```

<223> OTHER INFORMATION: C-term amidated

<400> SEQUENCE: 87

Xaa Asn Asn Arg Pro Val Tyr Ile Pro Arg Pro Arg Pro Pro His Pro
1               5                   10                  15

Arg Pro Ile Arg Val
            20

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 88

Xaa Asn Asn Arg Pro Val Tyr Ile Pro Arg Pro Arg Pro Pro His Pro
1               5                   10                  15

Arg Leu

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Cit
<220> FEATURE:
<223> OTHER INFORMATION: C-term amidated

<400> SEQUENCE: 89

Gly Asn Asn Arg Pro Val Tyr Ile Pro Xaa Pro Arg Pro Pro His Pro
1               5                   10                  15

Arg Ile

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 90

Gly Asn Asn Arg Pro Val Tyr Ile Pro Arg Pro Arg Pro Pro His Pro
1               5                   10                  15

Arg Ile

```
<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Cit
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 91

Gly Asn Asn Arg Pro Val Tyr Ile Pro Xaa Pro Arg Pro Pro His Pro
1               5                   10                  15

Arg Ile

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 92

Asn Asn Arg Pro Val Tyr Ile Pro Gln Pro Arg Pro Pro His Pro Arg
1               5                   10                  15

Ile

<210> SEQ ID NO 93
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 93

Gly Asn Asn Arg Pro Val Tyr Ile Pro Gln Pro Arg Pro Pro Pro Pro
1               5                   10                  15

Arg Pro

<210> SEQ ID NO 94
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 94

Gly Asn Asn Arg Pro Val Tyr Ile Pro Gln Pro Arg Pro Pro Lys Pro
1               5                   10                  15

Arg Pro Ile
```

<210> SEQ ID NO 95
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: C-term amidated

<400> SEQUENCE: 95

Gly Asn Asn Lys Pro Val Tyr Ile Pro Gln Pro Arg Pro Pro His Pro
1               5                   10                  15

Arg Leu

<210> SEQ ID NO 96
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: C-term amidated

<400> SEQUENCE: 96

Gly Asn Ser Arg Pro Val Tyr Ile Pro Gln Pro Arg Pro Pro His Pro
1               5                   10                  15

Arg Leu Val

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: C-term amidated

<400> SEQUENCE: 97

Gly Asn Ser Lys Pro Val Tyr Ile Pro Arg Pro Arg Pro Pro His Pro
1               5                   10                  15

Arg Leu

<210> SEQ ID NO 98
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (10)..(10)
<223> OTHER INFORMATION: Beta-Har
<220> FEATURE:
<223> OTHER INFORMATION: C-term amidated

<400> SEQUENCE: 98

Gly Asn Asn Arg Pro Val Tyr Ile Pro Arg Pro Arg Pro Pro His Pro
1               5                   10                  15

Arg Ile

<210> SEQ ID NO 99
<211> LENGTH: 18

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Beta-Har
<220> FEATURE:
<223> OTHER INFORMATION: C-term amidated

<400> SEQUENCE: 99

Gly Asn Asn Arg Pro Val Tyr Ile Pro Arg Pro Arg Pro Pro His Pro
1               5                   10                  15

Arg Leu

<210> SEQ ID NO 100
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 100

Gly Asn Asn Lys Pro Val Tyr Ile Pro Arg Pro Arg Pro Pro His Pro
1               5                   10                  15

Arg Leu

<210> SEQ ID NO 101
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 101

Gly Asn Ser Arg Pro Val Tyr Ile Pro Gln Pro Arg Pro Pro His Pro
1               5                   10                  15

Arg Leu

<210> SEQ ID NO 102
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (10)..(10)
<223> OTHER INFORMATION: Ornithine
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 102
```

```
Xaa Asn Asn Arg Pro Val Tyr Ile Pro Xaa Pro Arg Pro Pro His Pro
 1               5                  10                  15

Arg Leu

<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (10)..(10)
<223> OTHER INFORMATION: Ornithine
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 103

Xaa Asn Asn Arg Pro Val Tyr Ile Pro Xaa Pro Arg Pro Pro His Pro
 1               5                  10                  15

Arg Leu

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ornithine
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 104

Gly Asn Asn Arg Pro Val Tyr Ile Pro Xaa Pro Arg Pro Pro His Pro
 1               5                  10                  15

Arg Leu

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (11)..(11)
```

```
<223> OTHER INFORMATION: 4tHyp
<220> FEATURE:
<223> OTHER INFORMATION: C-term amidated

<400> SEQUENCE: 105

Xaa Asn Asn Arg Pro Val Tyr Ile Pro Gln Pro Arg Pro Pro His Pro
1               5                   10                  15

Arg Leu

<210> SEQ ID NO 106
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 106

Xaa Asn Asn Arg Pro Val Tyr Ile Pro Gln Pro Arg Pro Pro His Pro
1               5                   10                  15

Arg Leu

<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 107

Gly Asn Asn Arg Pro Val Tyr Ile Pro Gln Pro Arg Pro Pro His Pro
1               5                   10                  15

Arg Val

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term OH

<400> SEQUENCE: 108

Gly Asn Asn Arg Pro Val Tyr Ile Pro Gln Pro Arg Pro Pro His Pro
1               5                   10                  15

Arg Val

<210> SEQ ID NO 109
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 109

Gly Asn Asn Arg Pro Val Tyr Ile Pro Gln Pro Arg Pro Pro His Pro
1               5                   10                  15

Arg Pro Ile Pro Pro
            20

<210> SEQ ID NO 110
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 110

Gly Asn Asn Arg Pro Val Tyr Ile Pro Gln Pro Arg Pro Pro His Pro
1               5                   10                  15

Arg Pro Ile Arg Val
            20

<210> SEQ ID NO 111
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 111

Gly Asn Asn Arg Pro Val Tyr Ile Pro Gln Pro Arg Pro Pro His Pro
1               5                   10                  15

Pro Leu

<210> SEQ ID NO 112
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (10)..(10)
<223> OTHER INFORMATION: Ornithine
<220> FEATURE:
<223> OTHER INFORMATION: C-term amidated

<400> SEQUENCE: 112

Xaa Asn Asn Arg Pro Val Tyr Ile Pro Xaa Pro Arg Pro Pro His Pro
1               5                   10                  15

Pro Leu
```

```
<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (10)..(10)
<223> OTHER INFORMATION: Ornithine
<220> FEATURE:
<223> OTHER INFORMATION: C-term amidated

<400> SEQUENCE: 113

Xaa Asn Asn Arg Pro Val Tyr Ile Pro Xaa Pro Arg Pro Pro His Pro
1               5                   10                  15

Pro Leu

<210> SEQ ID NO 114
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 114

Gly Asn Asn Arg Pro Val Tyr Ile Pro Gln Pro Arg Pro Pro His Pro
1               5                   10                  15

Arg Tyr

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 115

Gly Asn Asn Arg Pro Val Tyr Ile Pro Gln Pro Arg Pro Pro His Pro
1               5                   10                  15

Arg

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term Ome
```

<400> SEQUENCE: 116

Xaa Asn Asn Arg Pro Val Tyr Ile Pro Gln Pro Arg Pro Pro His Pro
1               5                   10                  15

Arg Ile

<210> SEQ ID NO 117
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (10)..(10)
<223> OTHER INFORMATION: Ornithine
<220> FEATURE:
<223> OTHER INFORMATION: C-term Ome

<400> SEQUENCE: 117

Xaa Asn Asn Arg Pro Val Tyr Ile Pro Xaa Pro Arg Pro Pro His Pro
1               5                   10                  15

Arg Ile

<210> SEQ ID NO 118
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term Ome

<400> SEQUENCE: 118

Xaa Asn Asn Arg Pro Val Tyr Ile Pro Arg Pro Arg Pro Pro His Pro
1               5                   10                  15

Arg Ile

<210> SEQ ID NO 119
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: misc_feature
<222> LOCATION: (1)..(18)
<223> OTHER INFORMATION: Dipeptide

<400> SEQUENCE: 119

Xaa Asn Asn Arg Pro Val Tyr Ile Pro Arg Pro Arg Pro Pro His Pro
1               5                   10                  15

Arg Leu

<210> SEQ ID NO 120
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 120

Xaa Asn Asn Arg Pro Val Tyr Ile Pro Gln Pro Arg Pro Pro His Pro
1               5                   10                  15

Arg Leu

<210> SEQ ID NO 121
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Beta-Har
<220> FEATURE:
<223> OTHER INFORMATION: C-term amidated

<400> SEQUENCE: 121

Xaa Asn Asn Arg Pro Val Tyr Ile Pro Gln Pro Arg Pro Pro His Pro
1               5                   10                  15

Arg Leu

<210> SEQ ID NO 122
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(18)
<223> OTHER INFORMATION: Dipeptide

<400> SEQUENCE: 122

Gly Asn Asn Arg Pro Val Tyr Ile Pro Arg Pro Arg Pro Pro His Pro
1               5                   10                  15

Arg Leu

<210> SEQ ID NO 123
<211> LENGTH: 18
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: misc_feature
<222> LOCATION: (1)..(18)
<223> OTHER INFORMATION: Dipeptide

<400> SEQUENCE: 123

Gly Asn Asn Arg Pro Val Tyr Ile Pro Arg Pro Arg Pro Pro His Pro
1               5                   10                  15

Arg Leu

<210> SEQ ID NO 124
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: misc_feature
<222> LOCATION: (1)..(18)
<223> OTHER INFORMATION: Dipeptide

<400> SEQUENCE: 124

Xaa Asn Asn Arg Pro Val Tyr Ile Pro Arg Pro Arg Pro Pro His Pro
1               5                   10                  15

Arg Leu

<210> SEQ ID NO 125
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<221> NAME/KEY: misc_feature
<222> LOCATION: (1)..(18)
<223> OTHER INFORMATION: Dipeptide

<400> SEQUENCE: 125

Xaa Asn Asn Arg Pro Val Tyr Ile Pro Arg Pro Arg Pro Pro His Pro
1               5                   10                  15

Arg Leu

<210> SEQ ID NO 126
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Ornithine
<220> FEATURE:
<223> OTHER INFORMATION: C-term OH

<400> SEQUENCE: 126

Xaa Asn Asn Arg Pro Val Tyr Ile Pro Arg Pro Arg Pro Pro His Pro
1               5                   10                  15

Arg Pro Ile Arg Val
            20

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Ornithine
<220> FEATURE:
<221> NAME/KEY: misc_feature
<222> LOCATION: (1)..(18)
<223> OTHER INFORMATION: Dipeptide

<400> SEQUENCE: 127

Xaa Asn Asn Arg Pro Val Tyr Ile Pro Arg Pro Arg Pro Pro His Pro
1               5                   10                  15

Xaa Leu

<210> SEQ ID NO 128
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Ornithine
<220> FEATURE:
<221> NAME/KEY: misc_feature
<222> LOCATION: (1)..(18)
<223> OTHER INFORMATION: Dipeptide

<400> SEQUENCE: 128

Xaa Asn Asn Arg Pro Val Tyr Ile Pro Arg Pro Arg Pro Pro His Pro
1               5                   10                  15

Xaa Leu

<210> SEQ ID NO 129
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: misc_feature
<222> LOCATION: (1)..(18)
<223> OTHER INFORMATION: Dipeptide

<400> SEQUENCE: 129

Gly Asn Asn Arg Pro Val Tyr Ile Pro Gln Pro Arg Pro Pro His Pro
1               5                  10                  15

Arg Leu

<210> SEQ ID NO 130
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: misc_feature
<222> LOCATION: (1)..(18)
<223> OTHER INFORMATION: Dipeptide

<400> SEQUENCE: 130

Gly Asn Asn Arg Pro Val Tyr Ile Pro Gln Pro Arg Pro Pro His Pro
1               5                  10                  15

Arg Leu

<210> SEQ ID NO 131
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Har
<220> FEATURE:
<223> OTHER INFORMATION: C-term amidated

<400> SEQUENCE: 131

Xaa Asn Asn Arg Pro Val Tyr Ile Pro Arg Pro Arg Pro Pro His Pro
1               5                  10                  15

Arg Leu

<210> SEQ ID NO 132
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
```

```
<222> LOCATION: (17)..(17)
<223> OTHER INFORMATION: Har
<220> FEATURE:
<223> OTHER INFORMATION: C-term amidated

<400> SEQUENCE: 132

Gly Asn Asn Arg Pro Val Tyr Ile Pro Gln Pro Arg Pro Pro His Pro
1               5                   10                  15

Arg Leu

<210> SEQ ID NO 133
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (17)..(17)
<223> OTHER INFORMATION: Har
<220> FEATURE:
<223> OTHER INFORMATION: C-term amidated

<400> SEQUENCE: 133

Gly Asn Asn Arg Pro Val Tyr Ile Pro Gln Pro Arg Pro Pro His Pro
1               5                   10                  15

Arg Leu

<210> SEQ ID NO 134
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Ornithine
<220> FEATURE:
<223> OTHER INFORMATION: C-term amidated

<400> SEQUENCE: 134

Xaa Asn Asn Arg Pro Val Tyr Ile Pro Arg Pro Arg Pro Pro His Pro
1               5                   10                  15

Xaa Leu

<210> SEQ ID NO 135
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PEG
<220> FEATURE:
<221> NAME/KEY: MOD_RES
<222> LOCATION: (1)..(1)
<223> OTHER INFORMATION: Ornithine
<220> FEATURE:
```

<223> OTHER INFORMATION: C-term amidated

<400> SEQUENCE: 135

Xaa Asn Asn Arg Pro Val Tyr Ile Pro Arg Pro Arg Pro Pro His Pro
1               5                   10                  15

Arg Leu

<210> SEQ ID NO 136
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 136

Gly Asn Asn Arg Pro Val Tyr Ile Ala Gln Pro Arg Pro Pro His Pro
1               5                   10                  15

Ala Leu

<210> SEQ ID NO 137
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term OH

<400> SEQUENCE: 137

Xaa Asn Asn Arg Pro Val Tyr Ile Pro Arg Pro Arg Pro Pro His Pro
1               5                   10                  15

Arg Leu

<210> SEQ ID NO 138
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Cit
<220> FEATURE:
<223> OTHER INFORMATION: C-term amidated

<400> SEQUENCE: 138

Xaa Asn Asn Arg Pro Val Tyr Ile Pro Arg Pro Arg Pro Pro His Pro
1               5                   10                  15

Xaa Leu

<210> SEQ ID NO 139

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 139

Gly Asn Asn Arg Pro Val Tyr Ile Pro Gln Pro Arg Pro Pro His Pro
1               5                   10                  15

Ala Leu

<210> SEQ ID NO 140
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 140

Gly Asn Asn Arg Pro Val Tyr Ile Ala Gln Pro Arg Pro Pro His Pro
1               5                   10                  15

Arg Leu

<210> SEQ ID NO 141
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 141

Leu Arg Pro His Pro Pro Arg Pro Gln Pro Ile Tyr Val Pro Arg Asn
1               5                   10                  15

Asn Gly

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 142

Arg Pro Val Tyr Ile Pro Gln Pro Arg Pro Pro His Pro Arg Leu
1               5                   10                  15

<210> SEQ ID NO 143
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
```

```
<400> SEQUENCE: 143

Gly Asn Asn Glu Pro Val Tyr Ile Pro Gln Pro Arg Pro Pro His Pro
1               5                   10                  15

Arg Leu

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term OH

<400> SEQUENCE: 144

Gly Asn Asn Arg Pro Val Tyr Ile Pro Gln Pro Arg Pro Pro His Pro
1               5                   10                  15

Arg

<210> SEQ ID NO 145
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Arginal
<220> FEATURE:
<223> OTHER INFORMATION: C-term amidated

<400> SEQUENCE: 145

Xaa Asn Asn Arg Pro Val Tyr Ile Pro Arg Pro Arg Pro Pro His Pro
1               5                   10                  15

Arg Leu

<210> SEQ ID NO 146
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Agp
<220> FEATURE:
<223> OTHER INFORMATION: C-term amidated

<400> SEQUENCE: 146

Xaa Asn Asn Arg Pro Val Tyr Ile Pro Arg Pro Arg Pro Pro His Pro
1               5                   10                  15

Xaa Leu
```

<210> SEQ ID NO 147
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term OPr

<400> SEQUENCE: 147

Xaa Asn Asn Arg Pro Val Tyr Ile Pro Arg Pro Arg Pro Pro His Pro
1               5                   10                  15

Arg Leu

<210> SEQ ID NO 148
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (17)..(17)
<223> OTHER INFORMATION: Cit
<220> FEATURE:
<223> OTHER INFORMATION: C-term amidated

<400> SEQUENCE: 148

Gly Asn Asn Arg Pro Val Tyr Ile Pro Gln Pro Arg Pro Pro His Pro
1               5                   10                  15

Xaa Leu

<210> SEQ ID NO 149
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (17)..(17)
<223> OTHER INFORMATION: Cit
<220> FEATURE:
<223> OTHER INFORMATION: C-term amidated

<400> SEQUENCE: 149

Gly Asn Asn Arg Pro Val Tyr Ile Pro Gln Pro Arg Pro Pro His Pro
1               5                   10                  15

Xaa Leu

<210> SEQ ID NO 150
<211> LENGTH: 18
<212> TYPE: PRT
<213> ORGANISM: Artificial Sequence
<220> FEATURE:
<223> OTHER INFORMATION: Description of Artificial Sequence: Synthetic

```
          peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Cit
<220> FEATURE:
<223> OTHER INFORMATION: C-term amidated

<400> SEQUENCE: 150

Xaa Asn Asn Arg Pro Val Tyr Ile Pro Arg Pro Arg Pro Pro His Pro
1               5                   10                  15

Xaa Leu

<210> SEQ ID NO 151
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Cit
<220> FEATURE:
<223> OTHER INFORMATION: C-term amidated

<400> SEQUENCE: 151

Xaa Asn Asn Arg Pro Val Tyr Ile Pro Arg Pro Arg Pro Pro His Pro
1               5                   10                  15

Xaa Leu

<210> SEQ ID NO 152
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: D-Arg
<220> FEATURE:
<223> OTHER INFORMATION: C-term amidated

<400> SEQUENCE: 152

Xaa Asn Asn Arg Pro Val Tyr Ile Pro Arg Pro Arg Pro Pro His Pro
1               5                   10                  15

Arg Leu

<210> SEQ ID NO 153
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: MeR
<220> FEATURE:
<223> OTHER INFORMATION: C-term amidated

<400> SEQUENCE: 153

Xaa Asn Asn Arg Pro Val Tyr Ile Pro Arg Pro Arg Pro Pro His Pro
1               5                   10                  15

Arg Leu

<210> SEQ ID NO 154
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: NO2R
<220> FEATURE:
<223> OTHER INFORMATION: C-term amidated

<400> SEQUENCE: 154

Xaa Asn Asn Arg Pro Val Tyr Ile Pro Arg Pro Arg Pro Pro His Pro
1               5                   10                  15

Arg Leu

<210> SEQ ID NO 155
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (17)..(17)
<223> OTHER INFORMATION: Har
<220> FEATURE:
<223> OTHER INFORMATION: C-term amidated

<400> SEQUENCE: 155

Xaa Asn Asn Arg Pro Val Tyr Ile Pro Arg Pro Arg Pro Pro His Pro
1               5                   10                  15
```

Arg Leu

<210> SEQ ID NO 156
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (5)..(5)
<223> OTHER INFORMATION: 4tHyp
<220> FEATURE:
<223> OTHER INFORMATION: C-term amidated

<400> SEQUENCE: 156

Xaa Asn Asn Arg Pro Val Tyr Ile Pro Arg Pro Arg Pro Pro His Pro
1               5                   10                  15

Arg Leu

<210> SEQ ID NO 157
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (9)..(9)
<223> OTHER INFORMATION: 4tHyp
<220> FEATURE:
<223> OTHER INFORMATION: C-term amidated

<400> SEQUENCE: 157

Xaa Asn Asn Arg Pro Val Tyr Ile Pro Arg Pro Arg Pro Pro His Pro
1               5                   10                  15

Arg Leu

<210> SEQ ID NO 158
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (11)..(11)
<223> OTHER INFORMATION: 4tHyp
<220> FEATURE:
<223> OTHER INFORMATION: C-term amidated

<400> SEQUENCE: 158

Xaa Asn Asn Arg Pro Val Tyr Ile Pro Arg Pro Arg Pro Pro His Pro
1               5                   10                  15

Arg Leu

<210> SEQ ID NO 159
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Guan
<220> FEATURE:
<223> OTHER INFORMATION: C-term amidated

<400> SEQUENCE: 159

Gly Asn Asn Arg Pro Val Tyr Ile Pro Arg Pro Arg Pro Pro His Pro
1               5                   10                  15

Arg Leu

<210> SEQ ID NO 160
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term N-alpha-Dy675
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term amidated

<400> SEQUENCE: 160

Xaa Asn Asn Arg Pro Val Tyr Ile Pro Arg Pro Arg Pro Pro His Pro
1               5                   10                  15

Arg Leu

<210> SEQ ID NO 161
<211> LENGTH: 19
<212> TYPE: PRT
<213> ORGANISM: Drosphila melanogaster

<400> SEQUENCE: 161

Gly Lys Pro Arg Pro Tyr Ser Pro Arg Pro Thr Ser His Pro Arg Pro
1               5                   10                  15

Ile Arg Val

<210> SEQ ID NO 162
<211> LENGTH: 16
<212> TYPE: PRT
<213> ORGANISM: Myrmecia gulosa

<400> SEQUENCE: 162

Gly Arg Pro Asn Pro Val Asn Asn Lys Pro Thr Pro Tyr Pro His Leu
1               5                   10                  15

<210> SEQ ID NO 163
<211> LENGTH: 20

```
<212> TYPE: PRT
<213> ORGANISM: Pyrrhocoris apterus

<400> SEQUENCE: 163

Val Asp Lys Gly Ser Tyr Leu Pro Arg Pro Thr Pro Pro Arg Pro Ile
1               5                   10                  15
Tyr Asn Arg Asn
            20

<210> SEQ ID NO 164
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term OH

<400> SEQUENCE: 164

Xaa Asn Asn Arg Pro Val Tyr Ile Pro Gln Pro Arg Pro Pro His Pro
1               5                   10                  15
Arg

<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Ornithine
<220> FEATURE:
<223> OTHER INFORMATION: C-term OH

<400> SEQUENCE: 165

Xaa Asn Asn Arg Pro Val Tyr Ile Pro Gln Pro Arg Pro Pro His Pro
1               5                   10                  15

<210> SEQ ID NO 166
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Asn Asn Arg Pro Val Tyr Ile Pro Gln Pro Arg Pro Pro His Pro
1               5                   10                  15
Arg Ile

<210> SEQ ID NO 167
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 167

Gly Ala Asn Arg Pro Val Tyr Ile Pro Gln Pro Arg Pro Pro His Pro
1               5                   10                  15

Arg Ile

<210> SEQ ID NO 168
<211> LENGTH: 8
<212> TYPE: PRT
<213> ORGANISM: Apis mellifera
<220> FEATURE:
<221> NAME/KEY: MOD_RES
<222> LOCATION: (8)..(8)
<223> OTHER INFORMATION: Ile or Leu

<400> SEQUENCE: 168

Pro Arg Pro Pro His Pro Arg Xaa
1               5

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be N-term modified
<220> FEATURE:
<221> NAME/KEY: MOD_RES
<222> LOCATION: (1)..(1)
<223> OTHER INFORMATION: Any neutral residue or a moiety having a net
      positive charge or a positively charged side chain under
      physiological conditions
<220> FEATURE:
<221> NAME/KEY: MOD_RES
<222> LOCATION: (3)..(3)
<223> OTHER INFORMATION: Any residue with a polar side chain or a moiety
      having a net positive charge or a positively charged side chain
      under physiological conditions
<220> FEATURE:
<221> NAME/KEY: MOD_RES
<222> LOCATION: (4)..(4)
<223> OTHER INFORMATION: Any moiety having a net positive charge or a
      positively charged side chain under physiological conditions
<220> FEATURE:
<221> NAME/KEY: MOD_RES
<222> LOCATION: (10)..(10)
<223> OTHER INFORMATION: Any neutral residue with a polar side chain or
      a moiety having a net positive charge or a positively charged side
      chain under physiological conditions
<220> FEATURE:
<221> NAME/KEY: MOD_RES
<222> LOCATION: (11)..(11)
<223> OTHER INFORMATION: Pro or a proline derivative
<220> FEATURE:
<223> OTHER INFORMATION: May be C-term modified
<220> FEATURE:
<223> OTHER INFORMATION: see specification as filed for detailed
      description of substitutions and preferred embodiments

<400> SEQUENCE: 169

Xaa Asn Xaa Xaa Pro Val Tyr Ile Pro Xaa Xaa Arg Pro Pro His Pro
1               5                   10                  15

<210> SEQ ID NO 170
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: May be N-term modified
<220> FEATURE:
<221> NAME/KEY: MOD_RES
<222> LOCATION: (1)..(1)
<223> OTHER INFORMATION: Any neutral residue or a moiety having a net
      positive charge or a positively charged side chain under
      physiological conditions
<220> FEATURE:
<221> NAME/KEY: MOD_RES
<222> LOCATION: (3)..(3)
<223> OTHER INFORMATION: Any residue with a polar side chain or a moiety
      having a net positive charge or a positively charged side chain
      under physiological conditions
<220> FEATURE:
<221> NAME/KEY: MOD_RES
<222> LOCATION: (4)..(4)
<223> OTHER INFORMATION: Any moiety having a net positive charge or a
      positively charged side chain under physiological conditions
<220> FEATURE:
<221> NAME/KEY: MOD_RES
<222> LOCATION: (10)..(10)
<223> OTHER INFORMATION: Any neutral residue with a polar side chain or
      a moiety having a net positive charge or a positively charged side
      chain under physiological conditions
<220> FEATURE:
<221> NAME/KEY: MOD_RES
<222> LOCATION: (11)..(11)
<223> OTHER INFORMATION: Pro or a proline derivative
<220> FEATURE:
<221> NAME/KEY: MOD_RES
<222> LOCATION: (17)..(17)
<223> OTHER INFORMATION: Pro or a proline derivative or a moiety having
      a net positive charge or a positively charged side chain under
      physiological conditions
<220> FEATURE:
<221> NAME/KEY: MOD_RES
<222> LOCATION: (18)..(18)
<223> OTHER INFORMATION: Pro or a proline derivative or a polar moiety
      or a hydrophobic moiety
<220> FEATURE:
<221> NAME/KEY: MOD_RES
<222> LOCATION: (19)..(19)
<223> OTHER INFORMATION: Pro, Ile, Leu, Arg, Val, any branched amino
      acid residue, or not present
<220> FEATURE:
<223> OTHER INFORMATION: May be C-term modified
<220> FEATURE:
<223> OTHER INFORMATION: see specification as filed for detailed
      description of substitutions and preferred embodiments

<400> SEQUENCE: 170

Xaa Asn Xaa Xaa Pro Val Tyr Ile Pro Xaa Xaa Arg Pro Pro His Pro
1               5                   10                  15

Xaa Xaa Xaa

<210> SEQ ID NO 171
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be N-term modified
<220> FEATURE:
<221> NAME/KEY: MOD_RES
<222> LOCATION: (1)..(1)
<223> OTHER INFORMATION: Any neutral residue or a moiety having a net
      positive charge or a positively charged side chain under
      physiological conditions
<220> FEATURE:
<221> NAME/KEY: MOD_RES
<222> LOCATION: (3)..(3)
```

```
<223> OTHER INFORMATION: Any residue with a polar side chain or a moiety
      having a net positive charge or a positively charged side chain
      under physiological conditions
<220> FEATURE:
<221> NAME/KEY: MOD_RES
<222> LOCATION: (4)..(4)
<223> OTHER INFORMATION: Any moiety having a net positive charge or a
      positively charged side chain under physiological conditions
<220> FEATURE:
<221> NAME/KEY: MOD_RES
<222> LOCATION: (10)..(10)
<223> OTHER INFORMATION: Any neutral residue with a polar side chain or
      a moiety having a net positive charge or a positively charged side
      chain under physiological conditions
<220> FEATURE:
<221> NAME/KEY: MOD_RES
<222> LOCATION: (11)..(11)
<223> OTHER INFORMATION: Pro or a proline derivative
<220> FEATURE:
<221> NAME/KEY: MOD_RES
<222> LOCATION: (17)..(17)
<223> OTHER INFORMATION: Pro or a proline derivative or a moiety having
      a net positive charge or a positively charged side chain under
      physiological conditions
<220> FEATURE:
<221> NAME/KEY: MOD_RES
<222> LOCATION: (18)..(18)
<223> OTHER INFORMATION: Pro, Ile, Leu, Arg, Val, any branched amino
      acid residue, or not present
<220> FEATURE:
<223> OTHER INFORMATION: May be C-term modified
<220> FEATURE:
<223> OTHER INFORMATION: see specification as filed for detailed
      description of substitutions and preferred embodiments

<400> SEQUENCE: 171

Xaa Asn Xaa Xaa Pro Val Tyr Ile Pro Xaa Xaa Arg Pro Pro His Pro
1               5                   10                  15

Xaa Xaa

<210> SEQ ID NO 172
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be N-term modified
<220> FEATURE:
<221> NAME/KEY: MOD_RES
<222> LOCATION: (1)..(1)
<223> OTHER INFORMATION: Any neutral residue or a moiety having a net
      positive charge or a positively charged side chain under
      physiological conditions
<220> FEATURE:
<221> NAME/KEY: MOD_RES
<222> LOCATION: (3)..(3)
<223> OTHER INFORMATION: Any residue with a polar side chain or a moiety
      having a net positive charge or a positively charged side chain
      under physiological conditions
<220> FEATURE:
<221> NAME/KEY: MOD_RES
<222> LOCATION: (4)..(4)
<223> OTHER INFORMATION: Any moiety having a net positive charge or a
      positively charged side chain under physiological conditions
<220> FEATURE:
<221> NAME/KEY: MOD_RES
<222> LOCATION: (10)..(10)
<223> OTHER INFORMATION: Any neutral residue with a polar side chain or
      a moiety having a net positive charge or a positively charged side
      chain under physiological conditions
<220> FEATURE:
<221> NAME/KEY: MOD_RES
<222> LOCATION: (11)..(11)
<223> OTHER INFORMATION: Pro or a proline derivative
```

```
<220> FEATURE:
<221> NAME/KEY: MOD_RES
<222> LOCATION: (17)..(17)
<223> OTHER INFORMATION: Pro or a proline derivative or a polar moiety
      or a hydrophobic moiety
<220> FEATURE:
<221> NAME/KEY: MOD_RES
<222> LOCATION: (18)..(18)
<223> OTHER INFORMATION: Pro, Ile, Leu, Arg, Val, any branched amino
      acid residue, or not present
<220> FEATURE:
<223> OTHER INFORMATION: May be C-term modified
<220> FEATURE:
<223> OTHER INFORMATION: see specification as filed for detailed
      description of substitutions and preferred embodiments

<400> SEQUENCE: 172

Xaa Asn Xaa Xaa Pro Val Tyr Ile Pro Xaa Xaa Arg Pro Pro His Pro
1               5                   10                  15

Xaa Xaa
```